(12) United States Patent
Koerber et al.

(10) Patent No.: US 11,310,977 B2
(45) Date of Patent: Apr. 26, 2022

(54) **SPINACH PLANTS RESISTANT TO AT LEAST *PERONOSPORA FARINOSA* RACES 8, 9, 11, 13 AND 16**

(71) Applicant: NUNHEMS B.V., Nunhem (NL)

(72) Inventors: Frederike Koerber, Marbach am Neckar (DE); Robert Johannes Martinus Raedts, Nunhem (NL)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 16/964,686

(22) PCT Filed: Jan. 24, 2019

(86) PCT No.: PCT/EP2019/051799
§ 371 (c)(1),
(2) Date: Jul. 24, 2020

(87) PCT Pub. No.: WO2019/145447
PCT Pub. Date: Aug. 1, 2019

(65) Prior Publication Data
US 2021/0054399 A1 Feb. 25, 2021

(30) Foreign Application Priority Data
Jan. 26, 2018 (EP) ..................... 18153717

(51) Int. Cl.
*C12N 15/82* (2006.01)
*C12Q 1/6895* (2018.01)
*A01H 6/02* (2018.01)
*A01H 5/12* (2018.01)

(52) U.S. Cl.
CPC ............... *A01H 6/028* (2018.05); *A01H 5/12* (2013.01); *C12N 15/8279* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 8,563,807 | B2 | 10/2013 | Dijkstra | |
|---|---|---|---|---|
| 9,402,363 | B1 | 8/2016 | Feitsma et al. | |
| 2013/0055454 | A1* | 2/2013 | den Braber | C12Q 1/6895 800/260 |
| 2017/0127641 | A1 | 5/2017 | De Visser | |
| 2017/0127642 | A1 | 5/2017 | De Visser | |
| 2017/0327839 | A1* | 11/2017 | Feitsma | A01H 5/12 |

FOREIGN PATENT DOCUMENTS

| CN | 107541551 A | 1/2018 | |
|---|---|---|---|
| EP | 1816908 A2 | 8/2007 | |
| EP | 2848114 A1 | 3/2015 | |
| EP | 2912940 A1 | 9/2015 | |
| WO | 2013064436 A1 | 5/2013 | |
| WO | 2015036378 A1 | 3/2015 | |
| WO | 2015036469 A1 | 3/2015 | |
| WO | 2015054339 A1 | 4/2015 | |
| WO | 2017084724 A1 | 5/2017 | |
| WO | 2017194073 A1 | 11/2017 | |
| WO | WO2018/059651 A1 * | 4/2018 | |
| WO | WO2018/060474 A1 * | 4/2018 | |

OTHER PUBLICATIONS

Predicted Spinacia oleracea protein YLS7-like (LOC110782400), mRNA, GenBank accession No. XM_021986551, version XM_021986551.1, published Aug. 1, 2017.*
She et al., 2018, Fine mapping and candidate gene screening of the downy mildew resistance gene RPF1 in Spinach, Theoretical and Applied Genetics 131: 2529-2541.*
Irish et al., 2008, Characterization of a Resistance Locus (Pfs-1) to the Spinach Downy Mildew Pathogen (Peronospora farinosa f. sp. spinaciae) and Development of a Molecular Marker Linked to Pfs-1. Phytopathology 90:894-900.*
Correll et al., 2011, Spinach: better management of downy mildew and white rust through genomics, European Journal of Plant Pathology 129: 193-205.*
"Denomination of Pfs: 16, a new race of downy mildew in spinach", Plantum Press Release, Mar. 15, 2016, pp. 1-2.
"Differential Sets Peronospora farinosa f. sp. spinaciae (P. effuse)", International Seed Federation, Apr. 2018, pp. 1-2.
Brandenberger, et al., "Evaluation of Spinach Germplasm for Resistance to a New Race (Race 4) of Peronospora farinosa f. sp. spinaciae", HortScience, vol. 27, Issue 10, Oct. 1992, pp. 1118-1119.
Correll, et al., "Guidelines for Spinach Downy Mildew: Peronospora farinosa f. sp. spinaciae (Pfs)", Collaboration for Plant Pathogen Strain Identification, 2010, pp. 1-8.
Correll, et al., "Project Title: Race diversity and the biology of the spinach downy mildew pathogen", CLGRB Annual Report, Apr. 1, 2013-Mar. 31, 2014, pp. 1-10.
Correll, et al., "Project Title: Race diversity and the biology of the spinach downy mildew pathogen", CLGRB Annual Report, Apr. 1, 2016-Mar. 31, 2017, pp. 1-13.
Correll, et al., "Spinach: better management of downy mildew and white rust through genomics", European Journal of Plant Pathology, vol. 129, Issue 2, Feb. 2011, pp. 193-205.
Differential Sets—Peronospora farinosa f.sp. spinaciae, International Seed Federation, Aug. 2016, pp. 1-2.

(Continued)

*Primary Examiner* — Bratislav Stankovic
(74) *Attorney, Agent, or Firm* — ArentFox Schiff LLP

(57) ABSTRACT

The invention relates to a cultivated spinach plant having a new resistance against at least *Peronospora farinosa* races 8, 9, 11, 13 and 16, seed, cell cultures and progeny of said plant, use of the plant with the resistance, and methods for generating and identifying such a plant.

17 Claims, 4 Drawing Sheets

Specification includes a Sequence Listing.

(56) References Cited

OTHER PUBLICATIONS

European Search Report for EP Patent Application No. 18153717.6, dated Jun. 4, 2018, pp. 1-5.

Feng, et al., "Identification of New Races and Deviating Strains of the Spinach Downy Mildew Pathogen *Peronospora farinosa* f. sp. spinaciae", Plant Disease, vol. 98, Issue 1, Jan. 2014, pp. 145-152.

Handke, et al., "Detection of a linkage of the four dominant mildew resistance genes "M1M2M3M4" in spinach from the wildtype Spinacia turkestanica", Gartenbauwissenschaft, vol. 65, Issue 2, 2000, pp. 73-78.

International Search Report for PCT Patent Application No. PCT/EP2019/051799, dated Mar. 25, 2019, pp. 1-6.

Irish, et al., "Three New Races of the Spinach Downy Mildew Pathogen Identified by a Modified Set of Spinach Differentials", Plant Disease, vol. 91, Issue 11, Oct. 9, 2007, pp. 1392-1396.

Khattak, et al., "A genetic linkage map of Spinacia oleracea and localization of a sex determination locus", Euphytica, vol. 148, Issue 3, Jun. 2, 2006, pp. 311-318.

Nguyen, et al., "Effect of plant growth regulator combination and culture period on in vitro regeneration of spinach (*Spinacia oleracea* L)", Plant Biotechnology Reports, vol. 7, Issue 1, Jul. 17, 2012, pp. 99-108.

Smith, et al., "Downy mildew on spinach: A second race of fungus has been found on Califlay variety in the coastal valley area of California", California Agriculture, vol. 15, Issue 10, Oct. 1, 1961, p. 5.

Smith, et al., "Immunity to race 2 of Spinach downy mildew", Phytopathology, vol. 52, Issue 7, 1962, pp. 597-599.

Smith, et al., "New spinach immune to mildew: Hybrid variety developed by plant breedng program intended for use where Viroflay is adapted, produces comparable yield", California Agriculture, vol. 10, Issue 7, Jul. 1, 1956, p. 15.

Xu, et al., "Draft genome of spinach and transcriptome diversity of 120 Spinacia accessions", Nature Communications, vol. 8, Article No. 15275, May 24, 2017, pp. 1-10.

\* cited by examiner

Figure 1

```
SpinachBase      1 aacagaaattccgaatgcttcaacgttagttatcttcattggctgctgct    50
                   ||||:|||||||||||||||||||||||||||||||||||||||||||||
SEQ ID NO: 1     1 aacaraaattccgaatgcttcaacgttagttatcttcattggctgctgct    50

SpinachBase     51 gcgttttggtggggaccacaactgggttcctactatctggttatttagc   100
                   ||:|||||||||||||||||||||||||||||||||||:||:||||||||
SEQ ID NO: 1    51 gckttttggtggggaccacaactgggttcctactatytgrttatttagc   100

SpinachBase    101 atgtaaaccgattgcttcgcaaaccaatgaccagaagaaaggacaacaac   150
                   |||||||||||||||||||||:|||||||||||||||||||||||||:||
SEQ ID NO: 1   101 atgtaaaccgattgcttcgcraaccaatgaccagaagaaaggacaacrac   150

SpinachBase    151 atcaaatttcgggatgtcttgcatgaaaacttcatctgggacatcaaggt   200
                   ||||||||||||||||||||||||||||||||||||||||||||||||||
SEQ ID NO: 1   151 atcaaatttcgggatgtcttgcatgaaaacttcatctgggacatcaaggt   200

SpinachBase    201 gcag   204
                   ||||
SEQ ID NO: 1   201 gcag   204
```

Figure 2

```
SpinachBase    1 cggtctcctttaccggaattatcgctctcgaggatcggaaaaatgctcgt   50
                 ||||||||||||||||||||||||||||||||||||||||||||||||||
SEQ ID NO: 3   1 cggtctcctttaccggaattatcgctctcgaggatcggaaaaatgctcgt   50

SpinachBase   51 attatttagggtttgagctgaatctccatcaccaataagggcaggcaatg  100
                 ||||.|||||||.||||||||||||||||||||||||.|||||||||||.|
SEQ ID NO: 3  51 attacttagggcttgagctgaatctccatcaccaacaagggcaggcaacg  100

SpinachBase  101 atctcgaaagattattcaaattgtaaaatgaagcataattcgcgttatta  150
                 ||||||||||||||||||||||||||||||||||||||||||        |
SEQ ID NO: 3 101 atctcgaaagattattcaaattgtaaaatgaagcataattcgc------a  144

SpinachBase  151 ttattattattcgacattctcaatttatcataattagacggcgtattcc   200
                 |||||||||||||||||||||||||||||||||||||||||.|||||||.||
SEQ ID NO: 3 145 ttattattattcgacattctcaatttatcataattagacggcgtatgcc   194

SpinachBase  201 accatacccgtgtctaaacccatggatcgaccattgataaccgggtttat  250
                 ||||||||||||||||||||||||||||||||||||||||||||||||||
SEQ ID NO: 3 195 accatacccgtgtctaaacccatggatcgaccattgataaccgggtttat  244

SpinachBase  251 gaatcattgaatttgttttgactacccctaggggtgacctttttgcaatat 300
                 ||||||||||||||||||||||||||||||||||||||||||||||||||
SEQ ID NO: 3 245 gaatcattgaatttgttttgactacccctaggggtgacctttttgcaatat 294

SpinachBase  301 ccact    305
                 |||||
SEQ ID NO: 3 295 ccact    299
```

Figure 3

```
SEQ ID NO: 5      1 --------------------------------------------------    0

SEQ ID NO: 7      1 ggaagaacattagtactagcttaattgaatattccataacttttatttt   50

SEQ ID NO: 5      1 -------------------------gcaaatagatgtgaaataact      21
                                            |||||||||||||||||||||
SEQ ID NO: 7     51 tgcttaattagattgtggtttgaagctatgcaaatagatgtgaaataact 100

SEQ ID NO: 5     22 tttta-------------------------catatgcaaatatatt      42
                    |||||                         |  |||||||||.||.
SEQ ID NO: 7    101 ttttattttgcttaattagattgtggtttgaagc-tatgcaaatagatg  149

SEQ ID NO: 5     43 ggaaatagcgaat-tata-tatataatatggtttacataggtttcgacag   90
                    .|||||||||||| ||||  ||||||||||||||||||||.|||||||||
SEQ ID NO: 7    150 tgaaatagcgaatatatattatataatatggtttacatagatttcgacag  199

SEQ ID NO: 5     91 agggcttactcgtatttatttgataatatgtcatatttgacg-agaata   139
                    ||||.||||||||||||.|||||||||||||.|||||||||.| |.||||
SEQ ID NO: 7    200 agggGttactcgtatttgtttgataatatttcatatttgatgaaaaata   249

SEQ ID NO: 5    140 agaatgact-----------------------------------------  148
                    .|.||.|||
SEQ ID NO: 7    250 gggattacttaatcttaaaatagcatttatgctttactctaagggtgtta  299
```

Figure 4

```
SEQ ID NO: 6     1  --------------------------------------------------     0

SEQ ID NO: 8     1  gcaacggcaagctctcgaagggcacgtagggccttagatctgcgaataag    50

SEQ ID NO: 6     1  ----------------------------gctgctgcatcataggGtgata    22
                                                ||||||||||||||||||||||
SEQ ID NO: 8    51  gtaagccctgaaggtccactggatcaaagctgctgcatcataggGtgata   100

SEQ ID NO: 6    23  gttccttccttttcctttatcattggtagatcgtttggcaaaagcctg-    71
                    ||||||||||||||||||||||||||||||||||||.||||||||||||
SEQ ID NO: 8   101  gttccttccttttcctttatcattggtagatcttttggcaaaagcctgt   150

SEQ ID NO: 6    72  -tggcaccaatacaacaaaaggttaagataaatttgtttgctatgaccat   120
                    |||||||||||||||||||||||||||||||||||||||||||||||||
SEQ ID NO: 8   151  atggcaccaatacaacaaaaggttaagataaatttgtttgctatgaccat   200

SEQ ID NO: 6   121  attctaatcaaaagaacatagcaacata-----------              148
                    ||||||||||||||||||||||||||||
SEQ ID NO: 8   201  attctaatcaaaagaacatagcaacatattcaagggg                237
```

SPINACH PLANTS RESISTANT TO AT LEAST PERONOSPORA FARINOSA RACES 8, 9, 11, 13 AND 16

CROSS-REFERENCE TO RELATED APPLICATIONS

This application is a National Stage Entry of PCT/EP2019/051799, filed Jan. 24, 2019, which claims priority to EP application No. 18153717.6, filed Jan. 26, 2018, the disclosures of each of which are hereby incorporated by reference in their entireties.

FIELD OF THE INVENTION

The invention relates to a cultivated spinach plant having a new resistance against *Peronospora farinosa* races, seed, cell cultures and progeny of said plant, use of the plant with the resistance, and methods for generating such a plant.

BACKGROUND OF THE INVENTION

Spinach (*Spinacia oleracea*) is one of the edible plants in the family Amaranthaceae, genus *Spinacia*. It is native to western and central Asia. In that part of the world, the wild relatives of Spinach, *Spinacia turkestanica* and *Spinacia tetrandra* are found.

Spinach has become an important vegetable crop in many parts of the world, with the top spinach producing county being China (with a production of 19500000 Mt in 2012), followed by USA, Japan and Turkey (FAOSTAT). Globally about 1 million ha of spinach is grown in Asia and about 35,000 ha in each of the EU, USA and Japan (see Correll et al., 2011, Eur J Plant Pathol 129: 193-205). Part of the increase in spinach demand is likely due to an increased health-consciousness of consumers and awareness of the beneficial properties of spinach. Spinach leaves are rich in beta-carotene, lutein, folic acid, vitamin C, calcium, iron and antioxidants (United States Department of Agriculture National Nutrient Database). The demand for fresh spinach has significantly increased over recent years.

Due to this increase in production over the last decades, incidence and severity of one of the most damaging pathogens of spinach, downy mildew of spinach, caused by races of the oomycete *Peronospora farinosa* f.sp. *spinaciae* (Pfs; synonym *P. effusa*) has increased concomitantly. In 1990 only three races of Pfs were known, however between 1990 and 2017 thirteen new races were identified. The emergence of new races of Pfs makes this pathogen a major threat for spinach production globally and identifying new sources of resistance is therefore necessary.

Historically, Pfs race 1 (Pfs:01 or Pfs1) was first reported in 1824 and resistance to race 1 was identified later in two Iranian accessions (PI140467 and PI140464) and incorporated into commercial hybrid varieties, such as Califlay (Smith and Zahara, California Agriculture, July 1956). In 1958 Pfs race 2 appeared and a few years later a single dominant gene imparting resistance against race 1 and 2 was identified (Smith et al. 1961 and 1962). In 1976 race 3 appeared, race 4 was identified in 1990, and resistances against both strains were found quickly. The rapid emergence of new races thereafter, lead to the identification of further new resistance genes and their incorporation into commercial varieties, as well as development of standardized test such as the differential seedling test (see International Seed Federation—Guidelines for Spinach Downy Mildew, December 2015 and "Differential Sets—*Peronospora farinosa* f.sp. *spinaciae*", August 2016; world wide web at worldseed dot org/isf/differential_hosts dot html). Some of these varieties are also used as host differentials for determining the race of isolates of Pfs as indicated in Table 1 below.

TABLE 1

Disease reactions of spinach differentials for determining the race identification of isolates of the spinach downy mildew pathogen, *Peronospora farinosa* f. sp. *spinaciae* as of December 2015 and August 2016

| Variety | Pfs 1 | Pfs 2 | Pfs 3 | Pfs 4 | Pfs 5 | Pfs 6 | Pfs 7 | Pfs 8 | Pfs 9 | Pfs 10 | Pfs 11 | Pfs 12 | Pfs 13 | Pfs 14 | Pfs 15 | Pfs 16 |
|---|---|---|---|---|---|---|---|---|---|---|---|---|---|---|---|---|
| Viroflay | + | + | + | + | + | + | + | + | + | + | + | + | + | + | + | + |
| Resistoflay | − | − | + | + | + | + | + | + | + | + | + | + | + | + | + | + |
| Califlay | − | + | − | + | − | + | + | − | − | + | − | − | + | − | + | − |
| Clermont | − | − | − | − | + | + | + | + | + | + | + | + | + | + | − | + |
| Campania | − | − | − | − | − | + | − | + | + | + | − | + | +/− | + | − | − |
| Boeing | − | − | − | − | − | − | − | + | − | + | − | + | − | + | − | + |
| Lion | − | − | − | − | − | − | − | − | + | − | − | − | − | − | − | − |
| Lazio | − | − | − | − | − | − | − | − | − | + | + | + | + | − | − | + |
| Whale | − | − | − | (−) | − | (−) | (−) | − | − | + | − | − | + | (−) | + | − |
| Pigeon | − | − | − | − | − | − | − | − | − | − | − | − | − | + | − | + |
| Caladonia | − | − | − | − | − | − | − | − | − | − | − | − | − | − | + | − |
| Meerkat | − | − | − | − | − | − | − | − | − | − | − | − | − | − | − | + |

Legend: (−means resistant reaction (no sporulation observed on cotyledons in the differential seedling test, HR resistant); +means susceptible (sporulation observed on cotyledons in the differential seedling test), +/−means variability in number of resistant and susceptible plants observed, (−) means reduced level of infection or intermediate resistance)

In 2016 a new race of downy mildew was identified (Plantum press release, Mar. 15, 2016). An isolate was first identified in Salinas, Calif. USA March 2015 and initially designated UA201519B (also referred to as UA1519B). The isolate was evaluated for disease development in a test against a standard set of differential varieties, and the International Working Group on *Peronospora* (IWGP) determined that the isolate was a new race. The IWGP named it Pfs: 16 once it became clear that isolates with the same reaction pattern occurred in many locations. It was added to the standard differential table shown in this application as Table 1.

In 2018 another new race was denominated by the IWGP, Pfs17 (UA1014, or US1602). Also a new set of host differentials has been released by the International Seed Federation (ISF), to differentiate isolates Pfs 1 to Pfs 17. See the world wide web at worldseed.org/our-work/plant-health/differential-hosts/, document under the link 'Downy Mildew", referred to as "Spinach-downy-mildew_April2018.pdf".

Commercial spinach varieties are mostly hybrids, produced by crossing a male and a female inbred line, although also some open pollinated varieties exist. The male and female parent line generally carry different resistance genes each. For example, the hybrid variety *Andromeda* (bred by Nunhems; see patent application U.S. Pat. No. 8,563,807) is resistant against Pfs 1-12 and Pfs14. In this variety, resistance against Pfs 1, 3, 5, 8, 9, 11, 12 and 14 is conferred by a resistance gene from one inbred parent line, while resistance against Pfs 1-10 is conferred by a resistance gene from the other inbred parent line. Both parent lines are homozygous for the resistance gene. Optimal combination of resistances is a difficult puzzle, especially since some resistance genes are not dominant and/or map to the same locus, making it impossible to stack all known resistance genes in a hybrid. Thus, additional resistance genes are constantly desired in the field of spinach breeding.

WO2015054339 describes a "*Spinacia oleracea* spinach plant comprising in its genome an introgressed locus from *Spinacia tetrandra* that confers broad-spectrum resistance to *Peronospora farinosa* 1 sp. *spinaciae*.", said broad-spectrum resistance comprising "resistance to races 7, 10, 11, 12, 13, and 14 of *Peronospora farinosa* 1 sp. *spinaciae* (Pfs), or to races 1-14 and UA4712 of *Peronospora farinosa* 1 sp. *spinaciae* (Pfs)" (isolate UA4712 was later denominated *Peronospora farinosa* 1 sp. *spinaciae* (Pfs) race 15 by the IWGP), where "the introgressed locus is defined as flanked in the *Spinacia tetrandra* genome by sequences at least 95% identical to SEQ ID NOs: 1 or 2" and also that "DM resistance from *S. tetrandra* was between markers E33/M62-231 at 0.0 cM and E39/M47-203 at 10.3 cM, on chromosome 6 of the public map" (Khattak et al., Euphytica 148:311-318, 2006). SEQ ID NOs: 1 and 2 of WO2015054339, which flank the resistance-conferring locus, were added to this application as SEQ ID NOs: 4 and 5, respectively.

WO2013064436 (EP2586294) describes "a new resistance gene—named R6—that confers resistance onto spinach plants to downy mildew races Pfs 1, Pfs 2, Pfs 3, Pfs 4, Pfs 5, Pfs 6, Pfs 9, Pfs 11, Pfs 12, Pfs 13 and UA4410" (see also Table 1 on page 19 of WO2013/064436; type strain UA4410 is designated Pfs14 by the IWGP since 2011). No markers were provided. R6 is not described to confer resistance to Pfs races 7, 8 and 10.

EP2912940 (US2015240256) describes plants resistant to *Peronospora farinosa*, conferred by "a combination of alleles which is selected from the group consisting of allele A, allele Vt, and allele C" . . . "combination of alleles comprises alleles A and C and the plant is resistant to at least *Peronospora farinosa* f. sp. *spinaciae* races 7, 8, 10, 11, 12, 14, and isolate UA4712; the combination of alleles comprises alleles A and Vt, and the plant is resistant to at least *Peronospora farinosa* f. sp. *spinaciae* races 7, 8, 10, 11, 12, 13, and 14; or the combination of alleles comprises alleles C and Vt, and the plant is resistant to at least *Peronospora farinosa* f. sp. *spinaciae* races 7, 8, 10, 11, 12, 13, and isolate UA4712" (underline added). Isolate UA4712 is currently known as Pfs 15. Thus, the resistance disclosed in EP2912940 is directed to combinations of alleles.

U.S. Pat. No. 9,402,363 describes a "method of identifying a spinach plant comprising an R15 allele, wherein said allele confers resistance to at least *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs:14, Pfs:15 and isolate UA1014 and does not confer resistance to *Peronospora farinosa* f. sp. *spinaciae* race Pfs:7, and wherein said allele is as found in a plant grown from a seed of which a representative sample was deposited with the NCIMB under NCIMB accession number 42466" and four marker sequences within 20 cM (centiMorgan) for doing so. Furthermore, "in homozygous state the R15 allele, as found . . . , also confers resistance to *Peronospora farinosa* f. sp. *spinaciae* race Pfs:8 and at least intermediate resistance to Pfs:10". Isolate UA1014 is currently not a numbered Pfs race acknowledged by the IWGP. U.S. Pat. No. 9,402,363 discloses "at least intermediate resistance to races Pfs:8, Pfs:10 and does not confer resistance to *Peronospora farinosa* f. sp. *spinaciae* race Pfs:7". The resistance to Pfs:8, Pfs:10 is further described to function as follows "homozygous or heterozygous presence of the R15 resistance conferring allele influences the expression of the trait of the invention for *Peronospora farinosa* f. sp. *spinaciae* races Pfs:8 and Pfs:10".

US20170127641 describes "a spinach plant comprising resistance against *Peronospora farinosa* races 1-9, 11-15 and isolate UA1014APLP." Isolate UA1014APLP is currently not a numbered Pfs race acknowledged by the IWGP. US20170127641 does not disclose resistance to Pfs race 10. US20170127641 does disclose resistance to Pfs race 3-5. No markers for the resistance gene or genes were disclosed.

US20170127642 describes "a spinach plant comprising resistance against *Peronospora farinosa* races 1-9, 11-15 and isolate UA1014APLP." Isolate UA1014APLP is currently not a numbered Pfs race acknowledged by the IWGP. US20170127642 does not disclose resistance to Pfs race 10. US20170127642 does disclose resistance to Pfs race 3-5. No markers for the resistance gene or genes were disclosed.

WO2017194073 describes a "non R-gene mediated broad spectrum resistance to at least the officially recognized *Peronospora farinosa* f. sp. *spinaciae* races Pfs: 1, Pfs:2, Pfs:3, Pfs:4, Pfs:5, Pfs:6, Pfs:7, Pfs:8, Pfs:9, Pfs: 10, Pfs: 11, Pfs: 12, Pfs: 13, Pfs: 14, Pfs: 15 and Pfs: 16, wherein the resistance is caused by a new locus designated p10 and wherein the resistance caused by the p10 locus is at least of an intermediate level" and "In contrast to a resistance mediated by a dominant R-gene, the p10 locus of the invention only provides resistance when homozygously present".

Correll et al., 2013 describes varieties Coati and Meerkat, which are resistant to Pfs 1-15 and several other isolates of *P. farinosa*, including UA1414, UA1012 and UA1312. Coati and Meerkat are F1 hybrids. Meerkat was later shown to be susceptible to Pfs race 16 (Plantum press release, Mar. 15, 2016).

Variety Callisto F1 is a spinach variety bred by Nunhems and is resistant against Pfs race 1-14 and Pfs 16 described as HR or high resistance. It is a hybrid and the Pfs resistances are obtained from stacking various dominant genes. Rpf3 (also known as R3), a gene described in a.o. Correl et al., 2011, confers the resistance against Pfs 16.

Variety Novico F1 is an industry type spinach bred by Nunhems and is resistant against Pfs race 1-12 and 14-16 described as HR (high resistance). It is a hybrid and the Pfs resistances are obtained from stacking various dominant genes. Rpf3, a gene described in a.o. Correl et al, 2011, confers the resistance against Pfs 16.

Variety Palco F1 is an industry type spinach bred by Nunhems and is resistant against Pfs race 1-5, 8, 9, 11, 12, 14 and 16 described as HR. It is a hybrid and the Pfs resistances are obtained from stacking various dominant genes. Rpf3 confers the resistance against Pfs 16.

Variety Scorpius F1 is a fresh market spinach bred by Nunhems and is resistant against Pfs race 1-14 and 16 described as HR. It is a hybrid and the Pfs resistances are obtained from stacking various dominant genes. Rpf3 confers the resistance against Pfs 16.

Variety *Andromeda* F1 mentioned above is a fresh market spinach bred by Nunhems and contains resistance against Pfs race 1-12 and 14-16 described as HR. It is a hybrid and the Pfs resistances are obtained from stacking various dominant genes. Rpf3 confers the resistance against Pfs 16.

Various other companies also sell spinach varieties, containing stacks of resistance genes. Newly introduced spinach varieties are almost exclusively hybrids.

WO2015036378 discloses "a new dominant resistance gene, designated RPF13". The gene provides "resistance against at least *Peronospora farinosa* races 7-14, . . . conferred by a single gene. The gene . . . further optionally confers resistance against one or more or all of *Peronospora farinosa* races 1-6, or at least against Pfs 1-2 and Pfs 4-6 . . . ". Isolate UA4712 is currently known as Pfs 15. RPF13 does not confer resistance to Pfs16, as is also shown in the Examples of this application.

Xu, C. et al. (2017, Nat. Commun. 8, 15275 doi: 10.1038/ncomms15275) "Draft genome of spinach and transcriptome diversity of 120 *Spinacia* accessions" (2017) published the genome sequence of a Chinese cultivar of spinach, Sp75. The sequence can be analyzed in the online database "SpinachBase" found on the world wide web at spinachbase.org. Herein, the six chromosomes of spinach can be queried, e.g. by Blast analysis.

If a breeder wants to create a spinach variety comprising resistance to all IWGP-acknowledged *Peronospora farinosa* races, that is Pfs race 1 to 16, or a variety having resistance to at least Pfs races 8, 9, 11, 13 and 16, the breeder must combine several of the known resistance genes. No single gene is known that confers resistance to all known races of *Peronospora farinosa*, or to Pfs races 8, 9, 11, 13 and 16, or especially a single gene conferring dominant resistance to at least Pfs races 8, 9, 11, 13 and 16. Furthermore, it is not possible to combine all resistance genes (a full stack), since some Pfs resistance genes are allelic. This limits the possible combinations of resistance genes, thus new genes that allow for new combinations are much sought after.

Based on the literature, such as Correll and Koike (supra) and Feng et al. (2014), Plant Disease, Vol. 96 No. 1, page 145-152, the resistance towards Pfs races provided by the different RPF resistance genes can be summarized as follows (−=resistant, +=susceptible):

|       | Pfs1 | 2 | 3 | 4 | 5 | 6 | 7 | 8 | 9 | 10 | 11 | 12 | 13 | 14 | 15 | 16 | 17 |
|-------|------|---|---|---|---|---|---|---|---|----|----|----|----|----|----|----|----|
| RPF1  | −    | − | − | − | − | − | − | + | − | +  | −  | +  | −  | +  | −  | −  | +  |
| RPF2  | −    | − | − | − | − | − | − | − | − | −  | +  | +  | +  | +  | −  | +  | +  |
| RPF3  | −    | + | − | + | − | + | + | − | − | +  | −  | −  | +  | −  | +  | −  | +  |
| RPF4  | −    | − | − | − | + | + | + | + | + | +  | +  | +  | +  | +  | −  | +  | +  |
| RPF5  | −    | − | + | + | + | + | + | + | + | +  | +  | +  | +  | +  | +  | +  | +  |
| RPF6  | −    | − | − | − | − | + | − | + | + | +  | −  | +  | +  | +  | −  | −  | +  |
| RPF7  | −    | − | − | − | − | − | − | + | + | +  | −  | +  | −  | +  | −  | −  | +  |
| RPF8  | −    | − | − | − | − | − | − | + | − | +  | −  | +  | −  | +  | −  | −  | +  |
| RPF9  | −    | − | − | − | − | − | − | − | − | −  | −  | −  | −  | +  | +  | +  | −  |
| RPF11 | −    | − | − | + | − | − | − | − | − | −  | −  | −  | −  | −  | −  | +  | −  |
| RPF12 | −    | − | − | − | − | − | − | − | − | −  | −  | −  | −  | −  | −  | +  | −  |

WO2015036469 discloses "a new dominant resistance gene, designated RPF12". The plant provides "resistance against at least *Peronospora farinosa* races 7-14, . . . conferred by a single gene . . . RPF12 . . . further optionally confers resistance against one or more or all of *Peronospora farinosa* races 1-6, or at least against Pfs 1-2 and Pfs 4-6". RPF12 does not confer resistance to Pfs16, as is also shown in the Examples of this application. Also variety Pegasum contains RPF12 and is described to be susceptible to race Pfs16, see Table 3 of Correll and Koike, Race diversity and the biology of spinach downy mildew pathogen, CLGRB Annual Report, Apr. 1 2016 to Mar. 31 2017.

EP2848114 discloses "The invention provides a spinach plant comprising resistance against at least *Peronospora farinosa* races 7-14, wherein said resistance is conferred by a single gene . . . . RPF11 . . . further optionally confers resistance against one or more of *Peronospora farinosa* races 1-6. In one aspect the RPF11 gene, therefore, confers resistance against all currently known pathogenic Pfs races, races 1-14, when in homozygous or heterozygous form in the plant . . . ". RPF11 does not confer resistance to Pfs16, as is also shown in the Examples of this application. Also varieties Virgo, Volans and Antalia contain RPF11 and are described to be susceptible to Pfs16, see Table 3 of Correll and Koike, Race diversity and the biology of spinach downy mildew pathogen, CLGRB Annual Report, Apr. 1 2016 to Mar. 31 2017.

There is a need to provide new resistance genes, especially against the new races such as Pfs16 and Pfs17.

SUMMARY OF THE INVENTION

It is an object of this invention to provide a cultivated spinach plant comprising an introgression fragment from a wild relative of spinach, said fragment having a single gene conferring dominant resistance to at least *Peronospora farinosa* races 8, 9, 11, 13 and 16, preferably to at least races 8, 9, 11, 13, 16 and 17. In addition, the gene confers resistance, at least when the gene is in homozygous form, to Pfs races 1 to 7 and resistance to Pfs races 12 and 14. In a further aspect, the gene confers resistance against Pfs isolate UA0514 and/or other Pfs isolates, especially also against the new race Pfs 17. The resistance against the new race Pfs 17 appears also to be dominant. Thus, in homozygous form the gene confers resistance to races Pfs 1-9, 11-14 and 16 and 17, whereby resistance against at least races 8, 9, 11, 13, 16 (and likely also against Pfs17) is also conferred when the gene is in heterozygous form. The dominance for the other races can easily be tested by the person skilled in the art, as described herein.

The gene does not confer resistance to Pfs races 10 and 15, neither when it is in homozygous or heterozygous form.

The introgression fragment comprising the gene is from a wild relative of spinach. In in one preferred aspect the wild relative of spinach is *Spinacia turkestanica*.

The resistance gene is designated RPF15.

In homozygous form (two copies) RPF15 confers resistance against races Pfs 1 to Pfs9, Pfs 11 to Pfs14 and to Pfs 16 and Pfs 17, i.e. against a total of 15 of the 17 known official races. Importantly, the resistance is dominant with respect to races Pfs 8, 9, 11, 13 and 16 (i.e. one copy of the RPF15 gene, or the introgression fragment comprising the RPF15 gene, is sufficient to confer resistance against a particular race), and likely also against Pfs17. To test or confirm the dominance, the RPF15 gene needs to be present in heterozygous form in a susceptible spinach plant, and then the resistance against different Pfs races, such as Pfs17, can be tested. If the RPF15 gene still does confer resistance against a particular race when only one copy of the introgression fragment is present in the spinach genome, then the resistance against that race is dominant.

When the RPF15 gene is in homozygous form the resistance against Pfs races 12 and 14 is classified as intermediate resistance, meaning that plants inoculated with race Pfs12 or Pfs14 may occasionally show some slight symptoms of chlorosis and/or sporulation, but at a later stage and to a much lower extent than a susceptible plant. Under normal field conditions the plants will be resistant to these races, unless there is a very high disease pressure of those races in the field, which might result in some disease symptoms developing (albeit at a late stage). Therefore, throughout this document, reference will be made to 'resistance' to Pfs 12 and Pfs 14 being conferred by the RPF15 gene and it is understood that the resistance is an intermediate resistance as known in the art and as commonly designated using the symbol (−).

In one embodiment, RPF15 confers dominant resistance to at least Pfs races 8, 9, 11, 13 and 16, preferably to races 8, 9, 11, 13, 16 and 17, and further confers resistance, at least when RPF15 is in homozygous form, to Pfs races 1 to 7, to Pfs race 12 and 14, and to Pfs isolate UA0514 and possibly also to other Pfs isolates. Thus, it is an object of the invention to provide a single gene conferring dominant resistance to at least Pfs races 8, 9, 11, 13 and 16, preferably to races 8, 9, 11, 13, 16 and 17, and conferring resistance when the gene is in homozygous form against at least 15 of the 17 officially denominated races (namely Pfs 1-9, Pfs11-14 and Pfs 16 and 17).

In one aspect of the invention, RPF15 confers dominant resistance to at least Pfs races 8, 9, 11, 13 and 16, preferably to at least Pfs 8, 9, 11, 13, 16 and 17, and further confers resistance to Pfs races 1, 2, 3, 4, 5, 6 and 7 at least when the gene (or introgression fragment comprising the gene) is in homozygous form and to Pfs races 12 and 14 at least when the gene (or introgression fragment comprising the gene) is in homozygous form.

In one aspect, the RPF15 gene is linked to the resistant donor nucleotide for SNP_01, which comprises an Adenine (A) at nucleotide 106 of SEQ ID NO: 1 or comprising an Adenine at the equivalent position in a sequence comprising at least 90%, preferably at least 91%, 92%, 93%, 94%, 95%, 96%, 97%, 98% or 99% sequence identity to SEQ ID NO: 1 and/or linked to the resistant donor nucleotide for SNP_02, which comprises a Cytosine (C) at nucleotide 184 of SEQ ID NO: 3, or comprises a Cytosine at the equivalent position in a sequence comprising at least 90%, preferably at least 91%, 92%, 93%, 94%, 95%, 96%, 97%, 98% or 99% sequence identity to SEQ ID NO: 3 (when aligned pairwise using e.g. the Emboss program Needle). Thus, in one aspect the spinach plant, or a part of said spinach plant, or a seed, or a cell, or a cell culture of spinach plant cells comprises in its genome a recombinant chromosome comprising an introgression fragment from a donor plant, said introgression fragment comprising the RPF15 gene which is linked to SNP_01, which comprises an Adenine at nucleotide 106 of SEQ ID NO: 1 or to a sequence comprising at least 90%, preferably at least 91%, 92%, 93%, 94%, 95%, 96%, 97%, 98% or 99% sequence identity to SEQ ID NO: 1 retaining the resistant donor SNP_01 nucleotide and/or linked to SNP_02, which comprises an Cytosine at nucleotide 184 of SEQ ID NO: 3 or to a sequence comprising at least 90%, preferably at least 91%, 92%, 93%, 94%, 95%, 96%, 97%, 98% or 99% sequence identity to SEQ ID NO: 3 retaining the resistant donor SNP_02 nucleotide. Since spinach is diploid, if the introgression fragment comprising SNP_01 and SNP_02 is present in homozygous form, the genotype of the plant at SNP_01, i.e. nucleotide 106 of SEQ ID NO: 1, is AA and the genotype of the plant at SNP_02, i.e. nucleotide 184 of SEQ ID NO: 3, is CC. If the introgression fragment comprising SNP_01 is present in heterozygous form, the genotype of the plant at SNP_01, i.e. nucleotide 106 of SEQ ID NO: 1, is AC, AG or AT, and if the introgression fragment comprising SNP_02 is present in heterozygous form, the genotype of the plant at SNP_02, i.e. nucleotide 184 of SEQ ID NO: 1, is CA, CG or CT.

In one aspect the introgression fragment comprising RPF15 comprises SEQ ID NO: 1, or a sequence comprising at least 90% sequence identity to SEQ ID NO: 1, with an Adenine at nucleotide 106 of SEQ ID NO: 1, or at the equivalent nucleotide when aligned pairwise using e.g. the Emboss program Needle and/or the introgression fragment comprises SEQ ID NO: 3, or a sequence comprising at least 90% sequence identity to SEQ ID NO: 3, with an Cytosine at nucleotide 184 of SEQ ID NO: 3, or at the equivalent nucleotide when aligned pairwise using e.g. the Emboss program Needle.

When referring herein to a SNP genotype at a specific position, e.g. at nucleotide 106 of SEQ ID NO: 1, or at nucleotide 184 of SEQ ID NO: 3, "or of a sequence comprising at least 90%, 91%, 92%, 93%, 94%, 95%, 96%, 97%, 98% or 99% sequence identity to the SEQ ID NO", this means that the SNP genotype is present in a variant sequence at a nucleotide equivalent to (corresponding to) the same nucleotide (e.g. equivalent to nucleotide 106 of SEQ ID NO: 1 or to nucleotide 184 of SEQ ID NO: 3) in the variant sequence, i.e. in a sequence comprising at least 90%, 91%, 92%, 93%, 94%, 95%, 96%, 97%, 98% or 99% sequence identity to the mentioned SEQ ID NO. It may for example be that the variant sequence is one or a few nucleotides shorter, but when one pairwise aligns the variant sequence with the mentioned SEQ ID NO, one can see which nucleotide of the variant sequence is equivalent to (corresponds to) the same nucleotide. In the variant sequence for SNP_01 this may for example be nucleotide number 105 or 107 of that variant sequence which is equivalent to nucleotide 106 of the mentioned sequence. In the variant sequence for SNP_02 this may for example be nucleotide number 183 or 185 or 190 of that variant sequence which is equivalent to nucleotide 184 of the mentioned sequence.

It is also an object of the invention to provide a cultivated spinach plant, or a part of said plant, or a seed thereof comprising an introgression fragment from a donor that is a wild relative of spinach, said fragment comprising the new resistance gene RPF15, which plants have thereby dominant resistance to at least Pfs races 8, 9, 11, 13 and 16, preferably to at least Pfs races 8, 9, 11, 13, 16 and 17. The cultivated spinach plant, or a part of said plant, or a seed thereof are resistant, at least when the RPF15 gene is present in homozygous form, to one or more of Pfs races 1 to 9, to Pfs 11 to 14, 16-17 and to Pfs isolate UA0514. Said fragment introgressed into the cultivated spinach plant comprises the resistant donor nucleotide for SNP_01, which is an Adenine (A) at nucleotide 106 of SEQ ID NO: 1 or an Adenine at the equivalent position of a sequence comprising at least 90%, preferably at least 91%, 92%, 93%, 94%, 95%, 96%, 97%, 98% or 99% sequence identity to SEQ ID NO: 1 and/or the resistant donor nucleotide for SNP_02, which is a Cytosine at nucleotide 184 of SEQ ID NO: 3 or a Cytosine at the equivalent position of a sequence comprising at least 90%, preferably at least 91%, 92%, 93%, 94%, 95%, 96%, 97%, 98% or 99% sequence identity to SEQ ID NO: 3.

Thus, in one aspect a spinach plant is provided comprising an introgression fragment from a donor that is a wild relative of spinach, especially *S. turkestanica*, wherein said introgression fragment comprises a gene, which confers resistance against at least *Peronospora farinosa* races 1 to 9, 11 to 14 and 16 and 17 when the gene is in homozygous form and the introgression fragment comprising an Adenine at nucleotide 106 (SNP_01) of SEQ ID NO: 1, whereby a spinach plant homozygous for the introgression fragment comprises the genotype 'AA' for SNP_01, and/or the introgression fragment comprises a Cytosine at nucleotide 184 (SNP_02) of SEQ ID NO: 3, whereby a spinach plant homozygous for the introgression fragment comprises the genotype 'CC' for SNP_02.

It is also an object of the invention to provide a cultivated spinach plant, or a part of said plant, or a seed that can be grown into such a plant, or a cell, or a cell culture of spinach cells, wherein said part or said cells can be regenerated into a plant, comprising the resistance gene RPF15, where said cultivated plant, or regenerated plant has dominant resistance to at least Pfs races 8, 9, 11, 13 and 16, preferably to races 8, 9, 11, 13, 16 and 17, and preferably comprises the resistant donor nucleotide for SNP_01, which is an Adenine (A) at nucleotide 106 of SEQ ID NO: 1 or an Adenine at the equivalent position of a sequence comprising at least 90%, preferably at least 91%, 92%, 93%, 94%, 95%, 96%, 97%, 98% or 99% sequence identity to SEQ ID NO: 1 and/or the resistant donor nucleotide for SNP_02, which is a Cytosine at nucleotide 184 of SEQ ID NO: 3 or Cytosine at the equivalent position of a sequence comprising at least 90%, preferably at least 91%, 92%, 93%, 94%, 95%, 96%, 97%, 98% or 99% sequence identity to SEQ ID NO: 3 (when aligned pairwise using e.g. the Emboss program Needle, using default parameters). The cultivated spinach plant, the plant part thereof or said seed are further resistant to Pfs races 1 to 7, 12 and 14, or in yet a further option, to Pfs isolate UA0514 and/or to other Pfs isolates at least when the RPF15 gene (or the introgression fragment comprising the gene) is in homozygous form.

In a further object, the invention provides a method for generating a cultivated spinach plant comprising resistance to at least Pfs races 8, 9, 11, 13 and 16 and 17 and further resistance to Pfs races 1 to 7, 12 and 14, at least when the RPF15 gene is in homozygous form, and to Pfs isolate UA0514 and/or to other Pfs isolates, wherein the plant comprises the resistant donor nucleotide for SNP_01, which is an Adenine (A) at nucleotide 106 of SEQ ID NO: 1, or an Adenine at the equivalent position of a sequence comprising at least 90%, preferably at least 91%, 92%, 93%, 94%, 95%, 96%, 97%, 98% or 99% sequence identity to SEQ ID NO: 1 and/or the resistant donor nucleotide for SNP_02, which is a Cytosine at nucleotide 184 of SEQ ID NO: 3 or a Cytosine at the equivalent position of a sequence comprising at least 90%, preferably at least 91%, 92%, 93%, 94%, 95%, 96%, 97%, 98% or 99% sequence identity to SEQ ID NO: 3 (when aligned pairwise using e.g. the Emboss program Needle, using default parameters).

Thus, one aspect provides a cultivated spinach plant comprising an introgression fragment from a donor that is a wild relative of spinach, wherein said introgression fragment comprises a single gene, which confers resistance in heterozygous and homozygous form, against at least *Peronospora farinosa* races 8, 9, 11, 13 and 16 and 17, and said gene is linked to SEQ ID NO: 1 comprising an Adenine at nucleotide 106 (SNP_01), or to a sequence comprising at least 90% sequence identity to SEQ ID NO: 1 and comprising an Adenine at the nucleotide position equivalent to nucleotide 106 of SEQ ID NO: 1 an/or linked to SEQ ID NO: 3 comprising Cytosine at nucleotide 184 (SNP_02), or to a sequence comprising at least 90% sequence identity to SEQ ID NO: 3 and comprising a Cytosine at the nucleotide position equivalent to nucleotide 184 of SEQ ID NO: 3.

Also provided is a method for identifying or selecting a spinach plant, plant part or cell comprising an introgression fragment from a donor that is a wild relative of spinach, wherein said introgression fragment comprises a single gene, which confers resistance in heterozygous and homozygous form, against at least *Peronospora farinosa* races 8, 9, 11, 13 and 16, preferably races 8, 9, 11, 13, 16 and 17, said method comprising:

determining the presence of an Adenine at nucleotide 106 of SEQ ID NO: 1 (SNP_01), or of an Adenine at the nucleotide position equivalent to nucleotide 106 of SEQ ID NO: 1 in a sequence comprising at least 90%, preferably at least 91%, 92%, 93%, 94%, 95%, 96%, 97%, 98% or 99%, sequence identity to SEQ ID NO: 1, and/or determining the presence of a Cytosine at nucleotide 184 of SEQ ID NO: 3 (SNP_02), or of an Cytosine at the nucleotide position equivalent to nucleotide 184 of SEQ ID NO: 3 in a sequence comprising at least 90%, preferably at least 91%, 92%, 93%, 94%, 95%, 96%, 97%, 98% or 99%, sequence identity to SEQ ID NO: 3.

The method may further comprise testing the resistance phenotype against one or more of the Pfs races mentioned herein as being conferred by the RPF15 gene.

The presence of an Adenine at nucleotide 106 of SEQ ID NO: 1 or at the equivalent nucleotide of a variant sequence, and the presence of a Cytosine at nucleotide 184 of SEQ ID NO: 3 or at the equivalent nucleotide of a variant sequence (e.g. position 190) can be determined by various methods known in the art, such as SNP genotyping methods, sequencing, etc.

Also, the invention provides a cultivated spinach plant, a plant part thereof, or a seed that can be grown into such a plant, as well as a cell or a cell culture comprising the resistance gene RPF15 wherein said gene is the gene as present in, or obtainable from or derivable from, cultivated spinach seeds deposited under accession number NCIMB 42608 or progeny derived from said seed.

Thus, in one aspect a spinach plant is provided comprising an introgression fragment from a donor that is a wild relative of spinach, especially *S. turkestanica*, wherein said introgression fragment comprises a gene, which confers resistance against at least *Peronospora farinosa* races 8, 9, 11, 13, 16, preferably races 8, 9, 11, 13, 16 and 17, when the gene is in heterozygous form and against races 1 to 9, 11 to 14, 16 and 17 when the gene is in homozygous form, and the introgression fragment comprising an Adenine at nucleotide 106 (SNP_01) of SEQ ID NO: 1 and/or a Cytosine at nucleotide 184 of SEQ ID NO: 3, wherein said gene is the gene present in plants grown from seeds, a representative sample of which has been deposited under accession number NCIMB 42608.

Provided is a spinach plant of the species *Spinacia oleracea* comprising resistance against *Peronospora farinose* races 8, 9, 11, 13, 16, preferably races 8, 9, 11, 13, 16 and 17, wherein said resistance is conferred by an introgression fragment comprising a single gene, said introgression fragment comprises an Adenine for SNP_01 at nucleotide 106 of SEQ ID NO: 1 and/or a Cytosine at nucleotide 184 of SEQ ID NO: 3, wherein said gene is the gene present in plants grown from seeds, a representative sample of which has been deposited under accession number NCIMB 42608.

Also a progeny plant of said spinach plant is provided, wherein said progeny plant retains the introgression fragment comprising the resistance gene and comprising an Adenine for SNP_01 at nucleotide 106 of SEQ ID NO: 1 and/or an Cytosine for SNP_02 at nucleotide 184 of SEQ ID NO: 3, which gene confers resistance against *Peronospora farinosa* races 8, 9, 11, 13, 16, preferably races 8, 9, 11, 13, 16 and 17, when the gene is in heterozygous form.

Further, the invention provides a cultivated spinach plant, a plant part thereof or a seed that can be grown into such a plant, as well as a cell or a cell culture comprising an introgression fragment from a donor that is a wild relative of spinach, said fragment comprising the resistance gene RPF15 wherein said introgression fragment is the fragment as present in, or obtainable from or derivable from, cultivated spinach seeds deposited under accession number NCIMB 42608, or comprising a sub-fragment of said introgression fragment retaining RPF15. In one aspect, said introgression fragment or sub-fragment comprises the resistant donor nucleotide for SNP_01, which comprises an Adenine (A) at nucleotide 106 of SEQ ID NO: 1, or comprises an Adenine at the equivalent position of a sequence comprising at least 90%, preferably at least 91%, 92%, 93%, 94%, 95%, 96%, 97%, 98% or 99% sequence identity to SEQ ID NO: 1 and/or said introgression fragment or sub-fragment comprises the resistant donor nucleotide SNP_02, which comprises a Cytosine (C) at nucleotide 184 of SEQ ID NO: 3 or comprises a Cytosine at the equivalent position of a sequence comprising at least 90%, preferably at least 91%, 92%, 93%, 94%, 95%, 96%, 97%, 98% or 99% sequence identity to SEQ ID NO: 3 (when aligned pairwise using e.g. the Emboss program Needle).

The invention also provides methods for generating or identifying a cultivated spinach plant, or a seed, a plant part or a cell or a cell culture thereof comprising resistance to at least Pfs races 8, 9, 11, 13 and 16, preferably to at least races 8, 9, 11, 13, 16 and 17, and further resistance to one or more of Pfs races 1 to 7, 12 and 14, and to Pfs isolate UA0514, at least when the resistance gene is in homozygous form. The invention furthermore provides methods for identification, selection, or detection of the RPF15 gene or the introgression fragment comprising the RPF15 gene, optionally using the resistant donor nucleotide for SNP_01, which comprises an Adenine (A) at nucleotide 106 of SEQ ID NO: 1 or comprising an Adenine at the equivalent position in a sequence comprising at least 90%, preferably at least 91%, 92%, 93%, 94%, 95%, 96%, 97%, 98% or 99% sequence identity to SEQ ID NO: 1 and/or using the resistant donor nucleotide for SNP_02, which comprises an Cytosine (C) at nucleotide 184 of SEQ ID NO: 3 or comprises Cytosine at the equivalent position in a sequence comprising at least 90%, preferably at least 91%, 92%, 93%, 94%, 95%, 96%, 97%, 98% or 99% sequence identity to SEQ ID NO: 3 (when aligned pairwise using e.g. the Emboss program Needle).

In an aspect of the invention, the resistance gene RPF15 is linked to the resistant donor nucleotide of SNP_01, which comprises an Adenine (A) at nucleotide 106 of SEQ ID NO: 1 or an Adenine at the equivalent position in a sequence having at least 90%, preferably at least 91%, 92%, 93%, 94%, 95%, 96%, 97%, 98% or 99% sequence identity to SEQ ID NO: 1 and/or is linked to the resistant donor nucleotide for SNP_02, which comprises an Cytosine (C) at nucleotide 184 of SEQ ID NO: 3 or Cytosine at the equivalent position in a sequence comprising at least 90%, preferably at least 91%, 92%, 93%, 94%, 95%, 96%, 97%, 98% or 99% sequence identity to SEQ ID NO: 3.

In one aspect, the resistance gene RPF15 is located on an introgression fragment, or a part of such a fragment, on a recombinant chromosome. In one embodiment, the introgression fragment is on chromosome 3 of the spinach genome, wherein chromosome 3 is the chromosome as found in the database SpinachBase and described in Xu et at (2017, supra). SNP_01 is located at nucleotide 1090954 of chromosome 3 in the database. SNP_02 is located at nucleotide 607751 of chromosome 3 in the database. In this the sequence of a Chinese cultivated spinach variety, not comprising an introgression fragment comprising RPF15, SNP_01 has an Adenine at nucleotide 1090954 of chromosome 3 and SNP_02 has a Cytosine at nucleotide 607751 of chromosome 3. In one aspect the RPF15 gene is located on chromosome 3 between SNP_02, at nucleotide 607751 (0.6 Mb), and nucleotide 1219930 (1.2 Mb) of chromosome 3. The chromosome 3 region in which the RPF15 gene is found is thus relatively small (0.6 Mb region). Sequencing or fine mapping can further narrow down the region and Crispr/Cas gene editing of the genes found in the region can be used to show which of the genes introgressed from the wild donor present in the region is responsible for the resistance phenotype. In another aspect the RPF15 gene is located in between SNP_01 and SNP_02, meaning that the SNP markers are located on different sides of the gene. It is noted that reference herein to a 'single gene' means that segregation of resistance was found to have the segregation ratio of a single gene or locus (see examples). It does not exclude that there may be several tightly linked genes on the introgression fragment which segregate as a 'single gene' or locus.

Thus, in an aspect of the invention the cultivated spinach plant or seed that can be grown into such a plant or plant part or the cultivated spinach cell/cell culture comprises an introgression fragment from a wild relative of spinach, wherein said fragment comprises RPF15, and preferably comprises the wild donor SNP nucleotide for SNP_01 and/or for SNP_3. The DNA fragment comprising RPF15 is introgressed from a wild relative of spinach (donor of the resistance gene), in one preferred aspect the wild relative of spinach is *Spinacia turkestanica*. The gene has been introgressed into cultivated spinach (the recurrent parent). Thus, the invention provides a cultivated spinach plant, or a seed from which such a plant can grow, a plant part or a cell culture thereof, comprising an introgression fragment from said wild relative of spinach, wherein the introgression fragment comprises the RPF15 gene and optionally the resistant donor nucleotide SNP_01, which comprises Adenine (A) at nucleotide 106 of SEQ ID NO: 1, or an Adenine at the equivalent position of a sequence comprising at least 90%, preferably at least 91%, 92%, 93%, 94%, 95%, 96%, 97%, 98% or 99% sequence identity to SEQ ID NO:

1 and/or the resistant donor nucleotide SNP_02, which comprises Cytosine (C) at nucleotide 184 of SEQ ID NO: 3, or a Cytosine at the equivalent position of a sequence comprising at least 90%, preferably at least 91%, 92%, 93%, 94%, 95%, 96%, 97%, 98% or 99% sequence identity to SEQ ID NO: 3.

In one aspect of the invention, a plant of the invention is heterozygous for the introgression fragment and comprises one chromosome that has nucleotide A at position 106 of SEQ ID NO: 1, or at the equivalent position in a sequence comprising at least 90%, preferably at least 91%, 92%, 93%, 94%, 95%, 96%, 97%, 98% or 99% sequence identity to SEQ ID NO: 1 and/or nucleotide C at position 184 of SEQ ID NO: 3, or at the equivalent position in a sequence comprising at least 90%, preferably at least 91%, 92%, 93%, 94%, 95%, 96%, 97%, 98% or 99% sequence identity to SEQ ID NO: 3. In yet another aspect of the invention, a plant of the invention is homozygous for the introgression fragment and comprises two chromosomes that have nucleotide A at position 106 of SEQ ID NO: 1, or at the equivalent position in a sequence comprising at least 90%, preferably at least 91%, 92%, 93%, 94%, 95%, 96%, 97%, 98% or 99% sequence identity to SEQ ID NO: 1 and/or nucleotide C at position 184 of SEQ ID NO: 3, or at the equivalent position in a sequence comprising at least 90%, preferably at least 91%, 92%, 93%, 94%, 95%, 96%, 97%, 98% or 99% sequence identity to SEQ ID NO: 3. Preferably the two chromosomes have the same introgression fragment, i.e. the nucleotide sequence of the introgression fragment and the size and location of the fragment are the same.

It is a further object to provide one or more DNA markers that can be used in the selection of plants or plant parts or cells comprising the RPF15 resistance gene. One marker provided herein is the resistant donor nucleotide SNP_01 which comprises Adenine (A) at nucleotide 106 of SEQ ID NO: 1, or A at the equivalent position of a sequence comprising at least 90%, preferably at least 91%, 92%, 93%, 94%, 95%, 96%, 97%, 98% or 99% sequence identity to SEQ ID NO: 1 and/or the resistant donor nucleotide SNP_02, which comprises Cytosine (C) at nucleotide 184 of SEQ ID NO: 3, or C at the equivalent position of a sequence comprising at least 90%, preferably at least 91%, 92%, 93%, 94%, 95%, 96%, 97%, 98% or 99% sequence identity to SEQ ID NO: 3. Other DNA markers linked to the RPF15 gene and/or to the introgression fragment can be developed by the skilled person, e.g. by sequencing the chromosome 3 region comprising the introgression fragment, as e.g. present in NCIMB 42608, in order to identify the S. turkestanica fragment of the donor. Any polymorphism between the S. turkestanica fragment and S. oleracea can, for example, be used as a marker to select or identify the introgression fragment comprising RPF15.

By sequencing the genome of the deposited seed, the introgression fragment of the single, specific S. turkestanica donor plant/accession (having a specific nucleotide sequence, which is polymorphic and different from the S. oleracea sequence which it replaces on chromosome 3 and which is also different from other S. turkestanica plants/accessions) can be identified by the skilled person. Also the introgression fragment can be used to distinguish a plant of the invention from any other spinach plant, even if the spinach plant has the same resistance phenotype. For example, the single, specific donor plants used herein, comprising RPF15 and having the nucleotide sequence as in the deposited seeds NCIMB42608, is a different donor plant than the donor plant used to generate NCIMB 42607 (comprising RPF14), NCIMB 42159 (comprising RPF12), NCIMB 42158 (comprising RPF11). Thus, not only are the resistance genes different, but each introgression fragment is also unique in its size, the region of the chromosome and the nucleotide sequence.

Also, methods for either generating or for identifying plants or plant parts or cells comprising said resistance gene are provided. In some aspects, methods for selecting, identifying, and/or detecting the resistance gene, designated RPF15, or a DNA marker linked to the gene, such as SNP_01 or SEQ ID NO:1 or SNP_02 or SEQ ID NO:3, comprise e.g. hybridizing one or more nucleic acid probes (e.g. hybridizing to SEQ ID NO: 1 or SEQ ID NO:3, or to a sequence comprising at least 90%, preferably at least 91%, 92%, 93%, 94%, 95%, 96%, 97%, 98% or 99% sequence identity to SEQ ID NO: 1 and comprising an Adenine at nucleotide 106 of SEQ ID NO: 1 or an equivalent position or to a sequence comprising at least 90%, preferably at least 91%, 92%, 93%, 94%, 95%, 96%, 97%, 98% or 99% sequence identity to SEQ ID NO: 3 and comprising an Cytosine at nucleotide 184 of SEQ ID NO: 1 or an equivalent position) to a nucleic acid of a plant suspected of comprising RPF15, or amplifying a nucleic acid of a plant suspected of comprising RPF15 using one or more nucleic acid primers, are provided. Primers can for example be made to detect SNP_01 or SNP_02 and to determine the SNP genotype of SNP_01 or SNP_02.

RPF15 is introgressed from a wild relative of spinach (the donor or resistance gene donor) into cultivated spinach (also referred to as the recurrent parent or recipient), preferably from S turkestanica. In one aspect, a cultivated spinach plant or plant part is provided comprising an introgression fragment from a wild relative of spinach, wherein the introgression fragment comprises the RPF15 gene, and optionally wherein the RPF15 gene is linked to the resistant donor nucleotide of SNP_01, which comprises an Adenine (A) at nucleotide 106 of SEQ ID NO: 1 or an Adenine at the equivalent position in a sequence having at least 90%, preferably at least 91%, 92%, 93%, 94%, 95%, 96%, 97%, 98% or 99% sequence identity to SEQ ID NO: 1 and/or linked to the resistant donor nucleotide for SNP_02, which comprises an Cytosine (C) at nucleotide 184 of SEQ ID NO: 3 or C at the equivalent position in a sequence comprising at least 90%, preferably at least 91%, 92%, 93%, 94%, 95%, 96%, 97%, 98% or 99% sequence identity to SEQ ID NO: 3.

Also provided is the use of the gene and/or the use of molecular markers (especially Single Nucleotide Polymorphisms or SNPs, more especially resistant donor nucleotide SNP_01, which comprises an Adenine (A) at nucleotide 106 of SEQ ID NO: 1 or A at the equivalent position in a sequence having at least 90%, preferably at least 91%, 92%, 93%, 94%, 95%, 96%, 97%, 98% or 99% sequence identity to SEQ ID NO: 1 and/or SNP_02, which comprises a Cytosine (C) at nucleotide 184 of SEQ ID NO: 3 or C at the equivalent position in a sequence having at least 90%, preferably at least 91%, 92%, 93%, 94%, 95%, 96%, 97%, 98% or 99% sequence identity to SEQ ID NO: 3) physically linked to the gene for the identification of a plant or a plant part or a seed or a cell, or a cell culture comprising RPF15, and methods of using such markers in identifying or generating a plant or a plant part or a seed or a cell, or a cell culture comprising RPF15.

In one aspect, the cultivated spinach comprises a recombinant chromosome, especially a recombinant chromosome 3 (as referred to by Xu et al., 2017, supra), said chromosome 3 comprises the introgression fragment which, in turn, comprises RPF15 and optionally in one aspect the introgression fragment comprises the resistant donor nucleotide for SNP_01 (i.e. an Adenine at nucleotide 106 of SEQ ID NO: 1, or A at the equivalent position in a sequence having at least 90%, preferably at least 91%, 92%, 93%, 94%, 95%, 96%, 97%, 98% or 99% sequence identity to SEQ ID NO: 1) and/or comprises the resistant donor nucleotide for SNP_02 (i.e. a Cytosine at nucleotide 184 of SEQ ID NO: 3, or C at the equivalent position in a sequence having at least 90%, preferably at least 91%, 92%, 93%, 94%, 95%, 96%, 97%, 98% or 99% sequence identity to SEQ ID NO: 3). In a further aspect, the remaining chromosomes of said plant are cultivated spinach chromosomes. In one embodiment, the recombinant chromosome is chromosome 3 (as referred to by Xu et al., 2017, supra).

In one aspect the introgression fragment (comprising RPF15) is present on the upper part of chromosome 3 (as present in SpinachBase), wherein the upper part is 0 Mb to 2.0 Mb of chromosome 3. In one aspect RPF15 is located in a region starting at 0.4 Mb and ending at 1.5 Mb of chromosome 3. In one aspect the introgression fragment is equal to or less than 2 Mb in size and comprises the RPF15 gene. In one aspect the introgression fragment has the same nucleotide sequence and same size as the fragment present in seeds deposited under accession number NCIMB 42608 and comprises the RPF15 gene (conferring the resistance phenotype as described herein). In one aspect the introgression fragment has the same nucleotide sequence as the fragment present in seeds deposited under accession number NCIMB 42608 and comprises the RPF15 gene (conferring the resistance phenotype as described herein), but has a smaller size than the fragment found in the deposited seeds. So for example a part of the full size fragment may have been removed by recombination, e.g. on either side of the RPF15 gene. In one aspect the introgression fragment comprises RPF15 and also SEQ ID NO: 1 and/or SEQ ID NO: 3.

In one aspect, the RPF15 gene and/or the introgression fragment and/or the recombinant chromosome is the gene and/or introgression fragment and/or recombinant chromosome present in the seed deposited under accession number NCIMB 42608, or in a plant grown from said seed, or in a progeny thereof which retains the RPF15 gene in its genome, such as a progeny which retains the RPF15 gene, optionally linked to the resistant donor nucleotide of SNP_01, which comprises an Adenine (A) at nucleotide 106 of SEQ ID NO: 1 or an Adenine at the equivalent position in a sequence having at least 90%, preferably at least 91%, 92%, 93%, 94%, 95%, 96%, 97%, 98% or 99% sequence identity to SEQ ID NO: 1 and/or linked to the resistant donor nucleotide SNP_02, which comprises an Cytosine (C) at nucleotide 184 of SEQ ID NO: 3 or C at the equivalent position in a sequence comprising at least 90%, preferably at least 91%, 92%, 93%, 94%, 95%, 96%, 97%, 98% or 99% sequence identity to SEQ ID NO: 3. In one aspect, the progeny retains the SNP_01 nucleotide of the donor and/or the SNP_02 nucleotide of the donor, although the skilled person can also select a plant which retains the RPF15 gene but lacks SNP_01 of the donor or SNP_02 of the donor or both and thus comprises a shorter introgression fragment. Thus, in one aspect, the SNP nucleotide of SNP_01 and/or SNP_02 may also be the nucleotide of the recurrent parent, while the RPF15 gene is still present. The skilled person can sequence the introgression fragment present in the deposited seeds and/or present in progeny to determine whether the resistance phenotype of a plant is conferred by the RPF15 gene of the instant invention. The introgression fragment (and any sub-fragment thereof generated by recombination) is a specific genomic sequence derived from a specific donor and is therefore unique.

DEFINITIONS

All patent and non-patent documents cited herein are incorporated by reference in their entirety.

The indefinite article a or "an" does not exclude the possibility that more than one of the elements is present, unless the context clearly requires that there be one and only one of the elements. The indefinite article "a" or "an" thus usually means "at least one".

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two loci or genes (or phenotypic characteristics due to these specific loci or genes), but which can otherwise differ from one another enormously as regards the other loci or genes.

"Spinach" or "cultivated spinach" or "cultivated *Spinacia oleracea*" refers herein to plants of the species *Spinacia oleracea* (or seeds from which the plants can be grown), and parts of such plants, bred by humans for food and having good agronomic characteristics. This includes any cultivated spinach, such as breeding lines (e.g. backcross lines, inbred lines), cultivars and varieties (open pollinated or hybrids). This includes any type of spinach, such as savoy, flat- or smooth-leaf spinach or semi-savoy types. Wild spinach (i.e. not cultivated spinach) or wild relatives of spinach, such as *Spinacia tetrandra* and *Spinacia turkestanica*, are not encompassed by this definition.

"Wild relatives of spinach" comprises uncultivated plants of the family *Spinacia*, in particular *Spinacia tetrandra* and *Spinacia turkestanica*. These species are also referred to as the donor plants of the RPF15 gene and optionally DNA markers linked to the RPF15 gene, such as resistant donor nucleotide SNP_01, which comprises an Adenine (A) at nucleotide 106 of SEQ ID NO: 1 or an Adenine at the equivalent position in a sequence having at least 90%, preferably at least 91%, 92%, 93%, 94%, 95%, 96%, 97%, 98% or 99% sequence identity to SEQ ID NO: 1 and/or resistant donor nucleotide SNP_02, which comprises an Cytosine (C) at nucleotide 184 of SEQ ID NO: 3 or C at the equivalent position in a sequence comprising at least 90%, preferably at least 91%, 92%, 93%, 94%, 95%, 96%, 97%, 98% or 99% sequence identity to SEQ ID NO: 3; that is the fragment comprising the RPF15 gene, and optionally SNP_01 and/or SNP_02, is obtained or obtainable from said donor plant. "*Spinacia turkestanica*" is a wild relative of spinach, described in a.o. Acta Inst. Bot. Acad. Sc. URSS, Ser. I. Fasc. 2, 123 (1936). In one aspect of the invention, the donor plants of the RPF15 gene is a *Spinacia turkestanica* plant; in one aspect the introgression fragment is the fragment of the *S. turkestanica* donor accession as introgressed into NCIMB 42608, or a sub-fragment (smaller fragment generated e.g. by meiotic recombination) of that introgression fragment, which sub-fragment confers the RPF15 resistance phenotype and preferably comprises the resistant donor nucleotide for SNP_01 and/or SNP_02.

As used herein, the term "plant" includes the seed (from which the plant can be grown), the whole plant or any part such as a plant organ (e.g., a harvested or non-harvested leaf, etc.), a plant cell, a plant protoplast, a plant cell- or tissue culture from which a whole plant can be regenerated, a propagating or non-propagating plant cell, a plant cell which is not in a tissue culture (but which is, for example, In vivo in a plant or plant part), an isolated plant cell, plant callus, a protoplast, a microspore, a plant cell clump, a plant transplant, a seedling, a plant cell that is intact in a plant, a plant clone or micro-propagation, or a part of a plant (e.g., a harvested tissue or organ), such as a plant cutting, a vegetative propagation, a clonally propagated plant, a cotyledon, a hypocotyl, a leaf, a processed leaf, a stem, a stalk, a shoot, a bud, a root, a root tip, a petiole, a flower, a petal, a stamen, an anther, a stigma, a style, an ovary, a pollen grain, an ovule, an embryo, an embryo sac, a fruit, meristem, cambium, a seed (produced on the plant after self-fertilization or cross-fertilization), a part of a seed that is a maternal tissue, a graft, a scion, a rootstock, a part of any of these and the like, or a derivative thereof, preferably having the same genetic make-up (or very similar genetic make-up) as the plant from which it is obtained. Also any developmental stage is included, such as a seedling, a cutting prior or after rooting, a mature and/or immature plant or a mature and/or immature leaf. When "a seed of a plant" is referred to, these either refer to seeds from which the plant can be grown or to seeds produced on the plant, after self-fertilization or cross-fertilization.

"Tissue Culture" or "cell culture" refers to an in vitro composition comprising an isolated cell of the same or a different type or a collection of such cells organized into plant tissue. Tissue cultures and cell cultures of spinach, and regeneration of spinach plants therefrom, is well known and widely published (see, e.g. Nguyen et al, 2013, Plant Biotechnology Reports, Vol. 7 Issue 1, p99).

"Harvested plant material" refers herein to a plant part (e.g., a leaf detached from the whole plant) which has been collected for further storage and/or further use. A "harvested leaf" as used herein refers to a spinach leaf, i.e., the plant without the root system, for example substantially all (harvested) leaves. A harvested leaf may be processed. "A harvested seed" refers to a seed harvested from a line or variety, e.g., produced after self-fertilization or cross-fertilization and collected.

A "progeny" or "progenies" or "a descendant" as used herein refers to an offspring, or the first and/or all further descendants obtained from (obtainable from) a plant of the invention that comprises (retains) the RPF15 resistance gene in homozygous or heterozygous form and/or comprises the RPF15 resistance phenotype described herein. Progeny may be obtained by regeneration of a cell culture or tissue culture, or a part of a plant, or selfing of a plant, or by producing seed of a plant. In further embodiments, progeny may also encompass a spinach plant obtained from crossing of at least one spinach plant with another spinach plant of the same or another variety or (breeding) line, and/or backcrossing, and/or inserting of a locus into a plant and/or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above. Also doubled haploid plants are progeny.

"Plant line" is for example a breeding line which can be used to develop one or more varieties. An "inbred line" or "inbred parent" is a plant line developed by selfing a plant for several generations and can be used as a parent for an "F1 hybrid" (or single-cross hybrid made by crossing a male parent line with a female parent line). A "male breeding line" or "male parent" or "male parental line" is the male parent i.e. the pollen donor. A "female breeding line" or "female parent" or "female parental line" is the female parent i.e. the ovule donor. In spinach breeding, the female parent typically produces female flowers at least 3 weeks before male flowers. This prevents or strongly reduces presence of selfed female parental lines in F1 hybrid seed production.

An "elite spinach plant" is a plant, typically a hybrid having a genotype resulting into desirable agronomic traits which allow a grower to harvest a commercially desirable product. An "elite parental line" is an inbred parent, having a genotype resulting into desirable agronomic traits in its hybrid progeny. An "elite female parent" is furthermore a good seed producer.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"Hybrid" refers to the seeds harvested from crossing one plant line or variety with another plant line, and the plants or plant parts grown from said seeds.

"Crossing" refers to the mating of two parent plants. Equally "Cross-pollination" refers to fertilization by the union of two gametes from different plants.

"Selfing" refers to the self-pollination of a plant, i.e. to the union of gametes from the same plant.

The term "traditional breeding techniques" encompasses herein crossing, backcrossing, selfing, selection, chromosome doubling, double haploid production, embryo rescue, the use of bridge species, protoplast fusion, marker assisted selection, mutation breeding etc. as known to the breeder (i.e. methods other than genetic modification/transformation/transgenic methods), by which, for example, the RPF15-resistance gene can be obtained, identified, selected, and/or transferred.

"Backcrossing" refers to a breeding method by which a (single) trait, such as Pfs resistance conferred by the RPF15 resistance gene, can be transferred from one genetic background (also referred to as "donor"; generally but not necessarily this is an inferior genetic background) into another genetic background (also referred to as "recurrent parent" or "recipient"; generally but not necessarily this is a superior genetic background). An offspring of a cross (e.g. an F1 plant obtained by crossing a donor, e.g. a wild relative of spinach, with a recipient, e.g. a cultivated spinach line; or an F2 plant or F3 plant, etc., obtained from selfing the F1) is "backcrossed" to the parent with the superior genetic background (or recipient), e.g. to the cultivated parent. After repeated backcrossing, the trait of the donor genetic background, e.g. the RPF15gene, will have been incorporated into the recurrent genetic background. The terms "gene converted" or "conversion plant" or "single locus conversion" in this context refer to plants which are developed by backcrossing wherein essentially all of the desired morphological and/or physiological characteristics of the recurrent parent are recovered in addition to the one or more genes (e.g. the RPF15 resistance gene) transferred from the donor parent.

"Regeneration" refers to the development of a plant from in vitro cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting off) a leaf, a part of a leaf, a stem, a part of a stem, a stalk, a part of a stalk, a shoot, a part of a shoot, a bud or a part of a bud, a cutting, a root, a part of a root, a root tip, a petiole, a part of a petiole, a cotyledon, a part of a cotyledon, a flower, a part of a flower, a petal, a part of a petal, a stamen, a part of a stamen, an anther, a part of an anther, pollen, a stigma, a part of a stigma, a style, a part of a style, an ovary, a part of an ovary, an ovule, a part of an ovule, a seed, a part of a seed, a seed coat, an embryo, a part of an embryo, a hypocotyl, an embryo sac, a fruit, a part of a fruit, a cell, a protoplast, callus, a microspore, meristem, cambium. When a whole plant is regenerated by vegetative propagation, it is also referred to as a "vegetative propagation" or a "vegetatively propagated plant".

"Single locus converted (conversion) plant" refers to plants which are developed by plant breeding techniques comprising or consisting of backcrossing, wherein essentially all of the desired morphological and/or physiological characteristics of a spinach plant are recovered in addition to the characteristics of the single locus (e.g. the locus comprising the RPF15gene from the donor) having been transferred into the plant via the backcrossing technique and/or by genetic transformation.

"Transgene" or "chimeric gene" refers to a genetic locus comprising a DNA sequence which has been introduced into the genome of a spinach plant by transformation. A plant comprising a transgene stably integrated into its genome is referred to as "transgenic plant".

"Pfs" or "*Peronospora farinosa*" or "*P. effusa*" or "downy mildew" refers to races of the oomycete *Peronospora farinosa* f.sp. *spinaciae*. The definition comprises at least the officially recognized races and isolates. Pfs1-Pfs17 refer to the officially recognized races, which can be differentiated on the differential hosts of spinach which can be obtained from the Naktuinbouw, P.O. Box 40, 2370 AA Roelofarendsveen, The Netherlands, or via references provided by the ISF (International Seed Federation). The officially recognized pathogenic races are widespread. "Differential hosts" or "differentials" refers to the differential hosts of spinach for distinguishing Pfs races 1-17, which can be obtained from a.o. Naktuinbouw, P.O. Box 40, 2370 AA Roelofarendsveen, The Netherlands, or via references provided by the ISF (International Seed Federation). *Peronospora farinosa* f.sp. *spinaciae* race 16 was first identified in Salinas, Calif., USA (March 2015), and later found to be widespread. Its original designation was UA201519B, and it was "characterized based on disease development on a standard set of differential varieties." "Race Pfs: 16 is able to infect the differentials Viroflay, Resistoflay, Clermont, Lazio, Pigeon, and Meerkat, but not able to infect Califlay, Campania, Boeing (Avenger), Lion, Whale, and Caladonia." There are many other isolates which may become officially recognized races. An important isolate of *Peronospora farinosa* f.sp. *spinaciae* is UA0514.

A "Pfs resistant plant" or "downy mildew resistant plant" or a plant having "Pfs resistance" or a "Pfs resistant phenotype" refers to a spinach plant which is resistant against one or more pathogenic races (and pathogenic isolates) of Pfs, as e.g. determined in a qualitative resistance assay under controlled environmental conditions. In such a resistance assay a plurality of plants (e.g. at least 2 replicates of at least 10 plants) of a genotype, are inoculated with a sporangial suspension of the race or isolate and incubated under suitable conditions. After a suitable incubation period (e.g. 7, 8, 9, 10, 11 or more days after inoculation) the plants are evaluated for symptoms. Susceptible controls should show sporulation at the time of symptom evaluation. A plant showing sporulation on the cotyledons (and/or on the true leaf/leaves) is considered "susceptible", while a plant not showing any sporulation on the cotyledons (and/or on the true leaf/leaves) is considered "resistant". A plant genotype with more than 85% of the inoculated plants (preferably more than 90% or 95%) being classified as "resistant" plant is considered to a resistant against the race or isolate. In the test more than 85% of inoculated plants (preferably more than 90% or 95% of plants) of the susceptible control plant, such as cultivar Viroflay, should show sporulation. Suitable tests are described herein in the Examples, or in Irish et al. 2007 (Plant Disease Vol 91 No. 11, in Materials and Methods on page 1392-1394), or in Correll et al. 2010, "Guidelines for Spinach Downy Mildew: *Peronspora ferinosa* f.sp. *spinaciae* (Pfs)" found on the website of the ISF (International Seed Federation). As mentioned, against some races the resistance may be further sub-classified as 'intermediate resistance', indicating that the resistance level is somewhat different, as some plants may develop some minor symptoms. In the art, this is indicated by adding brackets around the symbol for resistance, i.e. "(-)".

"RPF15" refers herein to a single gene from a wild relative of spinach, which confers resistance (as defined above) to at least Pfs races 8, 9, 11, 13 and 16, preferably to races 8, 9, 11, 13, 16 and 17 (when the gene is in homozygous or in heterozygous form), and further confers resistance to Pfs races 1 to 7, (intermediate) resistance to races 12 and 14 and further to isolate UA0514 and/or other pathogenic isolates of Pfs (at least when the gene is in homozygous form, but possibly also when the gene is in heterozygous form). In one aspect of the invention, the resistance conferred by RPF15 in homozygous form is to Pfs races 1, 2, 3, 4, 5, 6, 7, 8, 9, 11, 12, 13, 14, 16 and 17. The resistance phenotype is also referred to herein as the "Pfs resistance phenotype conferred by the RPF15 gene". In a further aspect of the invention, RPF15 is located on an introgression fragment from a donor that is a wild relative of spinach, or on a part of an introgression fragment. In a yet another aspect of the invention, RPF15 is introgressed from a wild relative of spinach, in one aspect the wild relative of spinach is *S. turkestanica*. In a further aspect of the invention, RPF15 is located between a first DNA marker and a second DNA marker. In yet another aspect, RPF15 is physically linked to the resistant donor nucleotide of SNP_01, which is an Adenine (A) at nucleotide 106 of SEQ ID NO: 1 or an Adenine at the equivalent position in a sequence having at least 90%, preferably at least 91%, 92%, 93%, 94%, 95%, 96%, 97%, 98% or 99% sequence identity to SEQ ID NO: 1 and/or of resistant donor nucleotide SNP_02, which is a Cytosine (C) at nucleotide 184 of SEQ ID NO: 3 or C at the equivalent position in a sequence comprising at least 90%, preferably at least 91%, 92%, 93%, 94%, 95%, 96%, 97%, 98% or 99% sequence identity to SEQ ID NO: 3.

The term "locus" (loci plural) means a specific place or places or a site on a chromosome where for example a gene (e.g. the RPF15 gene) or genetic marker is found. In spinach according to the invention the resistance locus comprising the RPF15 gene is introgressed from a wild relative of spinach e.g. from a resistant accession of *S. turkestanica* (i.e. the donor plant) into cultivated spinach. The locus where the RPF15 gene is found is physically and genetically linked to the resistant donor nucleotide of SNP_01, which is an Adenine (A) at nucleotide 106 of SEQ ID NO: 1 or an Adenine at the equivalent position in a sequence having at least 90%, preferably at least 91%, 92%, 93%, 94%, 95%, 96%, 97%, 98% or 99% sequence identity to SEQ ID NO: 1 and/or of SNP_02, which is a Cytosine (C) at nucleotide 184 of SEQ ID NO: 3 or C at the equivalent position in a sequence comprising at least 90%, preferably at least 91%, 92%, 93%, 94%, 95%, 96%, 97%, 98% or 99% sequence identity to SEQ ID NO: 3.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "gene" means a (genomic) DNA sequence comprising a region (transcribed region), which is transcribed into a messenger RNA molecule (mRNA) in a cell, and an operably linked regulatory region (e.g. a promoter). Different alleles of a gene are thus different alternative forms of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

"Allelism test" refers to a genetic test whereby it can be tested whether two phenotypes, seen in two plants, are determined by the same gene or by different genes. For example, the plants to be tested are crossed with each other, the F1 is selfed and the segregation of the phenotypes amongst the F2 progeny is determined. The ratio of segregation indicates if the genes are allelic or not. See for example EP1816908B1, wherein an allelism test was used to show that the HMBN allele is not allelic to dw-1 and dw-2 alleles and is at a different locus.

"Introgression fragment" or "introgression segment" or "introgression region" refers to a chromosome fragment (or chromosome part or region) which has been introduced into another plant of the same or related species by crossing or traditional breeding techniques, such as backcrossing, i.e. the introgressed fragment is the result of breeding methods referred to by the verb "to introgress" (such as backcrossing). In spinach, wild relatives of spinach such as *Spinacia turkestanica* can be used to introgress fragments of the wild genome into the genome of cultivated spinach. Such a spinach plant thus has a "genome of *Spinacia oleracea*", but comprises in the genome a fragment of a wild relative of spinach, i.e. an introgression fragment of a donor plant. It is understood that the term "introgression fragment" never includes a whole chromosome, but only a part of a chromosome. The introgression fragment can be large, e.g. even half of a chromosome, but is preferably smaller, such as about 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2 Mb or less, about 1 Mb (equals 1,000,000 base pairs) or less, or about 0.7 Mb, 0.6 Mb, 0.5 Mb (equals 500,000 base pairs) or less, such as about 200,000 bp (equals 200 kilo base pairs) or less, about 100,000 bp (100 kb) or less, about 50,000 bp (50 kb) or less, about 25,000 bp (25 kb) or less. The skilled person may introgress such a fragment retaining a gene conferring a desired trait from a donor plant into a recipient plant. Sequencing of the whole genome of a plant comprising an introgression fragment will identify such an introgression fragment as being derived from a particular donor species and will allow to identify the specific donor, as the sequence is unique to a particular donor.

An "introgression fragment comprising the RPF15 resistance gene" or a "RPF15 introgression fragment" refers to part of a chromosome which is derived from the donor and comprises the RPF15 gene. In one aspect of the invention the introgression fragment further comprises one or more markers which are polymorphic between the donor and the cultivated spinach plant, which allow identification of the introgression fragment, such as SNP_01 or SNP_02. Thus, in one aspect the RPF15 gene is linked to the resistant donor nucleotide of SNP_01, which is an Adenine (A) at nucleotide 106 of SEQ ID NO: 1 or an Adenine at the equivalent position in a sequence having at least 90%, preferably at least 91%, 92%, 93%, 94%, 95%, 96%, 97%, 98% or 99% sequence identity to SEQ ID NO: 1 and/or to the resistant donor nucleotide of SNP_02, which is a Cytosine (C) at nucleotide 184 of SEQ ID NO: 3 or C at the equivalent position in a sequence comprising at least 90%, preferably at least 91%, 92%, 93%, 94%, 95%, 96%, 97%, 98% or 99% sequence identity to SEQ ID NO: 3.

"SNP_01 donor nucleotide" refers to the nucleotide Adenine found at the first SNP location, i.e. at nucleotide position 106 of SEQ ID NO: 1 or Adenine at the equivalent position of a sequence comprising at least 90%, preferably at least 91%, 92%, 93%, 94%, 95%, 96%, 97%, 98% or 99% sequence identity to SEQ ID NO: 1.

"SNP_02 donor nucleotide" refers to the nucleotide Cytosine found at the second SNP location, i.e. at nucleotide position 184 of SEQ ID NO: 3 or Cytosine at the equivalent position of a sequence comprising at least 90%, preferably at least 91%, 92%, 93%, 94%, 95%, 96%, 97%, 98% or 99% sequence identity to SEQ ID NO: 3.

"Sequence identity" can be determined by alignment of two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (defined further below). These programs use the Needleman and Wunsch global alignment algorithm to align two sequences over their entire length, maximizing the number of matches and minimizes the number of gaps. Generally, the default parameters are used, with a gap creation penalty=10 and gap extension penalty=0.5 (both for nucleotide and protein alignments). For nucleotides the default scoring matrix used is DNAFULL. Sequence alignments and scores for percentage sequence identity may for example be determined using computer programs, such as EMBOSS as available on the world wide web under ebi.ac.uk/Tools/psa/emboss_needle/). Alternatively sequence similarity or identity may be determined by searching against databases such as FASTA, BLAST®, etc., but hits should be retrieved and aligned pairwise to compare sequence identity. Two nucleic acid sequences have "substantial sequence identity" if the percentage sequence identity is at least 90%, 91%, 92%, 93%, 94%, 95%, 96%, 97%, 98%, 99% or more (as determined by Emboss "needle" using default parameters, i.e. gap creation penalty=10, gap extension penalty=0.5, using scoring matrix DNAFULL for nucleic acids).

"Physical distance" between loci (e.g. between molecular markers and/or between phenotypic markers) on the same chromosome is the actual physical distance expressed in base pairs (bp), kilo base pairs (kb) or megabase pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

A "molecular marker" is a piece of DNA associated with a certain genomic or chromosomal location or single nucleotide polymorphism (SNP), which is found on the chromosome close to the gene of interest, preferably close to RPF15. Molecular markers can be used to identify a particular sequence of DNA, or a certain location in a genome or on a chromosome, or to identify an introgression fragment. When reference is made herein to one or more molecular markers being "detectable" by a molecular marker assay, this means of course that the plant or plant part comprises the one or more markers in its genome, as the marker would otherwise not be detectable. In one aspect, the marker is a Single Nucleotide Polymorphism (SNP), but other molecular markers such as RFLP, AFLP, RAPD, INDEL, DNA sequencing, etc. may equally be used. In one aspect, an Adenine at nucleotide 106 of SEQ ID NO: 1 (the resistance donor nucleotide for SNP_01), or an Adenine at an equivalent position of a sequence comprising at least 90%, 91%, 92%, 93%, 94%, 95%, 96%, 97%, 98% or 99% sequence identity to SEQ ID NO: 1, is linked to the RPF15 gene and to the introgression fragment comprising the RPF15 gene, where said resistant donor nucleotide can be used to select plants, plant tissues or plant parts comprising the introgression fragment (comprising the RPF15 gene), and thus to select and/or generate resistant plants or plant parts (as defined above). In a further aspect, a Cytosine at nucleotide 184 of SEQ ID NO: 3 (the resistance donor nucleotide for SNP_01), or an Adenine at an equivalent position of a sequence comprising at least 90%, 91%, 92%, 93%, 94%, 95%, 96%, 97%, 98% or 99% sequence identity to SEQ ID NO: 3, is linked to the RPF15 gene and to the introgression fragment comprising the RPF15 gene, where said resistant donor nucleotide can be used to select plants, plant tissues or plant parts comprising the introgression fragment (comprising the RPF15 gene), and thus to select and/or generate resistant plants or plant parts (as defined above). Other SNPs which are polymorphic between the introgression fragment and cultivated spinach can be developed by the skilled person by e.g. sequencing or fine mapping.

"Flanking markers" are molecular markers located on the chromosome on either side of the RPF15 gene. Fine mapping or sequencing can be used to identify flanking markers. For example, SNP_01 and/or SNP_02 can be combined with another marker located on the other side of the RPF15 gene to form a set of flanking markers.

Other molecular markers can be developed which are linked to RPF15 and/or which are on the introgression fragment comprising the RPF15 gene, e.g. which are in between SNP_01 or SNP_02 and RPF15 or which flank the RPF15 locus or are physically linked to said locus. This can be done by e.g. fine-mapping the RPF15 gene or sequencing of the chromosome or chromosome region. Any of these markers can then be used for identification and/or selection of the introgression fragment comprising the RPF15 gene, conferring Pfs resistance (as defined above) against at least Pfs races 8, 9, 11, 13 and 16 (preferably at least races 8, 9, 11, 13, 16 and 17) when the gene is in homozygous or heterozygous form, For example, fine-mapping can be carried out to find markers which are linked even more closely to the RPF15 gene on the introgression fragment. Fine mapping involves making a population of recombinant plants (derived e.g. from crossing seeds deposited under accession number NCIMB 42608 with a susceptible plant, e.g. a susceptible line or variety), which comprise different recombination events of the chromosome on which the RPF15 gene is located and analyzing these recombinant plants (comprising e.g. different size subfragments of the introgression fragment) for the resistance phenotype conferred by the RPF15 gene and DNA markers. Thereby, the location of the RPF15 gene can be defined more precisely and markers which are linked more closely to the gene can be identified. In the same way, plants comprising an introgression fragment which is smaller (i.e. a sub-fragment) than the fragment found in seeds deposited under NCIMB accession number 42608 can be generated. Alternatively, sequencing can be carried out to identify markers closely linked to the RPF15gene or even within the gene.

The term "marker assay" or "genotyping assay" refers to an assay which can be used to determine the marker genotype, e.g. the SNP genotype. For example SNP markers can be detected using a KASP-assay (see world wide web at kpbioscience.co.uk) or other assays known to the skilled person.

"Marker assisted selection" or "MAS" or "Marker assisted breeding" or "MAB" is a process of using the presence of molecular markers, which are genetically and physically linked to a particular locus or to a particular chromosome region (e.g. introgression fragment), to select plants (e.g. progeny) for the presence of the specific locus or region (e.g. introgression fragment). For example the resistant donor nucleotide of SNP_01, which is an Adenine (A) at nucleotide 106 of SEQ ID NO: 1 or A at the equivalent position in a sequence having at least 90%, 91%, 92%, 93%, 94%, 95%, 96%, 97%, 98% or 99% sequence identity to SEQ ID NO: 1, or the resistant donor nucleotide of SNP_02, which is an Cytosine (C) at nucleotide 184 of SEQ ID NO: 3 or C at the equivalent position in a sequence having at least 90%, 91%, 92%, 93%, 94%, 95%, 96%, 97%, 98% or 99% sequence identity to SEQ ID NO: 3, or any marker near the RPF15 gene, may be used in MAS to select spinach plants or plant parts comprising the RPF15gene.

When reference is made to a nucleic acid sequence (e.g. DNA or genomic DNA) having "substantial sequence identity to" a reference sequence or having a sequence identity of at least 80%, e.g. at least 90%, 91%, 92%, 93%, 94%, 95%, 96%, 97%, 98% or 99% nucleic acid sequence identity to a reference sequence, in one embodiment said nucleotide sequence is considered substantially identical to the given nucleotide sequence and can be identified using stringent hybridisation conditions. In another embodiment, the nucleic acid sequence comprises one or more nucleotides replaced, inserted or deleted compared to the given nucleotide sequence but still can be identified using stringent hybridisation conditions.

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

Brief Description of Sequences

SEQ ID NO: 1 depicts the *S. turkestanica* sequence comprising an Adenine (A) for SNP_01 at nucleotide 106 of SEQ ID NO: 1. SEQ ID NO: 1 is present in seed deposited under accession number NCIMB 42608.

SEQ ID NO: 2 depicts the S *oleracea* (recurrent parent) sequence for SNP_01, comprising a Guanine (G) at nucleotide 106 of SEQ ID NO: 2.

SEQ ID NO: 3 depicts the *S. turkestanica* sequence comprising an Cytosine (C) for SNP_02 at nucleotide 184 of SEQ ID NO: 3. SEQ ID NO: 3 is present in seed deposited under accession number NCIMB 42608.

SEQ ID NO: 4 depicts the S *oleracea* (recurrent parent) sequence for SNP_01, comprising a Guanine (G) at nucleotide 184 of SEQ ID NO: 4.

SEQ ID NO: 5 depicts one of the flanking sequences from *S. tetrandra*, flanking the Downy Mildew QTL described in WO2015054339 (corresponding to SEQ ID NO: 1 in WO2015054339).

SEQ ID NO: 6 depicts the other flanking sequences from *S. tetrandra*, flanking the Downy Mildew QTL described in WO2015054339 (corresponding to SEQ ID NO: 2 in WO2015054339).

SEQ ID NO: 7 depicts the *S. oleracea* sequence in the region corresponding to SEQ ID NO: 5, as present seed of the invention, a representative sample having been deposited under number NCIMB 42608.

SEQ ID NO: 8 depicts the *S. oleracea* sequence in the region corresponding to SEQ ID NO: 6, as present seed of the invention, a representative sample having been deposited under number NCIMB 42608.

SEQ ID NO: 9 depicts the Spinachbase sequence of FIG. 1.

SEQ ID NO: 10 depicts the Spinachbase sequence of FIG. 2.

BRIEF DESCRIPTION OF FIGURES

FIG. 1 depicts the alignment of the SpinachBase reference genome sequence with SEQ ID NO: 1 (lower). The Adenine at nucleotide 106 of SEQ ID NO: 1 (SNP_01) and the Adenine at the equivalent position of the reference genome are in bold. It is noted that SNP_01 is not polymorphic with the sequence of the Chinese line of SpinachBase, but is polymorphic compared to the susceptible recurrent parent used by the inventors.

FIG. 2 depicts the alignment of the SpinachBase reference genome sequence with SEQ ID NO: 3 (lower). The Cytosine at nucleotide 184 of SEQ ID NO: 3 (SNP_02) and the Guanine at the equivalent position of the reference genome are in bold.

FIG. 3 depicts the alignment of SEQ ID NO: 5 (upper) with SEQ ID NO: 7 (lower).

FIG. 4 depicts the alignment of SEQ ID NO: 6 (upper) with SEQ ID NO: 8 (lower).

DETAILED DESCRIPTION OF THE INVENTION

Plants and Methods of the Invention

In one embodiment, the invention provides a cultivated spinach plant having resistance against at least *Peronospora farinosa* races 8, 9, 11, 13 and 16, preferably against at least races 8, 9, 11, 13, 16 and 17, where the resistance is conferred by a single dominant gene.

The single gene is designated RPF15, for Resistance to *Peronospora farinosa* gene 15. Thus the invention provides RPF15 which confers dominant resistance against *Peronospora farinosa* races 8, 9, 11, 13 and 16, preferably against races 8, 9, 11, 13, 16 and 17. In another embodiment, RPF15 further confers resistance against *Peronospora farinosa* races 1 to 7, at least when the RPF15 gene is in homozygous form and at least intermediate resistance against races 12 and 14, at least when the RPF15 gene is in homozygous form. In a further aspect of the invention, RPF15 confers resistance to isolate UA0514 and/or potentially other pathogenic isolates of *Peronospora farinosa*. These other isolates potentially comprise future isolates which develop in the field. The gene does not confer resistance to races 10 and 15. The RPF15 gene was identified in *Spinacia turkestanica* and was introduced through backcrossing into *Spinacia oleracea*, preferably cultivated spinach. The RPF15 gene is a single gene. The gene inherits dominantly for at least the resistance to Pfs races 8, 9, 11, 13 and 16, preferably to races 8, 9, 11, 13, 16 and 17; that is, when a plant comprising RPF15 in homozygous form is crossed with a susceptible plant, such as variety Viroflay, the F1 progeny will all show resistance to at least Pfs races 8, 9, 11, 13 and 16, preferably to races 8, 9, 11, 13, 16 and 17, and in the F2 progeny said resistance will segregate in a 3 (resistant): 1 (susceptible) ratio. The RPF15 gene is present in homozygous form in seed deposited under accession number NCIMB 42608, i.e. the introgression fragment comprising RPF15 is present in homozygous form. The RPF15 gene is linked to the resistant donor nucleotide SNP_01, which comprises an Adenine at nucleotide 106 of SEQ ID NO: 1 or Adenine at the equivalent position in a sequence having at least 90%, preferably at least 91%, 92%, 93%, 94%, 95%, 96%, 97%, 98% or 99% sequence identity to SEQ ID NO: 1 and/or the resistant donor nucleotide SNP_02, which comprises an Cytosine at nucleotide 184 of SEQ ID NO: 3 or Adenine at the equivalent position in a sequence having at least 90%, preferably at least 91%, 92%, 93%, 94%, 95%, 96%, 97%, 98% or 99% sequence identity to SEQ ID NO: 3. Thus, the introgression fragment present in the deposited seeds comprises SEQ ID NO:1 and SEQ ID NO: 3, i.e. comprises an Adenine at nucleotide 106 of SEQ ID NO: 1, as well as a Cytosine at nucleotide 184 of SEQ ID NO: 3, and both the Adenine (and the SEQ ID NO:1) as well as the Cytosine (and the SEQ ID NO:3) are present in homozygous form in the deposited seeds (the SNP_01 genotype of the deposited seeds is 'AA' and the SNP_02 genotype of the deposited seeds is 'CC').

In an aspect of the invention the RPF15 gene from *S. turkestanica* confers resistance against at least Pfs races 8, 9, 11, 13 and 16, preferably to races 8, 9, 11, 13, 16 and 17, when the gene is in homozygous or in heterozygous form in the genome of a cultivated spinach plant of the species *S. oleracea*.

The RPF15 gene from *S. turkestanica* does not confer resistance against Pfs races 10 and 15.

In a further aspect of the invention the RPF15 gene from *S. turkestanica* confers resistance against at least Pfs races 7, 8, 9, 11, 13 and 16 and 17, or at least races 6, 7, 8, 9, 11, 13 and 16 and 17, or at least races 1 to 9, 11, 13 and 16 and 17, and also resistance (at least intermediate resistance) against races 12 and 14, at least when the gene is in homozygous form, and to several of those races also in heterozygous form, in the genome of a cultivated spinach plant of the species *S. oleracea*.

In another aspect of the invention RPF15 confers resistance to at least races 8, 9, 11, 13, 16 and 17 and further to races 1 to 7, 12 and 14, at least when RPF15 (or the introgression fragment comprising RPF15) is in homozygous form, and to several of those races also when the gene (or the introgression fragment comprising the gene) is in heterozygous form, in the genome of a cultivated spinach plant.

In further aspects of the invention RPF15 confers resistance to resistance to at least races 8, 9, 11, 13 and 16, preferably to races 8, 9, 11, 13, 16 and 17 (when in homozygous or heterozygous form) and further to Pfs race 1 when RPF15 (or the introgression fragment comprising RPF15) is in homozygous or in heterozygous form, and/or to Pfs race 2 when RPF15 (or the introgression fragment comprising RPF15) is in homozygous or in heterozygous form, and/or to Pfs race 3 when RPF15 (or the introgression fragment comprising RPF15) is in homozygous or in heterozygous form, and/or to Pfs race 4 when RPF15 (or the introgression fragment comprising RPF15) is in homozygous or in heterozygous form and/or to Pfs race 5 when RPF15 (or the introgression fragment comprising RPF15) is in homozygous or in heterozygous form and/or to Pfs race 6 when RPF15 (or the introgression fragment comprising RPF15) is in homozygous or in heterozygous form and/or to Pfs race 7 when RPF15 (or the introgression fragment comprising RPF15) is in homozygous or in heterozygous form in the genome of a cultivated spinach plant. In yet a further aspect of the invention RPF15 confers resistance to race 12 and/or 14 and/or to isolate UA0514 and/or another pathogenic Pfs isolate when RPF15 (or the introgression fragment comprising RPF15) is in homozygous or in heterozygous form in the genome of a cultivated spinach plant.

In a further aspect of the invention, RPF15 introgression confers dominant resistance to at least Pfs races 8, 9, 11, 13 and 16, preferably to races 8, 9, 11, 13, 16 and 17, in a cultivated spinach plant, wherein the RPF15 gene (or the introgression fragment comprising the gene) is linked to (comprises) the resistant donor nucleotide of SNP_01, which is an Adenine (A) at nucleotide 106 of SEQ ID NO: 1 or A at the equivalent position in a sequence having at least 90%, preferably at least 91%, 92%, 93%, 94%, 95%, 96%, 97%, 98% or 99% sequence identity to SEQ ID NO: 1 and/or the resistant donor nucleotide of SNP_02, which is a Cytosine (C) at nucleotide 184 of SEQ ID NO: 3 or C at the equivalent position in a sequence having at least 90%, preferably at least 91%, 92%, 93%, 94%, 95%, 96%, 97%, 98% or 99% sequence identity to SEQ ID NO: 3. Resistance against these races is conferred when the introgression fragment is in homozygous form or in heterozygous form, as the resistance is dominant. For the resistance against the other races, i.e. races 1 to 7, 12 and 14, and UA0514 it is not clear if the resistance is only seen when the RPF15 gene is in homozygous form or if it is also seen (for one or more of these races) when the RPF15 gene is in heterozygous form; this is depending on whether resistance against a race is dominant or recessive. Whether resistance against a race is dominant or recessive can be tested in a resistance assay in e.g. plants heterozygous for RPF15 and/or segregating for RPF15.

In yet a further aspect of the invention, RPF15 introgression fragment confers resistance to at least Pfs races 1, 2, 3, 4, 5, 6, 7, 8, 9, 11, 12, 13, 14, 16 and 17 in a cultivated spinach plant, wherein the RPF15 gene (or the introgression fragment comprising the gene) is linked to (comprises) the resistant donor nucleotide of SNP_01, which is an Adenine (A) at nucleotide 106 of SEQ ID NO: 1 or A at the equivalent position in a sequence having at least 90%, preferably at least 91%, 92%, 93%, 94%, 95%, 96%, 97%, 98% or 99% sequence identity to SEQ ID NO: 1 and/or the resistant donor nucleotide of SNP_02, which is a Cytosine (C) at nucleotide 184 of SEQ ID NO: 3 or C at the equivalent position in a sequence having at least 90%, preferably at least 91%, 92%, 93%, 94%, 95%, 96%, 97%, 98% or 99% sequence identity to SEQ ID NO: 3. Resistance against these races is conferred at least when the introgression fragment is in homozygous form, optionally also when the introgression fragment is in heterozygous form, depending on whether resistance against a race is dominant or recessive. Resistance against Pfs races 8, 9, 11, 13 and 16 was found to be conferred in a dominant manner. Resistance against race 17 is also likely dominant. Whether RPF15 confers resistance against races 1, 2, 3, 4, 5, 6, 7, 12, 14 and/or isolate UA0514 in a dominant or in a recessive manner has to be determined. As mentioned, the skilled person can easily determine this. What is known is that, when RPF15 (or the introgression fragment comprising RPF15) is present in homozygous form, the cultivated spinach plant is resistant against these races. In the deposited seeds the introgression fragment is present in homozygous form. So plants grown from said seeds can be crossed with a plant lacking the RPF15 gene, to generate F1 plants, and the F1 and/or F2 and/or F3 population can be tested for resistance to each of the Pfs races, in order to determine if the resistance conferred is seen when RPF15 is in heterozygous form (dominant) or only when RPF15 is in homozygous form (recessive). As mentioned, the gene does not confer resistance against races 10 and 15.

A representative sample of seeds of a cultivated spinach line comprising the RPF15 gene (that is the introgression fragment comprising the RPF15 gene) in homozygous form has been deposited under the Budapest Treaty under Accession number 42608 by Nunhems B.V. on 12 July 2016, at NCIMB Ltd. Thus, in an embodiment of the invention, the RPF15 resistance gene (or the introgression fragment comprising the gene) is the gene (or the introgression fragment) as found in seed deposited under accession number NCIMB 42608, or from a plant or a part thereof grown from seed deposited under accession number NCIMB 42608, or from a cell culture derived from said seed or said plant or said part thereof. Obviously, also progeny of NCIMB 42608 are encompassed, which progeny comprise the RPF15 gene (or the introgression fragment comprising the gene) in their nuclear genome.

When referring herein to a cultivated spinach plant or plant part "comprising the RPF15 gene" this is understood to mean that the spinach plant or plant part comprises the introgression fragment, which fragment comprises the RPF15 gene from a wild *S. turkestanica* donor at the RPF15 locus on the chromosome. In one aspect the wild *S. turkestanica* donor is the same donor as in the deposited seeds, i.e. the *S. turkestanica* sequence of the RPF15 gene and of the fragment comprising the RPF15 gene has the same nucleotide sequence as in the deposited seeds. This can be determined by e.g. whole genome sequencing. Alternatively, the wild *S. turkestanica* donor may be a different accession, comprising the RPF15 gene (conferring e.g. the same Pfs resistance) but having a nucleotide sequence comprising at least 90%, 91%, 92%, 93%, 94%, 95%, 96%, 97%, 98% or 99% sequence identity to the RPF15 gene of the deposited seeds or to the introgression fragment comprising the RPF15 gene of the deposited seeds.

The cultivated spinach line of which a representative sample of seeds were deposited under NCIMB 42608, comprising the *S. turkestanica* introgression fragment carrying RPF15 in homozygous form, is resistant against Pfs races 1, 2, 3, 4, 5, 6, 7, 8, 9, 11, 12, 13, 14, 16, 17 and UA0514.

The RPF15 gene is located on an introgression fragment from a wild relative of spinach. In one aspect of the invention, the introgression fragment is from *Spinacia turkestanica* and comprises in addition to the RPF15 gene a molecular marker linked to the RPF15 gene and which can be used to select a fragment comprising RPF15. An Adenine at nucleotide 106 of SEQ ID NO: 1 (the resistant donor nucleotide for SNP_01) was found to be linked to the RPF15 gene on the introgression fragment. A Cytosine at nucleotide 184 of SEQ ID NO: 3 (the resistant donor nucleotide for SNP_02) was also found to be linked to the RPF15 gene on the introgression fragment. Susceptible lines lacking the introgression fragment were found to contain a Guanine at nucleotide 106 of SEQ ID NO: 1 (as shown in SEQ ID NO: 2) as well as a Guanine at nucleotide 184 of SEQ ID NO: 3 (as shown in SEQ ID NO: 4) or a Guanine at nucleotide 607751 of chromosome 3 as published on Spinachbase, which nucleotide is the equivalent nucleotide to nucleotide 184 of SEQ ID NO: 3 or 4 (also shown on position 190 of the upper sequence of FIG. 2), as can be seen from the pairwise alignment (using the Emboss program Needle). The sequence of the susceptible *S. oleracea* plant lines may thus show variation at the SNP marker region. Thus, in one aspect the RPF15 gene is linked to an Adenine at nucleotide 106 of SEQ ID NO: 1 or to A at the equivalent position in a sequence comprising at least 90%, preferably at least 91%, 92%, 93%, 94%, 95%, 96%, 97%, 98% or 99% sequence identity to SEQ ID NO: 1 and/or linked to a Cytosine at nucleotide 184 of SEQ ID NO: 3 or to C at the equivalent position in a sequence comprising at least 90%, preferably at least 91%, 92%, 93%, 94%, 95%, 96%, 97%, 98% or 99% sequence identity to SEQ ID NO: 3. In an aspect of the invention, the resistance gene, RPF15, is obtained or obtainable from an *S. turkestanica* accession which accession has the same Pfs resistance phenotype as conferred by RPF15 (e.g. as the deposited seeds) and comprises an Adenine at nucleotide 106 of SEQ ID NO: 1 (the resistant donor nucleotide for SNP_01) or an Adenine at the equivalent position in a sequence comprising at least 90%, preferably at least 91%, 92%, 93%, 94%, 95%, 96%, 97%, 98% or 99% sequence identity to SEQ ID NO: 1, as well as comprising a Cytosine at nucleotide 184 of SEQ ID NO: 3 (the resistant donor nucleotide for SNP_02) or Cytosine at the equivalent position in a sequence comprising at least 90%, preferably at least 91%, 92%, 93%, 94%, 95%, 96%, 97%, 98% or 99% sequence identity to SEQ ID NO: 3.

In another aspect of the invention, the introgression fragment comprising RPF15 is the introgression as present in (and as obtainable from; or obtained from; or derivable from; or derived from) a spinach seed deposited under accession number NCIMB 42608 or a sub-fragment thereof (retaining RPF15), wherein said introgression fragment (or sub-fragment) comprises the RPF15 gene conferring resistance to at least Pfs races 8, 9, 11, 13 and 16. In one aspect the introgression fragment comprises also SEQ ID NO: 1 and/or SEQ ID NO: 3.

The introgression fragment present in the deposited seeds is from a specific donor accession and thus has a unique nucleotide sequence. The whole fragment can be easily transferred into other spinach lines or varieties, by crossing a plant grown from the deposited seeds with another spinach plant and selecting a descendant comprising the introgression fragment. Selection can be by various methods, by the Pfs resistance phenotype and/or selecting progeny comprising SEQ ID NO: 1 and/or sequencing, SNP genotyping (selecting progeny comprising an Adenine for SNP_01, etc.).

The fragment can also be identified by one or more molecular markers (e.g. SNP markers, AFLP markers, RFLP markers, etc.), especially molecular markers which are polymorphic between cultivated spinach and the introgression fragment from the wild donor. Typically, a mapping population is used to generate markers. For example markers which are specific for the introgression fragment may be generated which are within 6 cM, 5 cM, 4 cM, 3 cM, 2 cM, 1 cM from the RPF15 gene and/or within 1 Mb, 0.9 Mb, 0.8 Mb, 0.7 Mb, 0.6 Mb, 0.5 Mb, 0.4 Mb, 0.3 Mb, 0.2 Mb, 0.1 Mb, or less from the RPF15 gene. In a particularly preferred embodiment the introgression fragment comprising the RPF15 gene is obtained through a method that comprises the step of growing a seed of NCIMB 42608 into a plant.

In another embodiment a cultivated spinach plant is provided which comprises the RPF15 gene on a sub-fragment of the introgression fragment present in the seed of NCIMB 42608. Such plants can be generated by selfing or crossing a plant grown from seed of NCIMB 42608 with another spinach plant and selecting descendants which have a shorter introgression fragment, i.e. where a recombination event occurred between homologous chromosomes within the introgression fragment, so that part of the fragment is recombined off. For example recombinant inbred lines can be generated which have different sub-fragments of the original full-size introgression fragment present in seeds of NCIMB 42608. The original introgression fragment from the *S. turkestanica* donor is estimated to be equal to or less than 3.0 Mb in size, especially equal to or less than 2.0 Mb in size. Sub-fragments comprising RPF15 may thus be less than 3.0 Mb, less than 2.0 Mb, such as less than 1.0 Mb, 0.7 Mb, 0.6 Mb, 0.5 Mb, 0.4 Mb, 0.3 Mb, 0.2 Mb, 0.1 Mb or less and may still comprise the RPF15 gene. Optionally sub-fragments also retain SEQ ID NO: 1 and/or SEQ ID NO: 3.

As mentioned previously, in the mapping population for RPF15, the SNP nucleotide of the SNP_01 from the *S. turkestanica* donor is an Adenine at position 106 of SEQ ID NO: 1, instead of Guanine, which is the SNP nucleotide of the recurrent parent (*S. oleracea*, lacking the introgression), as shown at position 106 of SEQ ID NO: 2 and the SNP nucleotide of the SNP_02 said donor is a Cytosine at position 184 of SEQ ID NO: 3, instead of Guanine, which is the SNP nucleotide of said recurrent parent, as shown at position 184 of SEQ ID NO: 4. SEQ ID NO: 2 and SEQ ID NO: 4 are found in susceptible lines. A diploid spinach plant homozygous for the introgression fragment comprising RPF15 therefore has an Adenine at the SNP_01 position of each of the homologous chromosomes (i.e. 'AA' genotype) and a Cytosine at the SNP_02 position of each of the homologous chromosomes (i.e. 'CC' genotype). A spinach plant heterozygous for the introgression fragment has an Adenine at the SNP_01 position of one chromosome, and a Guanine, Cytosine or Thymine at the equivalent position of the other chromosome, depending on the recurrent parent background (i.e. 'AG' or 'AC' or 'AT' genotype and a Cytosine at the SNP_02 position of one chromosome, and a Guanine, Adenine or Thymine at the equivalent position of the other chromosome, depending on the recurrent parent background (i.e. 'CG' or 'CA' or 'CT' genotype).

The present invention encompasses introgression fragments from the *S. turkestanica* donor as present in the deposited seeds (comprising RPF15 and optionally comprising SEQ ID NO: 1; and an Adenine at nucleotide 106 of SEQ ID NO:1 and/or comprising SEQ ID NO: 3; and an Adenine at nucleotide 184 of SEQ ID NO:3) and also from other *S. turkestanica* donors comprising RPF15 on the same chromosome locus on chromosome 3 of the spinach genome, but wherein the introgression fragment has a nucleotide sequence which is not 100% identical to the sequence of the introgression fragment present in the deposited seeds (e.g. having only at least 90%, 91%, 92%, 93%, 94%, 95%, 96%, 97%, 98% sequence identity to the introgression fragment present in the deposited seeds). Such an introgression fragment may in one aspect comprise SNP_01 and/or SNP_02 (wherein SNP_01 has an Adenine at nucleotide 106 or the equivalent position of a sequence comprising at least 90%, 91%, 92%, 93%, 94%, 95%, 96%, 97%, 98% or 99% sequence identity to SEQ ID NO:1 and SNP_02 has a Cytosine at nucleotide 184 or the equivalent position of a sequence comprising at least 90%, 91%, 92%, 93%, 94%, 95%, 96%, 97%, 98% or 99% sequence identity to SEQ ID NO:3). Thus the marker sequence of SEQ ID NO: 1 and/or SEQ ID NO: 3 may also not be 100% identical in such a different *S. turkestanica* donor. The invention further also encompasses sub-fragments of such a introgression fragment from other *S. turkestanica* donors, comprising RPF15 and optionally comprising an Adenine at nucleotide 106 of SEQ ID NO: 1 or A at the equivalent position in a sequence comprising at least 90%, preferably at least 91%, 92%, 93%, 94%, 95%, 96%, 97%, 98% or 99% sequence identity to SEQ ID NO: 1 and/or a Cytosine at nucleotide 184 of SEQ ID NO: 3 or C at the equivalent position in a sequence comprising at least 90%, preferably at least 91%, 92%, 93%, 94%, 95%, 96%, 97%, 98% or 99% sequence identity to SEQ ID NO: 3.

Thus, the invention also encompasses a sub-fragment of aforementioned introgression fragment comprising the RPF15 gene, wherein said sub-fragment comprises the RPF15 gene conferring resistance to at least Pfs races 8, 9, 11, 13 and 16, preferably 8, 9, 11, 13, 16 and 17, and is a part of the introgression fragment as present in seed deposited under accession number NCIMB 42608 or is a part of an introgression fragment of a different *S. turkestanica* donor having substantial sequence identity to the introgression fragment present in the deposited seeds. The invention encompasses said sub-fragment comprising the RPF15 gene and comprising the resistant donor nucleotide for SNP_01, which is an Adenine at nucleotide 106 of SEQ ID NO: 1 or an Adenine at the equivalent position in a sequence having at least 90%, 91%, 92%, 93%, 94%, 95%, 96%, 97%, 98% or 99% sequence identity to SEQ ID NO: 1 and/or comprising the resistant donor nucleotide for SNP_02, which is a Cytosine at nucleotide 184 of SEQ ID NO: 3 or Cytosine at the equivalent position in a sequence comprising at least 90%, preferably at least 91%, 92%, 93%, 94%, 95%, 96%, 97%, 98% or 99% sequence identity to SEQ ID NO: 3. Thus, the introgression sub-fragment is in one aspect obtained (and as obtainable from; or derivable; or derived) from the fragment as found in cultivated spinach seeds as deposited under accession number NCIMB 42608, and the sub-fragment retains the RPF15 gene (and the Pfs resistance phenotype conferred by the gene, and optionally SEQ ID NO: 1 and/or SEQ ID NO: 3), and the introgression fragment is in another aspect obtained from another *S. turkestanica* donor comprising an RPF15 gene at the same locus on chromosome 3. Spinach plants comprising such a shorter introgression fragment can be generated by crossing a plant of the invention with another spinach plant and selecting a recombinant progeny which retains the resistance phenotype conferred by the RPF15 gene, but which comprise a shorter introgression fragment. The skilled person can, for example, cross a plant grown from the deposited seeds with another cultivated spinach plant (e.g. a plant susceptible to one or more of Pfs races 8, 9, 11, 13, 16, 17), and then self the F1 progeny to produce an F2 population and identify recombinants (cross-over events) having occurred in the introgression fragment.

As mentioned previously, WO2015054339 describes a QTL on chromosome 6. The locus was introgressed from *S. tetrandra* and confers broad spectrum Pfs resistance, in particular "resistance to races 7, 10, 11, 12, 13, and 14 of *Peronospora farinosa* f. sp. *spinaciae* (Pfs), or to races 1-14 and UA4712 of *Peronospora farinosa* f. sp. *spinaciae* (Pfs)". (UA4712 is Pfs race 15). Chromosome 6 actually corresponds to chromosome 3 in SpinachBase. The two *S. tetrandra* sequences which flank the QTL, herein provided as SEQ ID NO: 5 and 6, are located at 1.4 Mb (SEQ ID NO: 5) and 0.7 Mb (SEQ ID NO: 6), whereby this *S. tetrandra* QTL must be located on the fragment spanning 0.7 to 1.4 Mb of chromosome 3. Inventors have also tested whether the sequences, which flank the QTL in *S. tetrandra*, are present in the seeds deposited under accession number NCIMB 42608. Neither the left nor the right flanking sequences (i.e. SEQ ID NO: 5 and 6) were present in the deposited seeds, as further described in the Examples. Instead, *S. oleracea* DNA was present in the deposited seeds at the corresponding chromosome region (provided as SEQ ID NO: 7 and 8).

Thus, in one aspect, a cultivated spinach plant of the invention, which comprises an introgression comprising RPF15, does not comprise the broad spectrum resistance locus described in WO2015054339.

The introgression fragment of the invention comprising the RPF15 gene, as present in seed deposited under NCIMB 42608, does not comprise SEQ ID NO: 5 or SEQ ID NO: 6. SEQ ID NO: 5 and SEQ ID NO: 6 are linked to the resistance-conferring introgression from *S. tetrandra* described in WO2015054339. SEQ ID NO: 5 and SEQ ID NO: 6 are not present in the introgression fragment of the invention, or in seed of the invention as deposited under NCIMB 42608. The seed deposited under NCIMB 42608, which comprise the RPF15 gene comprises SEQ ID NO: 7 at the equivalent region to SEQ ID NO: 5. The seed deposited under NCIMB 42608, which comprise the RPF15gene comprises SEQ ID NO: 8 at the equivalent region to SEQ ID NO: 6.

The RPF15 gene is useful because it is a single gene which confers dominant resistance to several pathogenic *Peronospora farinosa* races, that is at least Pfs races 8, 9, 11, 13 and 16, preferably 8, 9, 11, 13, 16 and 17. RPF15 can be used in generating resistant spinach varieties. In the art, resistance genes are commonly stacked (combined with other complementary resistance genes) to provide resistance against a large number of *Peronospora farinosa* races. To stack resistance genes in a hybrid variety, the gene should confer dominant resistance. This is especially important for conferring *Peronospora farinosa* resistance in the diploid spinach, because some resistance genes are allelic, limiting the number of possible combinations. Therefore, the products described herein (e.g. plants, plant parts, progeny plants, etc.) provide a significant improvement over the prior art.

In one aspect, the invention provides a spinach F1 hybrid plant and plant parts (and seed from which an F1 hybrid can be grown), wherein one parent is an inbred line which comprises the RPF15 gene of the invention in homozygous form. The other parent may be susceptible, or it may be an inbred parent line comprising a *P. farinosa* resistance gene selected from the group RPF1, RPF2, RPF3, RPF4, RPF5, RPF6, RPF7, RPF8, RPF9, RPF11, RPF12, RPF14, the R6 gene (of WO2013/064436), the p10 gene (of WO2017/194073), the R15 gene (of WO2017/084724) or the gene described in US20170127641 or US20170127642.

Also a method for producing a hybrid spinach seed is provided, comprising crossing a first parent spinach plant with a second parent spinach plant and harvesting the resulting hybrid spinach seed, wherein the first parent spinach plant comprises the RPF15 gene conferring dominant resistance to at least Pfs races 8, 9, 11, 13 and 16, preferably to 8, 9, 11, 13, 16 and 17, and that requires stacking with another downy mildew resistance gene to have resistance against races 10 and 15; and/or to have resistance against races 1-7, 12 and 14. Thus, in one aspect the other parent is an inbred parent line comprising a *P. farinose* resistance gene selected from the group RPF1, RPF2, RPF3, RPF4, RPF5, RPF6, RPF7, RPF8, RPF9, RPF11, RPF12, the R6 gene (of WO2013/064436), the p10 gene (of WO2017/194073), the R15 gene (of WO2017/084724) or the gene described in US20170127641 or US20170127642. Also encompassed is a F1 hybrid spinach seed, and a hybrid spinach plant or plant part grown from such seed, produced by this method.

For providing additional resistance against races 10 and/or 15, the following genes are most suitable: RPF2, RPF11, RPF12 for race 10, RPF1, RPF2, RPF4, RPF6, RPF7, RPF8, RPF11, RPF12, R15 or the gene described in US20170127641 or US20170127642 for race 15.

In one aspect of the invention a spinach plant comprising the RPF15 resistance gene is obtainable by (or obtained by, or derivable from, or derived from) crossing a spinach plant grown from seeds deposited under accession number NCIMB 42608, with another spinach plant, for example with a spinach plant lacking Pfs resistance genes (a susceptible plant) or with a spinach plant comprising one or more different Pfs resistance genes. An example of a suitable susceptible plant is variety Viroflay.

The spinach plant of the invention may e.g. be an inbred line, comprising RPF15 in homozygous form, or an F1 hybrid comprising the RPF15 gene in either homozygous or heterozygous form.

In one embodiment, the RPF15 resistance gene of the invention can be combined with other *Peronospora farinosa* resistance genes or resistance loci (e.g. RPF7-RPF9, RPF7? or RPF12, R6, R75, or the resistances disclosed in WO2015054339, WO2017194073 and EP2912940 etc.) or with other traits, such resistance against bacteria (e.g. *Pseudomonas syringae* pv. *spinacea, Erwinia carotovora*), fungi (e.g. *Albugo occidentalis, Colletotrichum dematium* f. sp. *spinaciae; Stemphylium botryosum* f. sp. *spinacia*), viruses (e.g. a virus causing Curly top disease, or Speckles, or Spinach blight, or Spinach Mosaic) or nematodes (e.g. Clover cyst nematode (*Heterodera trifolil*), Lesion nematode (*Pratylenchus* spp.), Root-knot nematode (*Meloidogyne* spp.) or Sugarbeet cyst nematode (*Heterodera schachtii*)). Combining can, for example, be done by traditional breeding techniques, e.g. by backcrossing in order to introduce one or more traits into a plant of the invention or in order to introduce the RPF15 gene of a plant of the invention into another spinach plant comprising such one or more additional traits or by other techniques, including gene editing or transformation. In one aspect a plant of the invention is used as a donor of the RPF15 gene, while in another aspect a plant of the invention is used as recipient of one or more other traits. A skilled person can obtain a hybrid plant resistant to all currently known Pfs races, namely Pfs 1 to 17 by combining the RPF15 gene with other suitable resistance genes. For example, RPF15 can be combined with RPF11 or RPF12 to obtain resistance to all currently known Pfs races.

The RPF15 resistance gene, or the introgression fragment on which it is located, or a sub-fragment of the fragment comprising RPF15, can be transferred from a plant of the invention to another spinach plant by various methods known to the skilled person. A donor of the RPF15 resistance gene may thus be e.g. a plant grown from the deposited seeds, or a progeny plant thereof.

Thus a donor of the RPF15 resistance gene can be NCIMB 42608 or a progeny of a plant grown from said deposit, a progeny of said plant, or a plant grown from a cell culture derived from said plant. The transferred RPF15 gene can confer resistance to at least Pfs races 8, 9, 11, 13 and 16, preferably to races 8, 9, 11, 13, 16 and 17, and also resistance to one or more (or all) of Pfs races 1 to 7, 12 and 14, and resistance to Pfs isolate UA0514 in the recipient plant.

The RPF15 resistance gene, or the introgression fragment on which it is located, or a sub-fragment thereof comprising the gene, can be used to make a hybrid plant (e.g. an F1 hybrid), or an inbred plant or a homozygous plant, optionally a doubled haploid plant. In a further aspect, the inbred or homozygous plant is a male parent line, preferably a male elite parent. In a yet further aspect, the inbred or homozygous plant is a female parent line, preferably a female elite parent. A male parent line can be crossed with a female parent line to make F1 hybrid seeds, comprising RPF15 (or the introgression fragment comprising RPF15, and optionally comprising SEQ ID NO: 1 and/or SEQ ID NO: 3) in homozygous form.

In an embodiment, the parent line functions as a donor of the RPF15 resistance gene. Said donor plant can be crossed with another spinach plant, and progeny can be obtained, including F1, F2, F3, or further generation selfing progeny, backcross progeny (e.g. BC1, BC2, BC1S1, BC2S1, BC1S2, etc.) etc. Plants having the same Pfs resistance phenotype as the initial plant of the invention can be identified and selected among the progeny. Likewise, the introgression fragment can be detected in the progeny, e.g. by detecting markers indicative of the introgression fragment (e.g. SNP_01) or sequencing, etc.

In one aspect, the inbred line is a cultivated plant of the species *Spinacia oleracea* comprising resistance against at least *Peronospora farinosa* races 8, 9, 11, 13 and 16, preferably to races 8, 9, 11, 13, 16 and 17, wherein said resistance is conferred by the single gene introgressed from *Spinacia turkestanica* (RPF15), said gene being linked to the resistant donor nucleotide for SNP_01, which is an Adenine (A) at nucleotide 106 of SEQ ID NO: 1 or an Adenine at the equivalent position of a sequence comprising at least 90%, 91%, 92%, 93%, 94%, 95%, 96%, preferably at least 97%, 98% or 99% sequence identity to SEQ ID NO: 1 and/or to the resistant donor nucleotide for SNP_02, which is a Cytosine (C) at nucleotide 184 of SEQ ID NO: 3 or C at the equivalent position of a sequence comprising at least 90%, 91%, 92%, 93%, 94%, 95%, 96%, preferably at least 97%, 98% or 99% sequence identity to SEQ ID NO: 3.

The RPF15 resistance gene, or the introgression fragment on which it is located, or a sub-fragment thereof, can also be transferred in various types of spinach, such as: savoy, semi-savoy, flat- or smooth leaved or oriental spinach. Preferably, the savoy, semi-savoy, flat- or smooth leaved or oriental cultivated spinach plant is a hybrid plant.

In one embodiment, a cultivated spinach plant is encompassed comprising resistance against Pfs races 8, 9, 11, 13 and 16, preferably to races 8, 9, 11, 13, 16 and 17, wherein said resistance is conferred by a single dominant gene RPF15 introgressed from a wild relative of spinach, preferably *S. turkestanica*, which gene is linked to SEQ ID NO: 1 or to a sequence comprising at least 90%, 91%, 92%, 93%, 94%, 95%, 96%, preferably at least 97%, 98% or 99% sequence identity to SEQ ID NO: 1 retaining Adenine at SNP_01 and/or SEQ ID NO: 3 or to a sequence comprising at least 90%, 91%, 92%, 93%, 94%, 95%, 96%, preferably at least 97%, 98% or 99% sequence identity to SEQ ID NO: 3 retaining Cytosine at SNP_02. The RPF15 gene can be identified in different accessions of wild relatives of spinach, especially in accessions of the species *S. turkestanica*, and can be introgressed into cultivated spinach. To do so, the skilled person can e.g. screen such an accession for the presence of the resistant donor nucleotide of SNP_01, which is an Adenine (A) at nucleotide 106 of SEQ ID NO: 1 or an Adenine at the equivalent position of a sequence comprising at least 90%, 91%, 92%, 93%, 94%, 95%, 96%, preferably at least 97%, 98% or 99% sequence identity to SEQ ID NO: 1 and/or linked to the resistant donor nucleotide for SNP_02, which comprises a Cytosine (C) at nucleotide 184 of SEQ ID NO: 3, or comprises a Cytosine at the equivalent position in a sequence comprising at least 90%, preferably at least 91%, 92%, 93%, 94%, 95%, 96%, 97%, 98% or 99% sequence identity to SEQ ID NO: 3 and/or test the Pfs resistance phenotype and optionally the inheritance (as single gene) to determine if that accession contains RPF15. Optionally also sequencing, fine mapping, allelism tests, etc. can be done to determine if the gene in the accession is indeed the RPF15 gene.

In a specific aspect, the resistance against *Peronospora farinosa* in a cultivated plant is conferred by an introgression fragment from *Spinacia turkestanica*. The cultivated spinach plant therefore comprises the RPF15 gene derived from *S. turkestanica* and is optionally linked to the resistant donor nucleotide for SNP_01, which is an Adenine (A) at nucleotide 106 of SEQ ID NO: 1 or A at the equivalent position of a sequence comprising at least 90%, 91%, 92%, 93%, 94%, 95%, 96%, preferably at least 97%, 98% or 99% sequence identity to SEQ ID NO: 1 and/or linked to the resistant donor nucleotide for SNP_02, which comprises a Cytosine (C) at nucleotide 184 of SEQ ID NO: 3, or comprises C at the equivalent position in a sequence comprising at least 90%, preferably at least 91%, 92%, 93%, 94%, 95%, 96%, 97%, 98% or 99% sequence identity to SEQ ID NO: 3.

Presence of the resistance gene RPF15 may be determined by resistance tests for at least Pfs races 8, 9, 11, 13 and 16 (preferably to races 8, 9, 11, 13, 16 and 17), optionally also resistance to one or more of Pfs races 1 to 7, 12 and 14, and/or resistance to isolate UA0514 and/or other Pfs isolates. Additionally susceptibility to races 10 and 15 can also confirm presence of RPF15. In an alternative embodiment resistance against a Pfs races, or a selection of Pfs races can be used as to indicate that the gene is transferred from a donor to a recipient plant. Thus, if e.g. the recipient parent in the cross lacks resistance against a particular Pfs race, then selection of a progeny plant which is resistant against that race indicates the transfer of the RPF15 gene.

The tests for presence of the resistance gene in a cultivated spinach plant (i.e. a spinach line or variety) comprise for example qualitative disease resistance assays under controlled environment conditions. The skilled person is familiar with applying different protocols for such assays. In short, seedlings of a plurality of plants of the plant genotype to be tested (e.g. at least 6, 7, 8, 9, 10, 11, 12, 13, 14, 15, 16, 17, 18, 19, 20, or more plants) are inoculated with inoculum of the Pfs race to be tested and the seedlings are incubated under conditions which are favorable to the pathogen. Several days after incubation, the plants are assessed for infection symptoms, especially sporulation on the cotyledons and/or leaves (e.g. first true leaf), and each plant is categorized as "resistant" (showing no signs of sporulation) or "susceptible" (showing sporulation). If a certain percentage of all plants of a genotype are classified as "resistant", e.g. more than about 85%, 90%, 95%, 98%, 99% (or even 100%), then the spinach plant genotype is resistant to the race tested. Obviously, also one or more control plants (e.g. a susceptible line or variety, a resistant line or variety) should be included in the assay using the same treatment(s) and environmental conditions, to ensure that the assay works as expected.

Such a test for presence of RPF15 may be done on plants homozygous or heterozygous for the gene, using any isolate or race of Pfs. If the plant is categorized as resistant according to the test, when the gene is present in heterozygous form, the resistance is dominant. A simple test may comprise crossing a plant comprising the resistance gene with a plant which is susceptible to at least one Pfs race (i.e. has no background resistance) and testing F1 progeny for resistance to that Pfs race. If that F1 progeny is resistant to that Pfs race, it can be concluded the resistance is dominant. Such a test has resulted in the conclusion that RPF15 confers dominant resistance to Pfs races 8, 9, 11, 13 and 16, and preferably 17. Another suitable test for dominant monogenic inheritance is crossing a plant comprising the resistance gene with a plant susceptible to all Pfs races, selfing the progeny from that cross to generate a F2 generation and observing segregation of resistance to Pfs races. If the segregation is a 3:1 ratio of resistant to susceptible plants the resistance is dominant monogenic. If the plant is categorized as resistant according to the test, only when the gene is present in homozygous form, the resistance inherited recessively.

Presence of the RPF15 resistance gene (or introgression fragment comprising the gene) in a spinach plant or plant part (e.g. a cell) may be also determined directly. The skilled person is aware of methods for screening, selecting or identifying a cultivated spinach plant (e.g. a progeny plant) or a part of a spinach plant, or a cell or a cell culture comprising RPF15 of the invention may be achieved by detecting one or more molecular markers linked to the RPF15 gene or locus, such as SNP_01. Thus, in one aspect the introgression fragment comprising the RPF15 gene is detectable by presence of the resistant donor nucleotide of SNP_01, which is an Adenine (A) at nucleotide 106 of SEQ ID NO: 1 or Adenine at the equivalent position of a sequence comprising at least 90%, preferably at least 91%, 92,%, 93%, 94%, 95%, 96%, 97%, 98% or 99% sequence identity to SEQ ID NO: 1 and/or the resistant donor nucleotide for SNP_02, which comprises a Cytosine (C) at nucleotide 184 of SEQ ID NO: 3, or comprises C at the equivalent position in a sequence comprising at least 90%, preferably at least 91%, 92%, 93%, 94%, 95%, 96%, 97%, 98% or 99% sequence identity to SEQ ID NO: 3 and/or any other molecular marker linked to RPF15 and/or the S. turkestanica introgression fragment comprising the RPF15 gene. Thus, the genome, especially chromosome 3 of the genome, comprising the introgression fragment can be distinguished by the skilled person from the genome, especially chromosome 3 of the genome lacking the introgression fragment and comprising S. oleracea genomic sequence instead.

The RPF15 gene is located at the beginning of chromosome 3, in the region starting at 0 Mb to 2.0 Mb of the chromosome 3 (as found in the SpinachBase genome), especially in the region starting 0.4 Mb and ending at 1.5 Mb. Thus, if this region is sequenced and comprises S. turkestanica sequence, optionally also the SNP_01 marker (SEQ ID NO: 1) and/or SNP_02 marker (SEQ ID NO: 3) linked to the gene, and the plant comprises the resistance phenotype as conferred by the RPF15 gene, then the plant or plant part (e.g. cell) comprises the RPF15 gene of the invention.

In another aspect, the invention provides a cultivated spinach seed comprising RPF15 as part of the introgression fragment or a sub-fragment of the introgression fragment, as present in the deposit under accession number NCIMB 42608. The invention also provides a plurality of cultivated spinach seeds comprising RPF15, preferably in a container.

The invention further provides a cultivated spinach plant comprising an introgression fragment from a donor that is a wild relative of spinach conferring dominant resistance to Peronospora farinosa races 8, 9, 11, 13 and 16, preferably to races 8, 9, 11, 13, 16 and 17, and resistance (potentially only when the fragment is in homozygous form) to Pfs races 1 to 7 and to isolate UA0514, optionally also to races 12 and 14, and/or other Pfs isolates. In one aspect of the invention, the fragment is introgressed from S. turkestanica. In another aspect of the invention, the introgression fragment is the introgression as present in seed deposited under accession number NCIMB 42608, or a short fragment of that fragment. The invention therefore also encompasses a cultivated spinach plant comprising a sub-fragment of aforementioned introgression fragment, wherein said sub-fragment confers dominant resistance to Pfs races 8, 9, 11, 13 and 16, preferably to races 8, 9, 11, 13, 16 and 17, and resistance (potentially only when the fragment is in homozygous form) to Pfs races 1 to 7, 12 and 14, and to isolate UA0514 and/or other Pfs isolates. The invention further encompasses a cultivated spinach plant comprising said sub-fragment, wherein said sub-fragment is a part of the introgression fragment as present in seed deposited under NCIMB 42608. The shorter sub-fragment retains the RPF15 gene.

The cultivated spinach plant of the invention can be a hybrid plant, especially an F1 hybrid, or an inbred plant for example an inbred line which can be used as a parent for F1 hybrid seed production or a homozygous plant, optionally a doubled haploid plant.

The RPF15gene can be transferred into any spinach line or variety.

In other words, the RPF15 gene can be introduced into any other spinach plant by introgression from a plant grown from seeds of which a representative sample was deposited under NCIMB 42608, or any spinach plant derived therefrom and retaining the RPF15 gene. The deposited seeds are therefore a source of the RPF15 resistance gene of the invention, as is a spinach plant not directly obtained from the deposit, but indirectly obtained (e.g. through a later released commercial varieties) and which comprises RPF15gene of the invention.

Other sources of the RPF15 gene may be identified, e.g. in wild relatives of spinach (especially other S. turkestanica accessions which have the same Pfs resistance phenotype and/or comprise one or both of the markers linked to RPF15 provided herein (SNP_01 and/or SNP_02) and e.g. an allelism test may be used to determine whether another gene, conferring the same Pfs resistance phenotype, is the same gene or a different gene. Likewise, sequencing may be used to confirm the presence of the RPF15 gene. Alternative methods to determine whether another gene is the same gene include the development of at least one molecular marker linked to the RPF15 gene of the invention and analyzing whether said marker occurs in plants comprising the other gene. Examples of suitable markers are the resistant donor nucleotide of SNP_01, which has an Adenine (A) at nucleotide 106 of SEQ ID NO: 1 or an Adenine at the equivalent position of a sequence comprising at least 90%, preferably at least 91%, 92,%, 93%, 94%, 95%, 96%, 97%, 98% or 99% sequence identity to SEQ ID NO: 1 and/or the resistant donor nucleotide for SNP_02, which has a Cytosine (C) at nucleotide 184 of SEQ ID NO: 3, or C at the equivalent position in a sequence comprising at least 90%, preferably at least 91%, 92%, 93%, 94%, 95%, 96%, 97%, 98% or 99% sequence identity to SEQ ID NO: 3.

In one aspect a method is provided for generating a cultivated spinach plant comprising the RPF15 gene, comprising the steps of:
a) Crossing a spinach plant comprising the RPF15 gene as described herein with another spinach plant to produce a progeny plant;
b) Optionally selfing the progeny plant of step a one or more times to produce a further generation selfing progeny and optionally producing seed;

In an embodiment, the other spinach plant of step a) is susceptible to at least one of Pfs races 8, 9, 11, 13 and 16 or 17. In a further embodiment, the other spinach plant of step a) is an inbred plant or a homozygous plant or a male parent line or a female parent line, or preferably an elite male parent line or an elite female parent line.

In another aspect the method comprising steps a) and optionally b) is provided, followed by
c) Identifying the progeny plant of step a or b that comprises the RPF15 resistance gene by determining whether the progeny plant comprises resistance against at least Pfs races 8, 9, 11, 13 and 16, preferably against races 8, 9, 11, 13, 16 and 17, and/or comprises an Adenine at nucleotide 106 of SEQ ID NO: 1 or an Adenine at the equivalent position of a sequence comprising at least 90%, preferably at least 91%, 92,%, 93%, 94%, 95%, 96%, 97%, 98% or 99% sequence identity to SEQ ID NO: 1; and/or comprises a Cytosine (C) at nucleotide 184 of SEQ ID NO: 3, or a Cytosine at the equivalent position in a sequence comprising at least 90%, preferably at least 91%, 92%, 93%, 94%, 95%, 96%, 97%, 98% or 99% sequence identity to SEQ ID NO: 3; and/or which comprises an introgression fragment from *S. turkestanica* comprising the RPF15 gene.

d) Optionally crossing the identified progeny plant of step c to another spinach plant to produce a progeny plant or progeny seed.

In another embodiment a method for generating a spinach plant comprising the RPF15 gene (conferring resistance to at least Pfs races 8, 9, 11, 13 and 16, preferably to races 8, 9, 11, 13, 16 and 17), optionally further resistance to one or more of Pfs races 1 to 7, 12 and 14 and/or to isolate UA0514 and/or other Pfs isolates) is provided, comprising the steps of:

a) Crossing a spinach plant comprising an introgression fragment obtainable from (or as present in) seed as deposited under NCIMB 42608, which introgression fragment comprises SEQ ID NO: 1 and/or SEQ ID NO: 3, with another spinach plant;

b) Optionally selfing the progeny plant of step a one or more times to produce a further generation selfing progeny and optionally collecting seeds produced on the plant;

In an embodiment, the other spinach plant of step a) is susceptible to at least one of Pfs races 8, 9, 11, 13 and 16 or 17. In a further embodiment, the other spinach plant of step a) is an inbred plant or a homozygous plant or a male parent line or a female parent line, or preferably an elite male parent line or an elite female parent line.

In another aspect the method comprising steps a) and optionally b) is provided, followed by c) Identifying the progeny plant of step a or b that comprises the RPF15 resistance gene by determining whether the progeny plant comprises resistance against at least Pfs races 8, 9, 11, 13 and 16 and/or comprises SEQ ID NO: 1 and/or SEQ ID NO: 3;

d) Optionally crossing the identified progeny plant of step c to another spinach plant of to produce a progeny plant or seed.

Regarding both methods, the following is encompassed herein: In one aspect the plant of step a) comprises the RPF15 gene as found in seeds deposited under accession number NCIMB 42608. The spinach plant may be the plant grown from the seeds of the deposit or any spinach plant made using, or having used, the seed deposit and which retains the Pfs resistance phenotype (and the RPF15 gene conferring it) and optionally which retains SEQ ID NO: 1 and/or SEQ ID NO: 3. This includes commercial spinach varieties which were made using the seed deposit. Thus, the spinach plant of a) comprises the RPF15gene according to the invention, e.g. as found in (or as obtainable from; obtained from; derivable from; derived from) NCIMB 42608.

Selections (or identification) in step c) may be made based on the phenotype (i.e. using a Pfs resistance assay) and/or based on molecular methods, such as detection of molecular markers linked to the RPF15 gene or locus, for example of the resistant donor nucleotide of SNP_01, which is Adenine (A) at nucleotide 106 of SEQ ID NO: 1 or Adenine at the equivalent position of a sequence comprising at least 90%, preferably at least 91%, 92,%, 93%, 94%, 95%, 96%, 97%, 98% or 99% sequence identity to SEQ ID NO: 1 and/or the resistant donor nucleotide for SNP_02, which is a Cytosine (C) at nucleotide 184 of SEQ ID NO: 3, or a Cytosine at the equivalent position in a sequence comprising at least 90%, preferably at least 91%, 92%, 93%, 94%, 95%, 96%, 97%, 98% or 99% sequence identity to SEQ ID NO: 3, or other methods such as sequencing.

In the methods above, the spinach plant of step (a) preferably comprises the RPF15 gene (i.e. the introgression fragment or a sub-fragment thereof comprising the RPF15 gene) in homozygous form. In step a) the spinach plant comprising the resistance is, in one aspect, crossed with another spinach plant which is susceptible against at least one of the Pfs races against which the plant of a) is resistant. If the second parent in b) is a spinach plant which is susceptible against at least one of the Pfs races against which the plant of a) is resistant, then the selection in step (d) and/or (f) may be based on selecting plants which now have resistance against that race.

In the above methods also plants can be selected and/or identified which retain the Pfs resistance phenotype conferred by the RPF15 gene, but which have a smaller introgression fragment than the one present in the deposited seeds. This can have advantages, as negative traits of *S. turkestanica* coupled to the introgression fragment can thereby be removed. It is therefore preferred to reduce the size of the introgression fragment by recombination and to select plants comprising smaller introgression fragments, but which retain the resistance-conferring gene. So, in one aspect spinach with all sizes of introgression fragments originating from (or derived from; or derivable from; or obtained from; or obtainable from) seeds deposited under accession number NCIMB 42608 are included herein, as long as the Pfs resistance conferring part (i.e. the RPF15gene) is retained in the spinach plant. As mentioned, the presence can be tested/selected phenotypically and/or using molecular methods known in the art.

Also provided is a method for generating a spinach plant comprising dominant resistance against at least Pfs races 8, 9, 11, 13 and 16 (preferably races 8, 9, 11, 13, 16 and 17) comprises the steps of:

a) crossing a first spinach plant of the species *Spinacia oleracea* with a second spinach plant which second spinach plant is susceptible against one or more of Pfs races 8, 9, 11, 13 and 16 or 17, wherein the first a spinach plant comprising resistance against Pfs races 8, 9, 11, 13 and 16 (preferably against races 8, 9, 11, 13, 16 and 17), and said resistance is conferred by a single gene introgressed from *S. turkestanica*, which gene is linked to the resistant donor nucleotide for SNP_01, which has an Adenine (A) at nucleotide 106 of SEQ ID NO: 1 or an Adenine at the equivalent position of a sequence comprising at least 91%, 92,%, 93%, 94%, 95%, 96%, 97%, 98% or 99% sequence identity to SEQ ID NO: 1 and/or linked to the resistant donor nucleotide for SNP_02, which comprises a Cytosine (C) at nucleotide 184 of SEQ ID NO: 3, or comprises a Cytosine at the equivalent position in a sequence comprising at least 90%, preferably at least 91%, 92%, 93%, 94%, 95%, 96%, 97%, 98% or 99% sequence identity to SEQ ID NO: 3;

b) selfing a plant grown from progeny of said crossing one or more times to produce a further generation selfing progeny and/or backcrossing a plant grown from progeny of said crossing or grown from the further generation selfing progeny with a spinach plant is susceptible against one or more of Pfs races 8, 9, 11, 13, 16 or 17; and c) identifying a spinach plant among the progeny plants of step b) that comprises the a single gene of the first parent plant of step a).

In one aspect, the genotype of SNP_01 (which is linked to the RPF15 gene) is used to identify a plant in step c). The nucleotide of SNP_01 is Adenine, i.e. the donor nucleotide. Therefore in one aspect the plant comprises an introgression fragment which comprises the donor SNP_01 nucleotide.

In another aspect, the genotype of SNP_02 (which is linked to the RPF15 gene) is used to identify a plant in step c). The nucleotide of SNP_02 is Cytosine, i.e. the donor nucleotide. Therefore in one aspect the plant comprises an introgression fragment which comprises the donor SNP_02 nucleotide.

A plant produced by the above method is also an embodiment of the invention.

Also, a method for screening, identifying or detecting the presence of the RPF15 gene as described herein in a spinach plant or plant part is provided, comprising:
a) screening a cultivated spinach plant or plant part or DNA of such plant or plant part using a molecular marker assay which detects at least one SNP marker selected from the group consisting of:
  i) the resistant donor nucleotide of SNP_01, which has an Adenine (A) at nucleotide 106 of SEQ ID NO: 1 or an Adenine at the equivalent position of a sequence comprising at least 90%, preferably at least 91%, 92,%, 93%, 94%, 95%, 96%, 97%, 98% or 99% sequence identity to SEQ ID NO: 1;
  ii) the resistant donor nucleotide of SNP_02, which has a Cytosine (C) at nucleotide 184 of SEQ ID NO: 3, or a Cytosine at the equivalent position in a sequence comprising at least 90%, preferably at least 91%, 92%, 93%, 94%, 95%, 96%, 97%, 98% or 99% sequence identity to SEQ ID NO: 3
  iii) another marker linked to the RPF15 gene or to the introgression fragment comprising the RPF15 gene; and optionally
b) identifying or selecting a plant or plant part comprising the resistant donor SNP nucleotide for
SNP_01, which is an Adenine (A) at nucleotide 106 of SEQ ID NO: 1 or an Adenine at the equivalent position of a sequence comprising at least 90%, preferably at least 91%, 92,%, 93%, 94%, 95%, 96%, 97%, 98% or 99% sequence identity to SEQ ID NO: 1 and/or the resistant donor nucleotide for SNP_02, which is Cytosine (C) at nucleotide 184 of SEQ ID NO: 3, or Cytosine at the equivalent position in a sequence comprising at least 90%, preferably at least 91%, 92%, 93%, 94%, 95%, 96%, 97%, 98% or 99% sequence identity to SEQ ID NO: 3; and/or another marker linked to the RPF15 gene or to the introgression fragment comprising the RPF15 gene.

In yet another aspect, a method for detecting whether a cultivated spinach plant comprises an introgression fragment comprising the RPF15 gene as described herein, is provided, said method comprising:
a) screening a plant or plant part (or DNA obtained from said plant or plant part) using a molecular marker assay which detects at least one SNP marker selected from the group consisting of:
  i) the resistant donor nucleotide for SNP_01, which has an Adenine (A) at nucleotide 106 of SEQ ID NO: 1 or an Adenine at the equivalent position of a sequence comprising at least 90%, preferably at least 91%, 92,%, 93%, 94%, 95%, 96%, 97%, 98% or 99% sequence identity to SEQ ID NO: 1; and/or
  ii) the resistant donor nucleotide of SNP_02, which has a Cytosine (C) at nucleotide 184 of SEQ ID NO: 3, or a Cytosine at the equivalent position in a sequence comprising at least 90%, preferably at least 91%, 92%, 93%, 94%, 95%, 96%, 97%, 98% or 99% sequence identity to SEQ ID NO: 3; and/or
  iii) another marker linked to the RPF15 gene or to the introgression fragment comprising the RPF15 gene.

Also a cultivated spinach plant or plant part derived from, obtained from, obtainable from or derivable from or identified or detected in any of the above methods are embodiments of the invention, said plant comprising resistance to at least Pfs races 8, 9, 11, 13 and 16 (preferably to at least races 8, 9, 11, 13, 16 and 17) conferred by RPF15 or said plant part comprising the RPF15 gene (or introgression fragment comprising the gene, and optionally the marker linked to the gene).

A plant of the invention can be used to generate a progeny, which has or retains the Pfs resistance gene of the invention as obtainable from (as present in; as derivable from; as obtained or derived from) seeds deposited under NCIMB 42608. To generate progeny, a spinach according to the invention can be selfed and/or crossed one or more times with another spinach plant and seeds can be collected. The presence of the RPF15 gene in the progeny plants can be determined (i.e. progeny plants comprising the RPF15 gene can be identified/selected) by the Pfs resistance phenotype and/or molecular methods, such as molecular markers (e.g. SNP markers) linked to the RPF15 gene or locus.

The invention further contemplates use of the RPF15 gene (and use of an introgression fragment comprising the gene) to confer resistance against at least Pfs races 8, 9, 11, 13 and 16 (preferably to at least races 8, 9, 11, 13, 16 and 17), optionally further to races 1, 2, 3, 4, 5, 6, 7, 12, 14 and isolate UA0514. While at the same time the gene (introgression fragment) does not confer resistance against Pfs races 10 and 15.

In one embodiment, the use of a spinach plant, or progeny of said plant (e.g. obtained by selfing), or of a cell or cell culture that is regenerable, or a plant part that can be vegetatively propagated, is provided for generating a cultivated spinach plant comprising resistance to at least Pfs races 8, 9, 11, 13 and 16 (preferably to at least races 8, 9, 11, 13, 16 and 17), optionally further to one or more of Pfs races 1 to 7, 12, 14, and/or optionally to isolate UA0514 and/or other Pfs isolates, where representative seeds of said plant have been deposited under accession number NCIMB 42608.

In another embodiment, the invention contemplates use of a spinach plant comprising resistance to at least Pfs races 8, 9, 11, 13 and 16 (preferably to at least races 8, 9, 11, 13, 16 and 17) conferred by an introgression fragment obtainable from a seed deposited under accession number NCIMB 42608, or from progeny thereof (e.g. obtained by selfing), for generating a cultivated spinach plant comprising resistance to at least Pfs races 8, 9, 11, 13 and 16 (preferably to at least races 8, 9, 11, 13, 16 and 17), optionally further to one or more of Pfs races 1 to 7, 12, 14 and/or optionally to isolate UA0514 and/or other Pfs isolates.

Seeds

The invention provides a seed from which any plant of the invention can be grown. Furthermore, the invention provides a plurality of such seed. A seed of the invention can be distinguished from other seeds due to the presence of the RPF15 resistance gene, either phenotypically (based on plants having the RPF15 resistance phenotype) and/or using molecular methods.

In one aspect, a plurality of seed is packaged into a container (e.g. a bag, a carton, a can etc.). Containers may be any size. The seeds may be pelleted prior to packing (to form pills or pellets) and/or treated with various compounds, including seed coatings.

In an embodiment of the invention, the spinach seed is primed. Priming is a water-based process that is performed on seeds to increase uniformity of germination and emergence from the soil, and thus enhance vegetable stand establishment. Priming decreases the time span between the emergence of the first and the last seedlings. Methods for priming spinach seeds are well known in the art (see, e.g., Chen et al 2010, Seed Sci. & Technol. 38: 45-57). In another embodiment, the spinach seed is treated with crop protection, or film coated, or pelleted. Film coating and treatment with crop protection are commonly combined, see e.g. US20170127670.

Plant Parts and Vegetative Reproductions

In a further aspect a plant part, obtained from (obtainable from) a plant of the invention is provided herein, and a container or a package comprising said plant part.

In a preferred embodiment the plant part is a leaf of a spinach plant of the invention or a plurality of leaves, or part of a leaf, preferably a harvested leaf. Such a leaf may be loose, bunched, fresh (e.g. in a container, for example a bag), frozen, blanched or boiled. Such a leaf may be fresh or processed, and they may be part of food or feed products. A leaf may be harvested in any stage of its development, preferred stages are baby leaf and mature leaf.

Other plant parts, of a plant of the invention, include a leaf, a part of a leaf, a stem, a part of a stem, a stalk, a part of a stalk, a shoot, a part of a shoot, a bud or a part of a bud, a cutting, a root, a part of a root, a root tip, a petiole, a part of a petiole, a cotyledon, a part of a cotyledon, a flower, a part of a flower, a petal, a part of a petal, a stamen, a part of a stamen, an anther, a part of an anther, pollen, a stigma, a part of a stigma, a style, a part of a style, an ovary, a part of an ovary, an ovule, a part of an ovule, a seed, a part of a seed, a seed coat, an embryo, a part of an embryo, a hypocotyl, an embryo sac, a fruit, a part of a fruit, a cell, a protoplast, callus, a microspore, meristem, cambium etc. The various stages of development of aforementioned plant parts are comprised in the invention.

Seeds include for example seeds produced on the plant of the invention after self-pollination or seed produced after cross-pollination, e.g. pollination of a plant of the invention with pollen from another spinach plant or pollination of another spinach plant with pollen of a plant of the invention.

In one aspect, the plant parts or seeds can be identified by the presence of the donor SNP nucleotide for the resistant donor nucleotide of SNP_01, which has Adenine (A) at nucleotide 106 of SEQ ID NO: 1 or an Adenine at the equivalent position of a sequence comprising at least 90%, 91%, 92,%, 93%, 94%, 95%, 96%, 97%, 98% or 99% sequence identity to SEQ ID NO: 1 and or for the resistant donor nucleotide for SNP_02, which has a Cytosine (C) at nucleotide 184 of SEQ ID NO: 3, or a Cytosine at the equivalent position in a sequence comprising at least 90%, preferably at least 91%, 92%, 93%, 94%, 95%, 96%, 97%, 98% or 99% sequence identity to SEQ ID NO: 3.

In a further aspect, the plant part is a plant cell. In still a further aspect, the plant part is a non-regenerable cell or a regenerable cell. In another aspect the plant cell is a somatic cell. In one aspect the cell is isolated from its natural location.

A non-regenerable cell is a cell which cannot be regenerated into a whole plant through in vitro culture. The non-regenerable cell may be in a plant or plant part (e.g. a leaf) of the invention. The non-regenerable cell may be a cell in a seed, or in the seed-coat of said seed. Mature plant organs, including a mature leaf, a mature stem or a mature root, comprise at least one non-regenerable cell. Maturing plant organs such as a baby leaf spinach leaf also comprise at least one non-regenerable cell.

Moreover, there is provided an in vitro cell culture or tissue culture of spinach plants of the invention in which the cell- or tissue culture is derived from a plant part described above, such as, for example and without limitation, a leaf, a part of a leaf, a stem, a part of a stem, a stalk, a part of a stalk, a shoot, a part of a shoot, a bud or a part of a bud, a cutting, a root, a part of a root, a root tip, a petiole, a part of a petiole, a cotyledon, a part of a cotyledon, a flower, a part of a flower, a petal, a part of a petal, a stamen, a part of a stamen, an anther, a part of an anther, pollen, a stigma, a part of a stigma, a style, a part of a style, an ovary, a part of an ovary, an ovule, a part of an ovule, a seed, a part of a seed, a seed coat, an embryo, a part of an embryo, a hypocotyl, an embryo sac, a fruit, a part of a fruit, a cell, a protoplast, callus, a microspore, meristem, cambium, a somatic cell, a non-reproductive cell or a reproductive cell.

Therefore, one aspect provides a cell culture or tissue culture comprising cells or tissues derived from a part a of a spinach plant of the species *Spinacia oleracea* comprising resistance to Pfs races 8, 9, 11, 13 and 16 (preferably to at least races 8, 9, 11, 13, 16 and 17), wherein said resistance is conferred by a single gene introgressed from *Spinacia turkestanica*, which gene is linked to the resistant donor nucleotide of SNP_01, which has an Adenine (A) at nucleotide 106 of SEQ ID NO: 1 or an Adenine at the equivalent position of a sequence comprising at least 90%, 91%, 92,%, 93%, 94%, 95%, 96%, 97%, 98% or 99% sequence identity to SEQ ID NO: 1 and/or linked to the resistant donor nucleotide of SNP_02, which has a Cytosine (C) at nucleotide 184 of SEQ ID NO: 3, or a Cytosine at the equivalent position in a sequence comprising at least 90%, preferably at least 91%, 92%, 93%, 94%, 95%, 96%, 97%, 98% or 99% sequence identity to SEQ ID NO: 3.

In one aspect the cells or tissues can be identified by the presence of the donor genotype for SNP_01, which comprises Adenine (A) at nucleotide 106 of SEQ ID NO: 1 or Adenine at the equivalent position of a sequence comprising at least 90%, 91%, 92,%, 93%, 94%, 95%, 96%, 97%, 98% or 99% sequence identity to SEQ ID NO: 1 and/or the donor genotype for SNP_02, which comprises Cytosine (C) at nucleotide 184 of SEQ ID NO: 3, or Cytosine at the equivalent position in a sequence comprising at least 90%, preferably at least 91%, 92%, 93%, 94%, 95%, 96%, 97%, 98% or 99% sequence identity to SEQ ID NO: 3.

Also provided is a spinach plant regenerated from any of the above-described plant parts, or regenerated from the above-described cell or tissue cultures, said regenerated plant having a Pfs resistance phenotype (as conferred by the RPF15 gene), i.e. retains the RPF15 gene (or the introgression fragment comprising the RPF15 gene) of the invention. This plant can also be referred to as a vegetative propagation of plants of the invention.

Also provided is a harvested leaf of a plant of the invention and a package comprising a plurality of leaves of one or more plants of the invention. These leaves thus comprise the RPF15 gene of the invention, detectable by e.g. linked molecular markers or phenotypically (for the originally used whole plant and/or regenerated plant). A leaf can be harvested at any developmental stage. Preferred developmental stages for harvesting a leaf are mature stage and baby-leaf stage.

The invention also provides for a food or feed product comprising or consisting of a plant part described herein. The food or feed product may be fresh or processed, e.g., canned, steamed, boiled, fried, blanched and/or frozen etc. Examples are salad or salad mixtures comprising a leaf or a part of a leaf of a plant of the invention, or packaged frozen spinach.

A spinach plant of the invention or a progeny thereof retaining the Pfs resistance phenotype conferred by the RPF15 gene, and are optionally linked to the resistant donor nucleotide of SNP_01, which comprises Adenine (A) at nucleotide 106 of SEQ ID NO: 1 or an Adenine at the equivalent position of a sequence comprising at least 90%, 91%, 92,%, 93%, 94%, 95%, 96%, 97%, 98% or 99% sequence identity to SEQ ID NO: 1 and/or to the resistant donor nucleotide for SNP_02, which comprises Cytosine (C) at nucleotide 184 of SEQ ID NO: 3, or a Cytosine at the equivalent position in a sequence comprising at least 90%, preferably at least 91%, 92%, 93%, 94%, 95%, 96%, 97%, 98% or 99% sequence identity to SEQ ID NO: 3, and/or retaining the introgression fragment or sub-fragment comprising the RPF15 gene and optionally said SNP_01 and/or SNP_02 (or SEQ ID NO: 1 and/or SEQ ID NO: 3), as present in NCIMB 42608, and a part of the aforementioned plant, can be suitably packed for transport, and/or sold fresh. Such parts encompass any cells, tissues and organs obtainable from the seedlings or plants, such as but not limited to: a leaf, a cutting, pollen, a part of a leaf, and the like.

Leaves may be harvested immature, as baby-leaf or baby spinach, or mature. A plant, plants or parts thereof may be packed in a container (e.g., bags, cartons, cans, etc.) alone or together with other plants or materials. Parts can be stored and/or processed further. Encompassed are therefore also food or feed products comprising one or more of such parts, such leaves or parts thereof obtainable from a plant of the invention, a progeny thereof and parts of the aforementioned plants. For example, containers such as cans, boxes, crates, bags, cartons, Modified Atmosphere Packaging, films (e.g. biodegradable films), etc. comprising plant parts of plants (fresh and/or processed) of the invention are also provided herein.

Plants and Progeny

In another embodiment, plants and parts of spinach plants of the invention, and progeny of spinach plants of the invention are provided, e.g., grown from seeds, produced by sexual or vegetative reproduction, regenerated from the above-described plant parts, or regenerated from cell or tissue culture, in which the reproduced (seed propagated or regenerated or vegetatively propagated) plant comprises resistance to at least Pfs races 8, 9, 11, 13 and 16 (preferably to at least races 8, 9, 11, 13, 16 and 17) (optionally further to one or more of Pfs races 1, 2, 3, 4, 5, 6, 7, 12 and 14, and/or optionally against isolate UA0514 and/or other Pfs isolates (as conferred by the RPF15 gene, optionally linked to the resistant donor nucleotide of SNP_01, which comprises Adenine (A) at nucleotide 106 of SEQ ID NO: 1 or an Adenine at the equivalent position of a sequence comprising at least 90%, 91%, 92,%, 93%, 94%, 95%, 96%, 97%, 98% or 99% sequence identity to SEQ ID NO: 1 and/or to the resistant donor nucleotide for SNP_02, which comprises a Cytosine (C) at nucleotide 184 of SEQ ID NO: 3, or a Cytosine at the equivalent position in a sequence comprising at least 90%, preferably at least 91%, 92%, 93%, 94%, 95%, 96%, 97%, 98% or 99% sequence identity to SEQ ID NO: 3.

In one aspect, a progeny plant of a spinach plant of the invention is a progeny plant that retains the RPF15 resistance gene linked to the resistant donor nucleotide of SNP_01, which has an Adenine (A) at nucleotide 106 of SEQ ID NO: 1 or an Adenine at the equivalent position of a sequence comprising at least 90%, 91%, 92,%, 93%, 94%, 95%, 96%, 97%, 98% or 99% sequence identity to SEQ ID NO: 1 and/or to the resistant donor nucleotide for SNP_02, which has a Cytosine (C) at nucleotide 184 of SEQ ID NO: 3, or a Cytosine at the equivalent position in a sequence comprising at least 90%, preferably at least 91%, 92%, 93%, 94%, 95%, 96%, 97%, 98% or 99% sequence identity to SEQ ID NO: 3.

In another aspect, the progeny plant is a spinach plant of the species Spinacia oleracea comprising resistance to Pfs races 8, 9, 11, 13 and 16 (preferably to at least races 8, 9, 11, 13, 16 and 17), wherein said resistance is conferred by a single gene RPF15 introgressed from Spinacia turkestanica, which gene is in one aspect linked to the resistant donor nucleotide of SNP_01, which is Adenine (A) at nucleotide 106 of SEQ ID NO: 1 or an Adenine at the equivalent position of a sequence comprising at least 90%, 91%, 92,%, 93%, 94%, 95%, 96%, 97%, 98% or 99% sequence identity to SEQ ID NO: 1 and/or to the resistant donor nucleotide for SNP_02, which is Cytosine (C) at nucleotide 184 of SEQ ID NO: 3, or a Cytosine at the equivalent position in a sequence comprising at least 90%, preferably at least 91%, 92%, 93%, 94%, 95%, 96%, 97%, 98% or 99% sequence identity to SEQ ID NO: 3. Preferably, presence of RPF15 can be identified by aforementioned donor nucleotide for SNP_01 and/or SNP_02 and/or another marker linked to RPF15 or to the introgression fragment.

As mentioned before, whether or not a plant, progeny or vegetative propagation comprises the Pfs resistance phenotype as conferred by the RPF15 gene can be tested phenotypically using e.g. the Pfs disease resistance assays as described above or in the Examples; and/or using molecular techniques such as molecular marker analysis, DNA sequencing (e.g. whole genome sequencing to identify the introgression), chromosome painting, etc.

Furthermore, the invention provides for progeny comprising or retaining the Pfs resistance phenotype (conferred by the RPF15 gene), such as progeny obtained by, e.g., selfing one or more times and/or cross-pollinating a plant of the invention with another spinach plant of a different variety or breeding line, or with a spinach plant of the invention one or more times. In particular, the invention provides for progeny that retain the RPF15 gene (conferring the Pfs resistance phenotype) of (as found in) NCIMB 42608. In one aspect the invention provides for a progeny plant comprising the RPF15 resistance, such as a progeny plant that is produced from a spinach plant comprising the RPF15 resistance by one or more methods selected from the group consisting of: selfing, crossing, mutation, double haploid production or transformation. Mutation may be spontaneous mutations or human induced mutations or somaclonal mutations. In one embodiment, plants or seeds of the invention may also be mutated (by e.g. irradiation, chemical mutagenesis, heat treatment, TILLING, etc.) and/or mutated seeds or plants may be selected (e.g. natural variants, somaclonal variants, etc.) in order to change one or more characteristics of the plants. Similarly, plants of the invention may be transformed and regenerated, whereby one or more chimeric genes are introduced into the plants. Transformation can be carried out using standard methods, such as Agrobacterium tumefaciens mediated transformation or biolistics, followed by selection of the transformed cells and regeneration into plants. A desired trait (e.g. genes conferring pest or disease resistance, herbicide, fungicide or insecticide tolerance, etc.) can be introduced into the plants, or progeny thereof, by transforming a plant of the invention or progeny thereof with a transgene that confers the desired trait, wherein the transformed plant retains the RPF15 gene and the Pfs resistance phenotype conferred by it and has the desired trait.

In one aspect haploid plants and/or double haploid plants of plant of the invention are encompassed herein, which comprise resistance to at least Pfs races 8, 9, 11, 13 and 16 (preferably to at least races 8, 9, 11, 13, 16 and 17), optionally further to one or more of Pfs races 1, 2, 3, 4, 5, 6, 7, 12 and 14, and/or optionally against isolate UA0514 and/or other Pfs isolates, as conferred by the RPF15 gene or by the introgression fragment comprising the RPF15 gene. Haploid and double haploid (DH) plants can for example be produced by anther or microspore culture and regeneration into a whole plant. For DH production chromosome doubling may be induced using known methods, such as colchicine treatment or the like. So, in one aspect a spinach plant is provided, comprising Pfs resistance phenotype as described, wherein the plant is a double haploid plant.

In another embodiment the invention relates to a method for producing spinach seed, comprising crossing a plant of the invention with itself or a different spinach plant and harvesting the resulting seed. In a further embodiment the invention relates to seed produced according to this method and/or a spinach plant produced by growing such seed. Thus, a plant of the invention may be used as male and/or female parent, in the production of spinach seeds, whereby the plants grown from said seeds comprise resistance to at least Pfs 8, 9, 11, 13 and 16 (preferably to at least races 8, 9, 11, 13, 16 and 17), optionally further to one or more of Pfs races 1, 2, 3, 4, 5, 6, 7, 12 and 14, and/or optionally against isolate UA0514 and/or other Pfs isolates, due to the presence of the RPF15 gene.

Thus, in one aspect progeny of a spinach plant of the invention are provided, wherein the progeny plant is produced by selfing, crossing, mutation, double haploid production or transformation and wherein the progeny retain the RPF15 resistance gene (and phenotype conferred by it) described herein, e.g. obtainable by crossing a spinach plant, grown from seeds deposited under accession number NCIMB 42608, with another spinach plant. In other words, in one aspect the resistance gene or locus (or introgression fragment comprising the gene or locus) as present in/found in/as derived from (or as derivable from) seed deposit NCIMB 42608 is retained in the progeny plants.

Molecular markers may also be used to aid in the identification of the plants (or plant parts or nucleic acids obtained therefrom) comprising the RPF15 resistance gene or locus. For example, one can develop one or more molecular markers which are closely genetically physically linked to the RPF15 resistance gene or locus. This can be done by crossing a resistant spinach plant (comprising RPF15) with a susceptible spinach plant and developing a segregating population (e.g. F2 or backcross population) from that cross. The segregating population can then be phenotyped for Pfs resistance and genotyped using e.g. molecular markers such as SNPs (Single Nucleotide Polymorphisms), AFLPs (Amplified Fragment Length Polymorphisms; see, e.g., EP 534 858), or others, and by software analysis molecular markers which co-segregate with the Pfs resistance trait in the segregating population can be identified and their order and genetic distance (centiMorgan distance, cM) to the RPF15 resistance gene or locus can be identified. By BLAST® analysis against SpinachBase the physical location on chromosome 3 can be determined. If flanking markers are identified (either side of the RPF15 gene), the physical region of chromosome 3 where RPF15 is located between the markers can be identified.

Molecular markers which are closely linked to RPF15 resistance locus, e.g. markers at a 5 cM distance or less, can then be used in detecting and/or selecting plants (e.g. plants of the invention or progeny of a plant of the invention) or plant parts comprising or retaining the introgression fragment comprising the RPF15 resistance gene or locus. Such closely linked molecular markers can replace phenotypic selection (or be used in addition to phenotypic selection) in breeding programs, i.e. in Marker Assisted Selection (MAS). Preferably, linked markers are used in MAS. One sequence that can be used as a marker is the sequence comprising SNP_01 as described. More preferably, flanking markers are used in MAS, i.e. one marker on either side of the RPF15 gene or locus.

Using SEQ ID NO: 1, SEQ ID NO: 3 and the deposited seeds disclosed herein, the skilled person can also identify the sequence of the RPF15 gene itself using methods known in the art. For example, sequencing the chromosome 3 region and comparing the sequence to the sequence in e.g. SpinachBase, can be used to identify open reading frames on the introgression fragment, in order to identify the RPF15 gene itself. Modification of the RPF15 gene, e.g. by CRISPR-Cas9, can be used to prove the function of the gene. The skilled person can thus also generate plants comprising induced mutations in the RPF15 gene (e.g. in the promoter, protein coding sequence, other regulatory sequences). Plants comprising induced mutations in the RPF15 gene are encompassed herein.

In one aspect a method for screening, and optionally selecting, spinach seeds, plants or plant parts or DNA from such seeds, plants or plant parts for the presence of one or more markers linked to the RPF15 gene is provided.

In other aspects, the RPF15 gene is detectable using one or more nucleic acid probes, nucleic acid primers, or a combination thereof.

Thus, in one aspect the RPF15 gene is detectable by one or more nucleic acid probes, which hybridize to genomic DNA obtained from a plant or plant part comprising the RPF15 gene using stringent hybridization conditions.

A nucleic acid probe may for example be a DNA molecule which comprises SEQ ID NO: 1 (or which comprises Adenine at the location equivalent to 106 of a sequence comprising at least 90%, 91%, 92,%, 93%, 94%, 95%, 96%, 97%, 98% or 99% sequence identity to SEQ ID NO: 1) or a DNA molecule which comprises SEQ ID NO: 3 (or which comprises Cytosine at the location equivalent to 184 of a sequence comprising at least 90%, 91%, 92,%, 93%, 94%, 95%, 96%, 97%, 98% or 99% sequence identity to SEQ ID NO: 3) or the complement sequence for either. In another aspect the RPF15 gene is detectable by one or more nucleic acid primers, which amplify genomic DNA linked to the RPF15 gene. For example, the primers may amplify a nucleic acid molecule comprising aforementioned SEQ ID NO: 1, or a sequence comprising at 90%, 91%, 92,%, 93%, 94%, 95%, 96%, 97%, 98% or 99% sequence identity to SEQ ID NO: 1 having Adenine at the position equivalent to 106 or SEQ ID NO: 3, or a sequence comprising at 90%, 91%, 92,%, 93%, 94%, 95%, 96%, 97%, 98% or 99% sequence identity to SEQ ID NO: 3 having Cytosine at the position equivalent to 184. Suitable primers are for example the 70 to 100 bp upstream and 70 to 100 bp downstream of the SNP marker can be selected to design a forward and a reverse primer, which amplify the marker. The primers can be used e.g. for SNP genotyping, e.g. in a KASP-assay for detecting the SNP genotype for SNP_01 and/or SNP_02.

Any other type of molecular marker and/or other assay that is able to identify the relative presence or absence of a trait of interest (i.e. the RPF15 gene or locus) in a plant or plant part can also be useful for breeding purposes.

In DNA sequences nucleotide ambiguity codes are known in the art (see IUPAC codes), e.g. Y represents C or T; K represents T or G; R represents A or G.

DEPOSIT INFORMATION

A representative number of seed of *Spinacia oleracea* NCIMB 42608 was deposited by Nunhems B.V. under the Budapest Treaty on 12 Jul. 2016, at the NCIMB Ltd., Ferguson Building, Craibstone Estate, Bucksburn, Aberdeen AB21 9YA, United Kingdom (NCIMB). Access to the deposit will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Various modifications and variations of the described products and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in plant breeding, chemistry, biology, plant pathology or related fields are intended to be within the scope of the following claims.

The present invention will be further illustrated in the following Examples which are given for illustration purposes only and are not intended to limit the invention in any way.

EXAMPLES

1—Selection of a Wild Donor and Crossing the RPF15 Gene from the Wild Donor into Cultivated Spinach Several wild accessions were tested for resistance to infection with *Peronospora farinosa* f. sp. *spinaciae* races 1 to 16 and isolate UA0514. A *Spinacia turkestanica* accession was found to be resistant to at least Pfs races 8, 9, 11, 13 and 16 and selected.

The selected plant (resistance donor) was crossed with a cultivated spinach plant, that did not have any known background resistance to Pfs. Progeny plants were tested for Pfs resistance to at least Pfs races 8, 9, 11, 13 and 16 as exhibited by the selected plant (donor), and the resistant progeny plants were selected and backcrossed with said cultivated spinach plants and selfed for several generations to generate a line comprising the introgression fragment in homozygous form. Thus, the resistance from the *Spinacia turkestanica* donor was introgressed into cultivated spinach plants. Seeds of a plant line thus obtained were deposited with the NCIMB under number NCIMB 42608.

2—Pfs Resistance Phenotype of Cultivated Spinach Comprising the RPF15 Gene

The resistance to *Peronospora farinosa* infection was tested with the help of a differential set (obtainable from a.o. Naktuinbouw, The Netherlands).

Spinach plants grown from NCIMB 42608 seed (comprising the RPF15gene) were planted along with the differential set and spinach plants from other genotypes serving as checks in trays containing BVB substrate (Euroveen, Grubbenvorst), and covered with Agra-vermiculite (Pull, Rhenen). Per test at least 10 plants from one genotype each where tested in one or two replications. The trays were placed in a climate cell at 12° C./15° C. (day/night) with a 12 h photoperiod. Plants were inoculated by spraying a sporangial suspension ($2.5 \times 10^5$/ml) of a pathogenic race of *Peronospora farinosa* f. sp. *spinaciae* 14 days after seeding. In this manner pathogenic races were assayed. The inoculated plants were covered with transparent plastic material with 100% relative humidity for a 24 h period, after this period the plastic was removed on top to lower the relative humidity to 80%.

After 10 days, the plants were scored as 'resistant' or 'susceptible' based on symptoms of pathogen sporulation on the cotyledons and true leaves, as described by Irish et al. (2007; Plant Dis. 91: 1392-1396). A plant line exhibiting evidence of sporulation was considered 'susceptible'. A plant line where at least 85% of individuals of the line did not exhibit sporulation was considered 'resistant'. Resistant plants were re-inoculated to assess whether plants initially scored as resistant had escaped infection, or whether they were truly resistant. These plants were scored again 10 days after the second inoculation. Any genotype with <15% of plants being categorized as 'susceptible' (i.e. with more than 85% of plants not showing sporulation) were considered as a resistant genotype.

The new resistance gene, RPF15, as present in NCIMB 42608 in homozygous form, was found to confer resistance to Pfs 1, 2, 3, 4, 5, 6, 7, 8, 9, 11, 12, 13, 14, and 16 and isolate UA0514. Table 2 shows the resistances of spinach plants grown from NCIMB 42608 seed (comprising RPF15 homozygously).

Lines homozygous for RPF11, RPF12 or RPF13 were found not to be resistant to Pfs race 16

| Line comprising gene | Pfs 8 | Pfs 9 | Pfs 10 | Pfs 11 | Pfs 12 | Pfs 13 | Pfs 14 | Pfs 15 | Pfs 16 |
|---|---|---|---|---|---|---|---|---|---|
| RPF11 (homozygous) | – | – | – | – | – | – | – | – | + |
| RPF12 (homozygous) | – | – | – | – | – | – | – | – | + |
| RPF13 (homozygous) | – | – | – | – | – | – | – | – | + |

The susceptible and resistant differential varieties of Table 1 were used as checks and behaved as expected according to the standard as given in Table 1 (data not shown).

TABLE 2

Disease resistance of RPF15

| Line | Pfs 1 | Pfs 2 | Pfs 3 | Pfs 4 | Pfs 5 | Pfs 6 | Pfs 7 | Pfs 8 | Pfs 9 | Pfs 10 | Pfs 11 | Pfs 12 | Pfs 13 | Pfs 14 | Pfs 15 | Pfs 16 | Pfs 17 | UA0514 |
|---|---|---|---|---|---|---|---|---|---|---|---|---|---|---|---|---|---|---|
| NCIMB 42608 (comprising RPF75 homozygous) | − | − | − | − | − | − | − | − | − | + | − | (−) | − | (−) | + | − | − | − |

Legend: (−means resistant; +means susceptible; (−) means intermediate resistant)

3—Introgression of the RPF15 Resistance Trait into Other Spinach Plants

In another experiment, a spinach plant grown from NCIMB 42608 seed was crossed (as a father) with a different spinach plant susceptible to the race to be tested. Plants of the F1 population were tested for Pfs resistance against Pfs races 8, 9, 11, 13 and 16, as described in Example 2. It was observed that the heterozygous F1 plants retained the resistance against Pfs races 8, 9, 11, 13 and 16, and thus it was concluded that the resistance to these races is dominant. In the F2 population the resistance to these races will segregate in a 3 (resistant): 1 (susceptible) ratio.

4—Development of a Marker Linked to RPF15 and Alignments

An F2 population was developed by crossing spinach plant of NCIMB 42608 (comprising the RPF15 gene) with a spinach plant that does not have the RPF15 resistance gene and does not have background resistance to Pfs. Linkage mapping was conducted, and two Single Nucleotide Polymorphism marker (SNP), SNP_01 and SNP_02 shown in Table 3, was identified linked to the RPF15 gene.

SEQ ID NO: 1 comprises Adenine at nucleotide 106 and SEQ ID NO: 2 comprises a Guanine at nucleotide 106. SEQ ID NO: 3 comprises Cytosine at nucleotide 184 and SEQ ID NO: 4 comprises a Guanine at nucleotide 184. SEQ ID NO: 1 and SEQ ID NO: 2 are 204 bp. SEQ ID NO: 3 and SEQ ID NO: 4 are 299 bp. As mentioned before, the recurrent parent is susceptible.

SEQ ID NO: 1 and 2 were also used in a BLAST® analysis against SpinachBase genome sequence (of Chinese spinach line SP75). This analysis showed that SEQ ID NO: 1 and 2 are located on chromosome 3, starting at nucleotide 1091059 and ending at nucleotide 1090856, with the SNP_01 being at nucleotide 1090954 (comprising an A at this nucleotide) in SP75.

In a pairwise alignment of the genome sequence of SpinachBase with SEQ ID NO: 1, the two sequences have 97% sequence identity (pairwise alignment using Emboss program 'Needle', default parameters) (see FIG. 1, SNP_01 in bold). Both thus have Adenine at the SNP_01 position.

Furthermore, SEQ ID NO: 3 and 4 were used in a BLAST® analysis against SpinachBase genome sequence (of Chinese spinach line SP75). This analysis showed that SEQ ID NO: 3 and 4 are located on chromosome 3, starting

TABLE 3

A SNP marker linked to the RPF15 gene

| SNP and nucleotide position (nt) in the sequence | SNP genotype in spinach plant comprising the donor introgression fragment in homozygous form | SNP genotype of the recurrent parent (no introgression fragment) | Sequence comprising SNP_01 at nucleotide 106 |
|---|---|---|---|
| SNP_01 at nucleotide 106 of SEQ ID NO: 1 | AA (as present in NCIMB 42608) | GG | AACARAAATTCCGAATGCTTCAACGTTAGTTAT CTTCATTGGCTGCTGCTGCKTTTTTGGTGGGGA CCACAACTGGGTTCCTACTATYTGRTTATTTAG CATGTA[A/G]ACCGATTGCTTCGCRAACCAAT GACCAGAAGAAAGGACAACRACATCAAATTT CGGGATGTCTTGCATGAAAACTTCATCTGGGA CATCAAGGTGCAG (SEQ ID NO: 1 (A) and 2 (G)) |
| SNP_02 at nucleotide 184 of SEQ ID NO: 3 | CC (as present in NCIMB 42608) | GG | CGGTCTCCTTTACCGGAATTATCGCTCTCGAG GATCGGAAAAATGCTCGTATTACTTAGGGCTT GAGCTGAATCTCCATCACCAACAAGGGCAGG CAACGATCTCGAAAGATTATTCAAATTGTAAA ATGAAGCATAATTCGCATTATTATTATTCGACA TTCTCAATTTATCATAATTAGAC[C/G]GGCGTA TGCCACCATACCCGTGTCTAAACCCATGGATC GACCATTGATAACCGGGTTTATGAATCATTGA ATTTGTTTTGACTACCCCTAGGGGTGACCTTTT GCAATATCCACT (SEQ ID NO: 3 (C) and 4 (G)) | at nucleotide 607940 and ending at nucleotide 607636, with the SNP_02 being at nucleotide 607751 (comprising a G at this nucleotide) in SP75.

In a pairwise alignment of the genome sequence of SpinachBase with SEQ ID NO: 3, the two sequences have 96% sequence identity (pairwise alignment using Emboss program 'Needle', default parameters) (see FIG. 2, SNP_02 in bold). Whereas SEQ ID NO: 3 has Cytosine at nucleotide position 184 (SNP_02), and SEQ ID NO: 4 has Guanine at nucleotide position 184 (SNP_02), the reference genome also has Guanine at the position equivalent to nucleotide position 184 (SNP_02) of SEQ ID NO: 3 and SEQ ID NO: 4.

FIGS. 1 and 2 show that both SNP_01 and SNP_02, namely the Adenine at nucleotide 106 of SEQ ID NO: 1 and the Cytosine at nucleotide 184 of SEQ ID NO: 3 (both present on the introgression fragment from *S. turkestanica*) can be identified in sequences which are not 100% identical to SEQ ID NO: 1 or SEQ ID NO: 3, by pairwise sequence alignment of SEQ ID NO: 1 or SEQ ID NO: 3 with other sequences, e.g. sequences comprising at least 95% sequence identity to SEQ ID NO: 1 or SEQ ID NO: 3. The nucleotide position is such sequences is referred herein to as the nucleotide position 'equivalent' to position 106 in SEQ ID NO: 1 or to position 184 in SEQ ID NO: 3.

The Adenine at nucleotide 106 of SEQ ID NO: 1 (SNP_01), and the Cytosine at nucleotide 184 of SEQ ID NO: 3 (SNP_02), or at the equivalent nucleotide in a sequence comprising at least 95% sequence identity to SEQ ID NO: 1 or SEQ ID NO: 3, can be used to select plants and plant parts comprising the introgression fragment on which RPF15 is located.

5—Tests for Markers for Other Resistance Genes

WO2015054339 is a patent application, describing an introgression from *S. tetrandra* which comprises a Quantitative Trait Locus (QTL) conferring resistance to at least Pfs races 7, 10, 11, 12, 13, and 14. The application also discloses *S. tetrandra* flanking sequences, SEQ ID NO:1 and SEQ ID NO:2 which flank the QTL in the *S. tetrandra* donor described in WO2015054339, i.e. they flank said *S. tetrandra* gene conferring resistance to at least Pfs races 7, 10, 11, 12, 13, and 14. SEQ ID NO:1 of WO2015054339, hereafter referred to as "left *S. tetrandra* flanking marker", was added to this application as SEQ ID NO: 5, and SEQ ID NO:2 of WO2015054339, hereafter referred to as "right *S. tetrandra* flanking marker", was added to this application as SEQ ID NO:6.

The plant line deposited by the instant inventors was tested for the presence of said left and right *S. tetrandra* flanking markers. For each of the two flanking sequence regions described in the patent two primer pairs were designed, amplifying the corresponding region in DNA of the spinach plant grown from NCIMB 42608. In total 8 PCR primers were ordered and checked in silicio using JCeasar for resulting into a PCR fragment within the region.

PCR was performed on DNA of the spinach plant grown from NCIMB 42608 seed, using the primer pair combination for the left *S. tetrandra* flanking marker. The resulting PCR products were verified on agarose gel for the expected fragment length. The fragments had the expected size and were sequenced. The sequenced fragments of the material were aligned into contigs for each of the two flanking sequence regions in Sequencher. Based on these contigs, the spinach plant grown from NCIMB 42608 seed does not comprise the left *S. tetrandra* flanking marker. Instead, the NCIMB 42608 seed and plants grown from it were found to have another sequence (*S. oleracea* sequence), added to this application as SEQ ID NO: 7 (*S. oleracea*). The alignment between the two sequences is shown in FIG. 3. It is clear that the left *S. tetrandra* flanking sequence is not present in the seeds deposited.

A second PCR was performed on DNA of the spinach plant grown from NCIMB 42608 seed, using the primer pair combination for the right *S. tetrandra* flanking marker. The resulting PCR products were verified on agarose gel for the expected fragment length. The fragments had the expected size and were sequenced. The sequenced fragments of the material were aligned into contigs for each of the two flanking sequence regions in Sequencher. Based on these contigs, the spinach plant grown from NCIMB 42608 seed does not have the right *S. tetrandra* flanking marker. Instead, NCIMB 42608 seed and plants grown from it were again found to have another sequence, added to this application as SEQ ID NO: 8 (*S. oleracea*). The alignment between the two sequences is shown in FIG. 4. It is clear that the right *S. tetrandra* flanking sequence is not present in the seeds deposited. Please show me what you aligned and how Thus, neither the left nor the right *S. tetrandra* flanking marker is present in NCIMB 42608. NCIMB 42608 comprises the *S. oleracea* sequences SEQ ID NO: 7 and 8 in the region of the chromosome. Obviously, other cultivated spinach lines or varieties according to the invention may comprise SEQ ID NO: 7 and/or SEQ ID NO: 8 in their genome, or a sequence comprising at least 95%, 96%, 97%, 98% or 99% sequence identity to either of SEQ ID NO: 7 and 8.

Interestingly, when doing a BLAST® analysis in SpinachBase using these sequences, they appear to located on chromosome 3, and not on chromosome 6 as mentioned in the patent application WO2015054339.

|  | SpinachBase chromosome 3 - first and last nucleotide of the BLAST® alignment |
|---|---|
| SEQ ID NO: 5 (*S. tetrandra* patent) | 1418829-148725 |
| SEQ ID NO: 7 (*S. oleracea* in NCIMB 42608) | 1418964-1418666 (100% identical) |
| SEQ ID NO: 6 (*S. tetrandra*) | 711828-711679 |
| SEQ ID NO: 8 (*S. oleracea* in NCIMB 42608) | 711906-711670 (100% identical) |

The *S. tetrandra* QTL therefore appears to lie between 0.7 Mb and 1.41 Mb of chromosome 3.

6—Fine Mapping of RPF15

A further segregating population will be developed by crossing spinach plant grown from NCIMB 42608 seed (comprising the RPF15 gene) with a spinach plant that does not comprise the RPF15 resistance gene and does not comprise background resistance to Pfs. Also further SNPs will be added to the chromosome region where RPF15 is found. Further mapping will be conducted, generating more Single Nucleotide Polymorphism marker (SNP) markers linked to the RPF15 gene.

REFERENCES

Correll et al. 2011, Eur J Plant Pathol 129: 193-205
Correll et al. 2010, "Guidelines for Spinach Downy Mildew: *Peronspora ferinosa* f.sp. *spinaciae* (Pfs)" found on the website of the ISF Smith, P. G. and M. B. Zahara. 1956. New spinach immune to mildew. Calif. Agr. 10:15.

Smith, P. G., R. E. Webb, and C. H. Luhn. 1962. Immunity to race 2 of spinach downy mildew. Phytopathology 52:597-599.

Smith, P. G., R. E. Webb, A. M. Millett, and C. H. Luhn. 1961. Downy mildew on spinach. Calif. Agr. 15:5.

Brandenberger et al (1992) HORTSCIENCE 27(20):1118-1119.

Plantum press release, Denomination of Pfs: 16, a new race of downy mildew in spinach Mar. 15 2016

International Seed Federation Guidelines for Spinach Downy Mildew *Peronospora farinosa* f. sp. *spinaciae* (Pfs) Jim Correll, Lindsey du Toit, Steven Koike, and Kees van Ettekoven, December 2015; world wide web at worldseed.org/isf/differential_hosts.html Xu, C. et al. (2017, Nat. Commun. 8, 15275 doi: 10.1038/ncomms15275) "Draft genome of spinach and transcriptome diversity of 120 *Spinacia* accessions" (2017)

---

The invention claimed is:

1. A spinach plant of the species *Spinacia oleracea* comprising an introgression fragment on chromosome 3 from *Spinacia turkestanica*, wherein said introgression fragment comprises a single gene, referred to as RPF15 gene, which confers resistance against at least *Peronospora farinosa* races 8, 9, 11, 13 and 16 when the RPF15 gene is in heterozygous form and against races 1 to 9, 11 to 14, 16 and 17 when the RPF15 gene is in homozygous form and said introgression fragment comprising an Adenine (A) for SNP_01, which is an Adenine at nucleotide 106 of SEQ ID NO: 1, or an Adenine at the equivalent position in a sequence comprising at least 90% sequence identity to SEQ ID NO: 1 and said introgression fragment comprises a Cytosine (C) for SNP_02, which is a Cytosine at nucleotide 184 of SEQ ID NO: 3, or a Cytosine at the equivalent position in a sequence comprising at least 90% sequence identity to SEQ ID NO: 3, wherein said gene is the RPF15 gene as found in spinach seeds having been deposited under accession number NCIMB 42608.

2. The plant according to claim 1, wherein said RPF15 gene does not confer resistance against at least *Peronospora farinosa* races 10 and 15.

3. The plant according to claim 1, wherein said plant is heterozygous for the introgression fragment comprising the RPF15 gene and said plant is resistant against at least *Peronospora farinosa* races 8, 9, 11, 13 and 16.

4. The plant according to claim 1, wherein said plant is homozygous for the introgression fragment comprising the RPF15 gene and comprises the genotype AA for SNP_01 and CC for SNP_02.

5. The plant according to claim 1, wherein said plant is heterozygous for the introgression fragment comprising the RPF15 gene and comprises the genotype AG, AC or AT for SNP_01 and the genotype CG, CA or CT for SNP_02.

6. The plant according to claim 1, wherein said introgression fragment is the introgression fragment on chromosome 3 as found in spinach seeds having been deposited under accession number NCIMB 42608, or a subfragment of said introgression fragment retaining said RPF15 gene, and further retaining SEQ ID NO: 1 and/or SEQ ID NO: 3.

7. The plant according to claim 1, wherein said spinach plant is a hybrid plant, and said hybrid plant comprises said RPF15 gene in heterozygous form or homozygous form, or wherein said spinach plant is an inbred plant or a male parent line or a female parent line comprising said RPF15 gene in homozygous form.

8. The plant according to claim 1, wherein the spinach plant is savoy, semi-savoy, flat- or smooth leaved.

9. A seed from which the plant according to claim 1 can be grown.

10. A progeny plant of the spinach plant according to claim 1, wherein said progeny plant retains the RPF15 gene on chromosome 3, and further retains SNP_01 comprising an Adenine at nucleotide 106 of SEQ ID NO: 1, or an Adenine at the equivalent position in a sequence comprising at least 90% sequence identity to SEQ ID NO: 1 and/or retains SNP_02 comprising a Cytosine at nucleotide 184 of SEQ ID NO: 3, or a Cytosine at the equivalent position in a sequence comprising at least 90% sequence identity to SEQ ID NO: 3.

11. The progeny plant according to claim 10, wherein the progeny plant is produced by one or more methods selected from the group consisting of: selfing, crossing, double haploid production or transformation.

12. A method for generating a spinach plant comprising resistance against at least *Peronospora farinosa* races 8, 9, 11, 13 and 16, comprising
a) crossing a spinach plant comprising an introgression fragment on chromosome 3 from *Spinacia turkestanica*, wherein the introgression fragment comprises the RPF15 gene which confers resistance against at least *Peronospora farinosa* races 8, 9, 11, 13 and 16 when the RPF15 gene is in heterozygous form and said introgression fragment comprising an Adenine (A) for SNP_01, which is an Adenine at nucleotide 106 of SEQ ID NO: 1, or an Adenine at the equivalent position in a sequence comprising at least 90% sequence identity to SEQ ID NO: 1 and said introgression fragment comprises a Cytosine (C) for SNP_02, which is a Cytosine at nucleotide 184 of SEQ ID NO: 3, or a Cytosine at the equivalent position in a sequence comprising at least 90% sequence identity to SEQ ID NO: 3, wherein said gene is the RPF15 gene as found in spinach seeds having been deposited under accession number NCIMB 42608, with another spinach plant; and b) optionally selfing the progeny plant of step a one or more times to produce a further generation selfing progeny and optionally collecting seeds produced on the plant; and c) identifying the progeny plant of step a) or b) that comprises the RPF15 gene by determining whether the progeny plant comprises resistance against at least *Peronospora farinosa* races 8, 9, 11, 13 and 16 and comprises an Adenine for SNP_01 and/or a Cytosine for SNP_02.

13. A part of the spinach plant according to claim 1, wherein the part is a leaf, a part of a leaf, a stem, a part of a stem, a stalk, a part of a stalk, a shoot, a part of a shoot, a bud or a part of a bud, a cutting, a root, a part of a root, a root tip, a petiole, a part of a petiole, a cotyledon, a part of a cotyledon, a flower, a part of a flower, a petal, a part of a petal, a stamen, a part of a stamen, an anther, a part of an anther, pollen, a stigma, a part of a stigma, a style, a part of a style, an ovary, a part of an ovary, an ovule, a part of an ovule, a seed, a part of a seed, a seed coat, an embryo, a part of an embryo, a hypocotyl, an embryo sac, a fruit, a part of a fruit, a cell, a protoplast, callus, a microspore, meristem, or cambium, wherein said plant part retains the RPF15 gene conferring resistance against at least *Peronspora farinosa* races 8, 9, 11, 13 and 16 and further retains SNP_01 comprising an Adenine at nucleotide 106 of SEQ ID NO: 1, or an Adenine at the equivalent position in a sequence comprising at least 90% sequence identity to SEQ ID NO: 1, and SNP_02 comprising a Cytosine at nucleotide 184 of SEQ ID NO: 3, or a Cytosine at the equivalent position in a sequence comprising at least 90% sequence identity to SEQ ID NO: 3.

14. A cell culture or tissue culture comprising at least one cell or a tissue of the spinach plant according to claim 1, wherein said cell culture or tissue culture retains the RPF15 gene conferring resistance against at least *Peronospora farinosa* races 8, 9, 11, 13 and 16 and further retains SNP_01 comprising an Adenine at nucleotide 106 of SEQ ID NO: 1, or an Adenine at the equivalent position in a sequence comprising at least 90% sequence identity to SEQ ID NO: 1 and SNP_02 comprising a Cytosine at nucleotide 184 of SEQ ID NO: 3, or a Cytosine at the equivalent position in a sequence comprising at least 90% sequence identity to SEQ ID NO: 3.

15. A spinach plant regenerated from the cell culture or tissue culture of claim 14, wherein said plant retains the RPF15 gene conferring resistance against at least *Peronospora farinosa* races 8, 9, 11, 13 and 16 and further retains SNP_01 comprising an Adenine at nucleotide 106 of SEQ ID NO: 1, or an Adenine at the equivalent position in a sequence comprising at least 90% sequence identity to SEQ ID NO: 1, and SNP_02 comprising a Cytosine at nucleotide 184 of SEQ ID NO: 3, or a Cytosine at the equivalent position in a sequence comprising at least 90% sequence identity to SEQ ID NO: 3.

16. A method for identifying or selecting a spinach plant comprising an introgression fragment on chromosome 3 from *Spinacia turkestanica*, wherein said introgression fragment comprises a single gene, referred to as RPF15 gene, which confers resistance against at least *Peronospora farinosa* races 8, 9, 11, 13 and 16 when the RPF15 gene is in heterozygous form and against races 1 to 9, 11 to 14, 16 and 17 when the RPF15 gene is in homozygous form, said method comprising:

determining the presence of an Adenine at nucleotide 106 of SEQ ID NO: 1, or of an Adenine at the nucleotide position equivalent to nucleotide 106 of SEQ ID NO: 1 in a sequence comprising at least 90% sequence identity to SEQ ID NO: 1 and/or the presence of a Cytosine at nucleotide 184 of SEQ ID NO: 3, or of a Cytosine at the nucleotide position equivalent to nucleotide 184 of SEQ ID NO: 1 in a sequence comprising at least 90% sequence identity to SEQ ID NO: 3 in a spinach plant.

17. A cell of a cultivated spinach plant comprising an introgression fragment on chromosome 3 from *Spinacia turkestanica*, wherein said introgression fragment comprises a single gene, referred to as RPF15 gene, which confers resistance against at least *Peronospora farinosa* races 8, 9, 11, 13 and 16 when the RPF15 gene is in heterozygous form and against races 1 to 9, 11 to 14, 16 and 17 when the RPF15 gene is in homozygous form, wherein said gene is the RPF15 gene as found in spinach seeds deposited under accession number NCIMB 42608 and said gene is linked to SEQ ID NO: 1 comprising an Adenine at nucleotide 106, or to a sequence comprising at least 90% sequence identity to SEQ ID NO: 1 and comprising an Adenine at the nucleotide position equivalent to nucleotide 106 of SEQ ID NO: 1 and said gene is linked to SEQ ID NO: 3 comprising a Cytosine at nucleotide 184, or to a sequence comprising at least 90% sequence identity to SEQ ID NO: 3 and comprising a Cytosine at the nucleotide position equivalent to nucleotide 184 of SEQ ID NO: 3.

\* \* \* \* \*

SEQUENCE LISTING

<160> NUMBER OF SEQ ID NOS: 10

<210> SEQ ID NO 1
<211> LENGTH: 204
<212> TYPE: DNA
<213> ORGANISM: Spinacia turkestanica

<400> SEQUENCE: 1

```
aacaraaatt ccgaatgctt caacgttagt tatcttcatt ggctgctgct gckttttgg      60 tggggaccac aactgggttc ctactatytg rttatttagc atgtaaaccg attgcttcgc    120
raaccaatga ccagaagaaa ggacaacrac atcaaatttc gggatgtctt gcatgaaaac    180
ttcatctggg acatcaaggt gcag                                           204
```

<210> SEQ ID NO 2
<211> LENGTH: 204
<212> TYPE: DNA
<213> ORGANISM: Spinacia oleracea

<400> SEQUENCE: 2

```
aacaraaatt ccgaatgctt caacgttagt tatcttcatt ggctgctgct gckttttgg      60 tggggaccac aactgggttc ctactatytg rttatttagc atgtagaccg attgcttcgc    120
raaccaatga ccagaagaaa ggacaacrac atcaaatttc gggatgtctt gcatgaaaac    180
ttcatctggg acatcaaggt gcag                                           204
```

<210> SEQ ID NO 3
<211> LENGTH: 299
<212> TYPE: DNA
<213> ORGANISM: Spinacia turkestanica

<400> SEQUENCE: 3

```
cggtctcctt taccggaatt atcgctctcg aggatcggaa aaatgctcgt attacttagg     60
gcttgagctg aatctccatc accaacaagg gcaggcaacg atctcgaaag attattcaaa   120
ttgtaaaatg aagcataatt cgcattatta ttattcgaca ttctcaattt atcataatta   180
gaccggcgta tgccaccata cccgtgtcta aacccatgga tcgaccattg ataaccgggt   240
ttatgaatca ttgaatttgt tttgactacc cctaggggtg accttttgca atatccact    299
```

<210> SEQ ID NO 4
<211> LENGTH: 299
<212> TYPE: DNA
<213> ORGANISM: Spinacia oleracea

<400> SEQUENCE: 4

```
cggtctcctt taccggaatt atcgctctcg aggatcggaa aaatgctcgt attacttagg     60
gcttgagctg aatctccatc accaacaagg gcaggcaacg atctcgaaag attattcaaa   120
ttgtaaaatg aagcataatt cgcattatta ttattcgaca ttctcaattt atcataatta   180
```

```
gacgggcgta tgccaccata cccgtgtcta aacccatgga tcgaccattg ataaccgggt    240
ttatgaatca ttgaatttgt tttgactacc cctaggggtg accttttgca atatccact     299

<210> SEQ ID NO 5
<211> LENGTH: 148
<212> TYPE: DNA
<213> ORGANISM: Spinacia tetrandra

<400> SEQUENCE: 5
gcaaatagat gtgaaataac tttttacata tgcaaatata ttggaaatag cgaattatat    60
atataatatg gtttacatag gtttcgacag agggcttact cgtatttatt tgaataatat    120
gtcatatttg acgagaataa gaatgact                                      148

<210> SEQ ID NO 6
<211> LENGTH: 148
<212> TYPE: DNA
<213> ORGANISM: Spinacia tetrandra

<400> SEQUENCE: 6
gctgctgcat catagggtga tagttccttc cttttttcctt tatcattggt agatcgtttg   60
gcaaaagcct gtggcaccaa tacaacaaaa ggttaagata aatttgtttg ctatgaccat    120
attctaatca aaagaacata gcaacata                                      148

<210> SEQ ID NO 7
<211> LENGTH: 299
<212> TYPE: DNA
<213> ORGANISM: Spinacia oleracea

<400> SEQUENCE: 7
ggaagaacat tagtactagc ttaattgaat attccataac ttttttatttt tgcttaatta   60 gattgtggtt tgaagctatg caaatagatg tgaaataact ttttattttt gcttaattag    120
attgtggttt gaagctatgc aaatagatgt gaaatagcga atatatatta tataatatgg    180
tttacataga tttcgacaga ggggttactc gtatttgttt gaataatatt tcatatttga    240
tgaaaaatag ggattactta atcttaaaat agcatttatg ctttactcta agggtgtta     299

<210> SEQ ID NO 8
<211> LENGTH: 237
<212> TYPE: DNA
<213> ORGANISM: Spinacia oleracea

<400> SEQUENCE: 8
gcaacggcaa gctctcgaag ggcacgtagg gccttagatc tgcgaataag gtaagccctg    60
aaggtccact ggatcaaagc tgctgcatca tagggtgata gttccttcct tttttccttta   120 tcattggtag atcttttggc aaaagcctgt atggcaccaa tacaacaaaa ggttaagata    180
aatttgtttg ctatgaccat attctaatca aaagaacata gcaacatatt caagggg      237

<210> SEQ ID NO 9
<211> LENGTH: 204
<212> TYPE: DNA
<213> ORGANISM: unknown
<220> FEATURE:
<223> OTHER INFORMATION: Spinachbase sequence of Figure 1

<400> SEQUENCE: 9
aacagaaatt ccgaatgctt caacgttagt tatcttcatt ggctgctgct gcgttttggg    60
tggggaccac aactgggttc ctactatctg gttatttagc atgtaaaccg attgcttcgc    120
```

```
aaaccaatga ccagaagaaa ggacaacaac atcaaatttc gggatgtctt gcatgaaaac      180
ttcatctggg acatcaaggt gcag                                            204

<210> SEQ ID NO 10
<211> LENGTH: 305
<212> TYPE: DNA
<213> ORGANISM: unknown
<220> FEATURE:
<223> OTHER INFORMATION: Spinachbase sequence of Figure 2

<400> SEQUENCE: 10
cggtctcctt taccggaatt atcgctctcg aggatcggaa aaatgctcgt attatttagg       60
gtttgagctg aatctccatc accaataagg gcaggcaatg atctcgaaag attattcaaa      120
ttgtaaaatg aagcataatt cgcgttatta ttattattat tcgacattct caatttatca      180
taattagacg ggcgtattcc accatacccg tgtctaaacc catggatcga ccattgataa      240
ccgggtttat gaatcattga atttgttttg actacccta ggggtgacct tttgcaatat       300
ccact                                                                 305
```